United States Patent
Beck et al.

(10) Patent No.: US 11,198,692 B2
(45) Date of Patent: Dec. 14, 2021

(54) DIHYDRO-PYRROLO-PYRIDINE DERIVATIVES

(71) Applicant: Pfizer Inc., New York, NY (US)

(72) Inventors: Elizabeth Mary Beck, Oxford (GB); Michael Aaron Brodney, Newton, MA (US); Matthew Frank Brown, Stonington, CT (US); Christopher Ryan Butler, Canton, MA (US); Adam Matthew Gilbert, Guilford, CT (US); Erik Alphie Lachapelle, Uncasville, CT (US); Laura Ann McAllister, Arlington, MA (US); Daniel Paul Uccello, Colchester, CT (US); Lei Zhang, Auburndale, MA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 16/625,202

(22) PCT Filed: Jun. 14, 2018

(86) PCT No.: PCT/IB2018/054390
§ 371 (c)(1),
(2) Date: Dec. 20, 2019

(87) PCT Pub. No.: WO2018/234953
PCT Pub. Date: Dec. 27, 2018

(65) Prior Publication Data
US 2020/0262833 A1 Aug. 20, 2020

Related U.S. Application Data

(60) Provisional application No. 62/523,306, filed on Jun. 22, 2017.

(51) Int. Cl.
*C07D 471/04* (2006.01)
(52) U.S. Cl.
CPC ................ *C07D 471/04* (2013.01)
(58) Field of Classification Search
CPC .................................. C07D 471/04
USPC ..................................... 546/113
See application file for complete search history.

(56) References Cited

U.S. PATENT DOCUMENTS

| 2,767,191 A | 10/1956 | Wright |
| 3,123,612 A | 3/1964 | Gadekar |
| 2012/0122842 A1 | 5/2012 | Curtin |

FOREIGN PATENT DOCUMENTS

| WO | WO2014035829 | 3/2014 |
| WO | WO2015027214 | 2/2015 |
| WO | WO2018002760 | 1/2018 |
| WO | WO2018066718 | 4/2018 |

OTHER PUBLICATIONS

William Wright: "The Preparation of Some Merimine Derivatives", May 5, 1957, pp. 2199-2203, XP055505878, Retrieved from the Internet: URL:https://pubs.acs.org/doi/pdfplus/10.1021/ja01566a046 [retrieved on Sep. 10, 2018].
Database Registry [Online] Chemical Abstracts Service, Columbus, Ohio, US; Jan. 29, 2017, retrieved from STN Database accession No. 2061132-34-9 (1 page).
Database Registry [Online] Chemical Abstracts Service, Columbus, Ohio, US; Jan. 26, 2017, retrieved from STN Database accession No. 2059731-45-0 (1 page).
Database Registry [Online] Chemical Abstracts Service, Columbus, Ohio, US; May 2, 2017, retrieved from STN Database accession No. 2094144-40-6 (1 page).

*Primary Examiner* — Taofiq A Solola
(74) *Attorney, Agent, or Firm* — Haley Guiliano LLP; James F. Haley, Jr.

(57) ABSTRACT

The present invention provides, in part, compounds of Formula I, or an N-oxide thereof, or a pharmaceutically acceptable salt of the compound or the N-oxide, wherein: $(R^1)a$, $(R^2)b$, $(R^3)c$, L, A, and E are as described herein; processes for the preparation of; intermediates used in the preparation of; and compositions containing such compounds, N-oxides, or salts, and their uses for treating M4-mediated (or M4-associated) disorders including, e.g., Alzheimer's Disease, schizophrenia (e.g., its cognitive and negative symptoms), pain, addiction, and a sleep disorder.

(I)

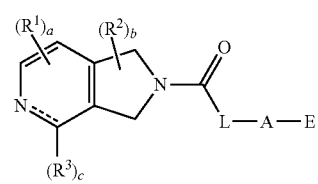

21 Claims, No Drawings

DIHYDRO-PYRROLO-PYRIDINE DERIVATIVES

CROSS- REFERENCE TO RELATED APPLICATIONS

This application is a United States National Phase Application filed under 35 U.S.C. § 371 from International Patent Application No. PCT/IB2018/054390, filed Jun. 14, 2018, which claims the benefit of priority to US Provisional Patent Application Serial No. 62/523,306, filed Jun. 22, 2017, the disclosures of which are hereby incorporated by reference in their entireties.

FIELD OF THE INVENTION

The present invention generally relates to novel dihydro-pyrrolo-pyridine derivatives, which are activators of the muscarinic M4 receptor, salts thereof, pharmaceutical compositions thereof, and uses thereof in the treatment of M4-mediated diseases and disorders such as Schizophrenia, Alzheimer's Disease, Dementia with Lewy Bodies, Parkinson's Disease and related memory and executive dysfunction, agitation, and psychosis associated therewith.

BACKGROUND OF THE INVENTION

Patients with Schizophrenia, Alzheimer's Disease, Parkinson's Disease, Huntington's Disease, depression and various other neurological/neurodegenerative diseases frequently suffer from behavioral and cognitive impairments resulting in debilitating disruption to their daily lives. Over the years many pharmacological treatments have been discovered that provide some improvement in behavior and cognitive function. However, the improvement is modest at best, and as is often the case, the underlying dose-limiting adverse effects associated with these treatments, including extrapyramidal and metabolic side-effects, lead to partial responsiveness, and non-compliance.

In an effort to discover new and improved pharmacological treatments, researchers began to look at the muscarinic acetylcholine receptor (mAChR) as a viable mechanism. There are five mAChRs subtypes (M1-M5) that have been identified and are part of the G protein-coupled receptor (GPCR) superfamily. These subtypes are distributed widely throughout the periphery and the central nervous system, with the M1 and M4 subtypes being predominantly expressed in the CNS.

Researchers have since focused on identifying subtype selective M4 muscarinic acetylcholine receptor activators. For example, positive allosteric modulators (PAMs) of the M4 muscarinic acetylcholine receptor have gained attention as a further method of treating the behavioral impairments associated with schizophrenia and other neuropsychiatric disorders, e.g., Alzheimer's Disease. [See: Bubser, Michael, et al., "Selective Activation of M4 Muscarinic Acetylcholine Receptors reverses MK-801-Induced Behavioral Impairments and Enhances Associative Learning in Rodents", American Chemical Society, Chemical Neuroscience (2014); and Bynum, Nellie E., et al., "Antipsychotic Drug-Like Effects of the Selective M4 Muscarinic Acetylcholine Receptor Positive Allosteric Modulator VU0152100", Neuropsychopharmacology (2014) 1-16]. While the etiology of schizophrenia is unclear, it is believed that an imbalance in the dopaminergic system plays a major role. mAChR receptors are known for their regulation of dopamine levels in critical regions of the brain involved with psychosis, with M4 being the primary subtype for dopamine regulation. (See: Chan, W. Y., et al., "Allosteric Modulation of the Muscarinic M4 receptor as an Approach to Treating Schizophrenia", PNAS, August 2008, Vol. 105 No. 31 p. 10978; and Byun, Nellie, et al., "Antipsychotic Drug-Like Effects of the Selective M4 Muscarinic Acetylcholine Receptor Positive Allosteric Modulator VU0152100", Neuropsychopharmacology (2014) 1-16). Another hypothesis for M4 in schizophrenia is its ability to affect hippocampal circuitry (Shirley, Jana K., et al., An allosteric potentiator of M4 mAChR modulates hippocampal synaptic transmission", Nature Chemical Biology, Vol. 4, No. 1, January 2008; and Dasari, Sameera, et. al., "M1 and M4 Receptors Modulate Hippocampal Pyramidal Neurons", J. Neurophysiology 105: 779-792, 2011) through modulation of the hippocampal trisynaptic pathway which has been reported to be disregulated in Schizophrenic (Tamminga, Carol A., et. al., "Glutamate Dysfunction in Hippocampus: Relevance of Dentate Gyrus and CA3 Signaling", Schizophrenia Bulletin Vol. 38, no. 5, pp. 927-935, 2012), Alzheimer's Disease (Quiroz et al 2010 Ann Neurol, Filipini et al 2009 PNAS) and aMCI patients (Bakker, A., et. al., "Response of the medial temporal lobe network in amnestic mild cognitive impairment to therapeutic intervention assessed by fMRI and memory task performance", Neuromalge: Clinical 7 (2015) 688-698). Hyperactivity in the hippocampal trisynaptic pathway has been proposed as a likely cause for psychosis in schizophrenics (Tamminga, et al.).

Vanderbilt University has published several International Patent Applications directed to positive allosteric modulators (PAMs) of the muscarinic M4 acetylcholine receptor some of which include: WO2013/126856A1 (substituted 5-aminothieno[2,3-C]pyridazine-6-carboxamide analogs); WO2014/035829A1 (substituted 3-aminothieno[2,3-C]pyridine-2-carboxaminde analogs); WO2015/027204A1 (substituted thieno[2,3-B]pyridine-2-carboxamide analogs); and WO2015/027214 (substituted thieno[2,3-C]pyridazine-6-carboxamide analogs).

WO02006/047124A1 (Lilly) discloses thienopyridines as allosteric potentiators of the M4 muscarinic receptor.

New or improved activators, including positive allosteric modulators, of the muscarinic M4 receptors are needed for providing new and improved therapies to treat M4-mediated diseases and disorders such as Schizophrenia, Alzheimer's Disease and others described herein.

SUMMARY OF THE INVENTION

The present invention provides, in part, a compound of Formula I:

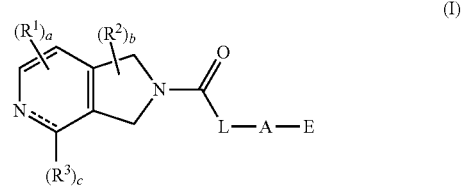

or an N-oxide thereof, or a pharmaceutically acceptable salt of the compound or the N-oxide, wherein:
each $R^1$, when present, is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted $(C_1-C_6)$alkylthio, optionally substituted $(C_1-C_6)$alkoxy, optionally substituted $(C_3-C_6)$cycloalkyl, optionally substituted —O—$(C_3-C_6)$cycloalkyl, —N($R^4$)($R^5$), —N($R^4$)(C(=O)($R^5$)), —C(=O)N($R^4$)($R^5$), —O—C(=O)—N($R^4$)($R^5$), —C(=O)—$R^4$, and —C(=O)—O$R^4$;

a is an integer selected from 0, 1, 2, and 3;

each $R^2$, when present, is independently selected from the group consisting of hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —N($R^4$)($R^5$), —N($R^4$)(C(=O)($R^5$)), —C(=O)N($R^4$)($R^5$), —O—C(=O)—N($R^4$)($R^5$), —C(=O)—$R^4$, and —C(=O)—O$R^4$;

b is an integer selected from 0, 1, 2, 3, and 4;

$R^3$, when present, is independently selected from the group consisting of halogen, cyano, hydroxy, oxo, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, optionally substituted $(C_3-C_6)$cycloalkyl, optionally substituted —O—$(C_3-C_6)$cycloalkyl, optionally substituted (5- to 6-membered)heteroaryl, —N($R^4$)($R^5$), —N($R^4$)(C(=O)($R^5$)), —C(=O)N($R^4$)($R^5$), —O—C(=O)—N($R^4$)($R^5$), —C(=O)—$R^4$, and —C(=O)—O$R^4$, provided that when $R^3$ is oxo, then ═══ is a single bond, or when c is 0 then $R^3$ is absent and ═══ is a double bond;

c is an integer selected from 0 and 1;

L is selected from —$(CH_2)_m$—, and —O—, wherein m is an integer selected from 0, 1 and 2;

A is absent or selected from the group consisting of $(C_3-C_6)$cycloalkyl and (4- to 10-membered)heterocycloalkyl, wherein said cycloalkyl and heterocycloalkyl are each optionally substituted with one to five substituents independently selected from the group consisting of halogen, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —N($R^4$)($R^5$), —N($R^4$)(C(=O)($R^5$)), —C(=O)N($R^4$)($R^5$), —O—C(=O)—N($R^4$)($R^5$), —C(=O)—$R^4$, and —C(=O)—O$R^4$;

E is selected from $(C_3-C_{12})$cycloalkyl, $(C_6-C_{10})$aryl, (5- to 6-membered)heterocycloalkyl, and (5- to 10-membered)heteroaryl, wherein said cycloalkyl, aryl, and heteroaryl are optionally substituted with one to five substituents independently selected from the group consisting of halogen, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, optionally substituted $(C_3-C_6)$cycloalkyl, methyloxetanyl, —N($R^4$)($R^5$), —N($R^4$)(C(=O)$R^5$), —C(=O)N($R^4$)($R^5$), —O—C(=O)—N($R^4$)($R^5$), —C(=O)—$R^4$, and —C(=O)—O$R^4$; and $R^4$ and $R^5$ at each occurrence are each independently selected from hydrogen and optionally substituted $(C_1-C_6)$alkyl; or $R^4$ and $R^5$ taken together with the nitrogen to which they are attached form an optionally substituted (4- to 6-membered)heterocycloalkyl.

In some embodiments, the invention also provides one or more of the compounds or an N-oxide thereof, or a pharmaceutically acceptable salt of the compound or the N-oxide, described in Examples 1-59.

The compounds of Formula I are useful for treating or preventing M4-mediated diseases and/or disorders such as Schizophrenia, Alzheimer's Disease, Dementia with Lewy Bodies, Parkinson's disease and related memory and executive dysfunction, agitation, and behavioral and cognitive impairment associated with the above, as well as pain, trauma, cardiologic, thrombotic, metabolic, autoimmune and inflammatory diseases or disorders, and disorders associated with enhanced endothelial activity/impaired endothelial barrier function.

The present invention is also directed to the use of the compounds described herein, or an N-oxide thereof, or a pharmaceutically acceptable salt of the compound or the N-oxide, in the preparation of a medicament for the treatment or prevention of a condition amenable to activation (e.g., modulation of the allosteric binding site) of the M4 muscarinic acetylcholine receptor (mAChR).

The present invention is also directed to pharmaceutically acceptable formulations containing an admixture of a compound(s) of the present invention or an N-oxide thereof, or a pharmaceutically acceptable salt of the compound or the N-oxide, and at least one excipient formulated into a pharmaceutical dosage form. Examples of such dosage forms include tablets, capsules, suppositories, gels, creams, ointments, lotions, solutions/suspensions for injection (e.g., depot), aerosols for inhalation and solutions/suspensions for oral ingestion.

DETAILED DESCRIPTION OF THE INVENTION

The headings within this document are being utilized only to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number: As used herein, the term "activator(s) of the muscarinic M4 receptor" means the compounds of the present invention are: i) agonists, where the compound induces an effect on the M4 receptor absent the presence of a native ligand (e.g. acetylcholine); ii) a positive allosteric modulator (PAM), wherein the compound induces an effect on the receptor in the presence of a suboptimal concentration of native ligand; or iii) the compounds of the present invention possess both agonist and PAM activity.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl ring.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

The term "$(C_1-C_6)$alkyl", as used herein, refers to a saturated, branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl.

The term "optionally substituted $(C_1-C_6)$alkyl", as used herein, refers to a $(C_1-C_6)$alkyl as defined above, in which one or more hydrogen atoms are replaced by a substituent selected from the group consisting of halogen, oxo, cyano, hydroxy, —$SF_5$, nitro, —$(C_1-C_6)$alkoxy, —$N(R^4)(R^5)$, —$N(R^4)(C(=O)R^5)$, —$N(R^4)C(=O)$—$OR^5$, —$C(=O)$—$N(R^4)(R^5)$, —O—$C(=O)$—$N(R^4)(R^5)$, —$C(=O)$—$R^4$, —$C(=O)$—$OR^4$, and optionally substituted $(C_3-C_8)$cycloalkyl, in which $R^4$ and $R^5$ are each independently selected from hydrogen and optionally substituted $(C_1-C_6)$alkyl. For example, a $(C_1-C_6)$alkyl moiety can be substituted with one or more halogen atoms to form a "halo$(C_1-C_6)$alkyl". Representative examples of a halo$(C_1-C_6)$alkyl include, but are not limited to, fluoromethyl, 2-fluoroethyl, difluoromethyl, trifluoromethyl, and pentafluoroethyl. Other examples of optionally substituted $(C_1-C_6)$alkyl include, but are not limited to, methanol, methoxymethyl, (dimethylamino)methyl, and cyclopropylmethyl.

The term "$(C_2-C_6)$alkenyl" refers to an aliphatic hydrocarbon having from 2 to 6 carbon atoms and having at least one carbon-carbon double bond, including straight chain or branched chain groups having at least one carbon-carbon double bond. Representative examples include, but are not limited to, ethenyl, 1-propenyl, 2-propenyl (allyl), isopropenyl, 2-methyl-1-propenyl, 1-butenyl, 2-butenyl, and the like. When the compounds of the invention contain a $(C_2-C_6)$alkenyl group, the compound may exist as the pure E (entgegen) form, the pure Z (zusammen) form, or any mixture thereof.

The term "optionally substituted $(C_2-C_6)$alkenyl" refers to a $(C_2-C_6)$alkenyl as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^4)(R^5)$, —$N(R^4)(C(=O)R^5)$, —$N(R^4)C(=O)$—$OR^5$, —$C(=O)$—$N(R^4)(R^5)$, —O—$C(=O)$—$N(R^4)(R^5)$, —$C(=O)$—$R^4$, —$C(=O)$—$OR^4$, and optionally substituted $(C_3-C_8)$cycloalkyl, in which $R^4$ and $R^5$ are each independently selected from hydrogen and optionally substituted $(C_1-C_6)$alkyl.

The term "$(C_2-C_6)$alkynyl" refers to an aliphatic hydrocarbon having two to six carbon atoms and at least one carbon-carbon triple bond, including straight chains and branched chains having at least one carbon-carbon triple bond. Representative examples include, but are not limited to, ethynyl, propynyl, butynyl, pentynyl, and hexynyl.

The term "optionally substituted $(C_2-C_6)$alkynyl" refers to a $(C_2-C_6)$alkynyl as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^4)(R^5)$, —$N(R^4)(C(=O)R^5)$, —$N(R^4)C(=O)$—$OR^5$, —$C(=O)$—$N(R^4)(R^5)$, —O—$C(=O)$—$N(R^4)(R^5)$, —$C(=O)$—$R^4$, —$C(=O)$—$OR^4$, and optionally substituted $(C_3-C_8)$cycloalkyl, in which $R^4$ and $R^5$ are each independently selected from hydrogen and optionally substituted $(C_1-C_6)$alkyl.

The term "$(C_1-C_6)$alkoxy" as used herein, refers to a $(C_1-C_6)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy.

The term "optionally substituted $(C_1-C_6)$alkoxy" as used herein, refers to a $(C_1-C_6)$alkoxy group as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^4)(R^5)$, —$N(R^4)(C(=O)R^5)$, —$N(R^4)C(=O)$—$OR^5$, —$C(=O)$—$N(R^4)(R^5)$, —O—$C(=O)$—$N(R^4)(R^5)$, —$C(=O)$—$R^4$, —$C(=O)$—$OR^4$, and optionally substituted $(C_3-C_8)$cycloalkyl, in which $R^4$ and $R^5$ are each independently selected from hydrogen and optionally substituted $(C_1-C_6)$alkyl. For example, a $(C_1-C_6)$alkoxy can be substituted with one or more halogen atoms to form a "halo$(C_1-C_6)$alkoxy". Representative examples of a halo $(C_1-C_6)$alkoxy include, but are not limited to, fluoromethoxy, difluoromethoxy, 2-fluoroethoxy, trifluoromethoxy, and pentafluoroethoxy.

The term "$(C_1-C_6)$alkythio", as used herein, refers to a $(C_1-C_6)$alkyl group, as defined above, attached to the parent molecular moiety through a sulfur atom. Representative examples of a $(C_1-C_6)$alkylthio include, but are not limited to, methylthio, ethylthio, propylthio, and the like.

The term "optionally substituted $(C_1-C_6)$alkythio", as used herein, refers to a $(C_1-C_6)$alkylthio group, as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^4)(R^5)$, —$N(R^4)(C(=O)R^5)$, —$N(R^4)C(=O)$—$OR^5$, —$C(=O)$—$N(R^4)(R^5)$, —O—$C(=O)$—$N(R^4)(R^5)$, —$C(=O)$—$R^4$, —$C(=O)$—$OR^5$, and optionally substituted $(C_3-C_8)$cycloalkyl, in which $R^4$ and $R^5$ are each independently selected from hydrogen and optionally substituted $(C_1-C_6)$alkyl.

As used herein, the term "$(C_3-C_{12})$cycloalkyl" refers to a carbocyclic substituent obtained by removing hydrogen from a saturated carbocyclic molecule wherein the cyclic framework has 3 to 12 carbons. A "$(C_3-C_8)$cycloalkyl" refers to a carbocyclic substituent obtained by removing hydrogen from a saturated carbocyclic molecule wherein the cyclic framework has 3 to 8 carbons. A "$(C_3-C_6)$cycloalkyl" refers to a carbocyclic substituent obtained by removing hydrogen from a saturated carbocyclic molecule having from 3 to 6 carbon atoms. A "cycloalkyl' may be a monocyclic ring, examples of which include cyclopropyl, cyclobutyl, cyclopentyl, cyclohexyl, cycloheptyl, and cyclooctyl. Also included in the definition of cycloalkyl are unsaturated non-aromatic cycloalkyls such as, but not limited to, cyclohexenyl, cyclohexadienyl, cyclopentenyl, cycloheptenyl, and cyclooctenyl. Alternatively, a cycloalkyl may contain more than one ring such as a "$(C_4-C_8)$bicycloalkyl". The term "$(C_4-C_8)$bicycloalkyl" refers to a bicyclic ring system containing from 4 to 8 carbon atoms. The bicycloalkyl may be fused, such as bicyclo[1.1.0]butanyl, bicyclo[2.1.0]pentanyl, bicyclo[2.2.0]hexanyl, bicyclo[3.1.0]hexanyl, bicyclo [3.2.0]heptanyl, and bicyclo[3.3.0]-octanyl. The term "bicycloalkyl" also includes bridged bicycloalkyl systems such as, but not limited to, bicyclo[2.2.1]heptanyl and bicyclo [1.1.1]pentanyl. Other bicyclic cycloalkyl rings systems include "$(C_3-C_{12})$cycloalkyls", wherein a 3-, 4-, 5- or 6-carbon cycloalkyl ring is fused together with another ring, such another cycloalkyl ring, an aromatic ring or a heteroaromatice ring. For example, a dihydroindenyl ring is a cycloalkyl ring wherein a cyclopentyl ring is fused together with a phenyl ring. Another example, a dihydrocyclopentapyridyl ring is a cycloalkyl ring wherein a cyclopentyl ring is fused together with a pyridinyl ring.

The term "optionally substituted $(C_3-C_8)$cycloalkyl" or "optionally substituted $(C_3-C_6)$cycloalkyl" refers to a $(C_3-C_8)$cycloalkyl or $(C_3-C_6)$cycloalkyl, as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-$ $C_6$)alkoxy, —N($R^4$)($R^5$), —N($R^4$)(C(=O)$R^5$), —N($R^4$)C(=O)—O$R^5$, —C(=O)—N($R^4$)($R^5$), —O—C(=O)—N($R^4$)($R^5$), —C(=O)—$R^4$, —C(=O)—O$R^5$, and optionally substituted ($C_3$-$C_8$)cycloalkyl, in which $R^4$ and $R^5$ are each independently selected from hydrogen and optionally substituted ($C_1$-$C_6$)alkyl.

The term "—O—($C_3$-$C_6$)cycloalkyl" refers to a ($C_3$-$C_6$)cycloalkyl as described above, attached to the parent molecular moiety through an oxygen atom. Representative examples of a —O—($C_3$-$C_6$)cycloalkyl include, but are not limited to, cyclopropoxy, cyclobutoxy, and the like.

The term "optionally substituted —O—($C_3$-$C_6$)cycloalkyl" refers to a —O—($C_3$-$C_6$)cycloalkyl as described above, in which one or more hydrogen atoms are replaced by a substituent selected from the group consisting of halogen, oxo, cyano, hydroxy, —$SF_5$, nitro, —($C_1$-$C_6$)alkyl, —($C_1$-$C_6$)alkoxy, —N($R^4$)($R^5$), —N($R^4$)(C(=O)$R^5$), —N($R^4$)C(=O)—O$R^5$, —C(=O)—N($R^4$)($R^5$), —O—C(=O)—N($R^4$)($R^5$), —C(=O)—$R^4$, —C(=O)—O$R^4$, and optionally substituted ($C_3$-$C_8$)cycloalkyl, in which $R^4$ and $R^5$ are each independently selected from hydrogen and optionally substituted ($C_1$-$C_6$)alkyl.

A "heterocycloalkyl," as used herein, refers to a cycloalkyl as defined above, wherein at least one of the ring carbon atoms is replaced with a heteroatom selected from nitrogen, oxygen or sulfur. The term "(4- to 6-membered)heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of 4 to 8 ring atoms, at least one of which is a heteroatom. A "(4- to 10-membered)heterocycloalkyl" means the heterocycloalkyl substituent contains a total of 4 to 10 ring atoms. A "(6-membered)heterocycloalkyl" means the heterocycloalkyl substituent contains a total of 6 ring atoms, at least one of which is a heteroatom. A "(5-membered)heterocycloalkyl" means the heterocycloalkyl substituent contains a total of 5 ring atoms at least one of which is a heteroatom. A heterocycloalkyl may be a single ring with up to 10 total members. Alternatively, a heterocycloalkyl as defined above may comprise 2 or 3 rings fused together, wherein at least one such ring contains a heteroatom as a ring atom (i.e., nitrogen, oxygen, or sulfur). The heterocycloalkyl substituent may be attached to the dihydropyrrolopyridine core of the compounds of the present invention via a nitrogen atom having the appropriate valence, or via any ring carbon atom. The heterocycloalkyl moiety may be optionally substituted with one or more substituents at a nitrogen atom having the appropriate valence, or at any available carbon atom.

Also included in the definition of "heterocycloalkyl" are heterocycloalkyls that are fused to a phenyl or naphthyl ring or to a heteroaryl ring such as, but not limited to, a pyridinyl ring or a pyrimidinyl ring.

Examples of heterocycloalkyl rings include, but are not limited to, azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydro-benzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydro-oxazolyl, morpholinyl, oxetanyl, tetrahydrodiazinyl, oxazinyl, oxathiazinyl, quinuclidinyl, chromanyl, isochromanyl, dihydrobenzodioxinyl, benzodioxolyl, benzoxazinyl, indolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like.

The term "optionally substituted heterocycloalkyl" [e.g., optionally substituted (4- to 10-membered)heterocycloalkyl] refers to a heterocycloalkyl, as defined above, in which one or more hydrogen atoms, where chemically permissible, are replaced by a substituent selected from the group consisting of halogen, oxo, cyano, hydroxy, —$SF_5$, nitro, —($C_1$-$C_6$)alkyl, —($C_1$-$C_6$)alkoxy, —N($R^4$)($R^5$), —N($R^4$)(C(=O)$R^5$), —N($R^4$)C(=O)—O$R^5$, —C(=O)—N($R^4$)($R^5$), —O—C(=O)—N($R^4$)($R^5$), —C(=O)—$R^4$, —C(=O)—O$R^4$, and optionally substituted ($C_3$-$C_8$)cycloalkyl, in which $R^4$ and $R^5$ are each independently selected from hydrogen and optionally substituted ($C_1$-$C_6$)alkyl.

A "($C_6$-$C_{10}$)aryl" refers to an all-carbon monocyclic or fused-ring polycyclic aromatic group having a conjugated pi-electron system containing from 6 to 10 carbon atoms, such as phenyl or naphthyl.

The term "optionally substituted ($C_6$-$C_{10}$)aryl" refers to a ($C_6$-$C_{10}$)aryl, as defined above, in which one or more hydrogen atoms are replaced by a substituent selected from the group consisting of halogen, oxo, cyano, hydroxy, —$SF_5$, nitro, —($C_1$-$C_6$)alkyl, —($C_1$-$C_6$)alkoxy, —N($R^4$)($R^5$), —N($R^4$)(C(=O)$R^5$), —N($R^4$)C(=O)—O$R^5$, —C(=O)—N($R^4$)($R^5$), —O—C(=O)—N($R^4$)($R^5$), —C(=O)—$R^4$, —C(=O)—O$R^4$, and optionally substituted ($C_3$-$C_8$)cycloalkyl, in which $R^4$ and $R^5$ are each independently selected from hydrogen and optionally substituted ($C_1$-$C_6$)alkyl.

As used herein, the term "heteroaryl" refers to monocyclic or fused-ring polycyclic aromatic heterocyclic groups with one or more heteroatom ring members (ring-forming atoms) each independently selected from oxygen (O), sulfur (S) and nitrogen (N) in at least one ring. A "(5- to 14-membered) heteroaryl" ring refers to a heteroaryl ring having from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)heteroaryl" ring refers to a heteroaryl ring having from 5 to 10 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)nitrogen-containing heteroaryl" ring refers to a heteroaryl ring having from 5 to 10 ring atoms in which at least one of the ring atoms is nitrogen, with the remaining ring atoms being independently selected from the group consisting of carbon, oxygen, sulfur, and nitrogen. A "(5- to 6-membered)heteroaryl" refers to a heteroaryl ring having from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 6-membered)nitrogen-containing heteroaryl" refers to a heteroaryl ring having from 5 to 6 ring atoms in which one of the heteroatoms in the ring is a nitrogen. A "(6-membered)nitrogen-containing heteroaryl" refers to a heteroaryl ring having 6 ring atoms in which one of the heteroatoms in the ring is a nitrogen. A "(5-membered)nitrogen-containing heteroaryl" refers to a heteroaryl ring having 5 ring atoms in which one of the heteroatoms in the ring is a nitrogen. A heteroaryl may consist of a single ring or 2 or 3 fused rings. Examples of heteroaryls include, but are not limited to, 6-membered ring substituents such as pyridinyl, pyrazinyl, pyrimidinyl and pyridazinyl; 5-membered heteroaryls such as triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, thiadiazolyl, isothiazolyl, and pyrazolyl; 6/5-membered fused ring substituents such as indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl (e.g., [1,2,4]triazolo[1,5-a]pyridin-2-yl), and anthranilyl; and 6/6-membered fused ring substituents such as quinolinyl, isoquinolinyl, cinnolinyl, quinazolinyl, oxochromanyl, and 1,4-benzoxazinyl.

It is to be understood that the heteroaryl may be optionally fused to a cycloalkyl group, or to a heterocycloalkyl group, as defined herein.

The heteroaryl substituent may be attached to the dihydropyrrolopyridine core of the compounds of the present invention via a nitrogen atom having the appropriate valence, or via any carbon atom. The heteroaryl moiety may be optionally substituted with one or more substituents at a nitrogen atom having the appropriate valence, or at any available carbon atom.

The terms "optionally substituted (5- to 10-membered) heteroaryl", "optionally substituted (5- to 6-membered)heteroaryl" and "optionally substituted (5- to 6-membered) nitrogen-containing heteroaryl" refer to a (5- to 10-membered)heteroaryl, a (5- to 6-membered)heteroaryl, and a (5- to 6-membered)nitrogen-containing heteroaryl, as defined above, in which one or more hydrogen atoms are replaced, where chemically permissible, by a substituent selected from the group consisting of halogen, oxo, cyano, hydroxy, —SF$_5$, nitro, —(C$_1$-C$_6$)alkyl, —(C$_1$-C$_6$)alkoxy, —N(R$^4$)(R$^5$), —N(R$^4$)(C(=O)R$^5$), —N(R$^4$)C(=O)—OR$^5$, —C(=O)—N(R$^4$)(R$^5$), —O—C(=O)—N(R$^4$)(R$^5$), —C(=O)—R$^4$, —C(=O)—OR$^4$, and optionally substituted (C$_3$-C$_8$)cycloalkyl, in which R$^3$ and R$^4$ are each independently selected from hydrogen and optionally substituted (C$_1$-C$_6$)alkyl.

The substituent can be attached to the heteroaryl moiety at any available carbon atom or to a heteroatom when the heteroatom is nitrogen having the appropriate valence.

"halo" or "halogen", as used herein, refers to a chlorine, fluorine, bromine, or iodine atom.

"hydroxy" or "hydroxyl", as used herein, means an —OH group.

"cyano", as used herein, means a —CN group, which also may be depicted:

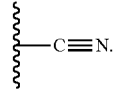

"nitro", as used herein, means an —NO$_2$ group.

"oxo", as used herein, means a =O moiety. When an oxo is substituted on a carbon atom, they together form a carbonyl moiety [—C(=O)—]. When an oxo is substituted on a sulfur atom, they together form a sulfoxide moiety [—S(=O)—]; when two oxo groups are substituted on a sulfur atom, they together form a sulfonyl moiety [—S(=O)$_2$—].

"Optionally substituted", as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., —CH$_3$) is optionally substituted, then up to 3 hydrogen atoms on the carbon atom can be replaced with substituent groups.

"Patient" refers to warm-blooded animals such as, for example, pigs, cows, chickens, horses, guinea pigs, mice, rats, gerbils, cats, rabbits, dogs, monkeys, chimpanzees, and humans.

"Pharmaceutically acceptable" indicates that the substance or composition must be compatible, chemically and/or toxicologically, with the other ingredients comprising a formulation, and/or the mammal being treated therewith.

The term "therapeutically effective amount" as used herein refers to that amount of the compound (including an N-oxide thereof or a pharmaceutically acceptable salt of the compound or the N-oxide) being administered which will relieve to some extent one or more of the symptoms of the disorder being treated. In reference to the treatment of an M4-mediated disorder (e.g., Alzheimer's Disease or schizophrenia), a therapeutically effective amount refers to that amount which has the effect of relieving to some extent (or, for example, eliminating) one or more symptoms associated with the M4-mediated disorder (e.g., positive, negative, or cognitive symptom of schizophrenia; or psychotic symptom of Alzheimer's Disease).

The term "treating", as used herein, unless otherwise indicated, means reversing, alleviating, inhibiting the progress of, or preventing the disorder or condition to which such term applies, or one or more symptoms of such disorder or condition.

The term "treatment", as used herein, unless otherwise indicated, refers to the act of treating as "treating" is defined herein. The term "treating" also includes adjuvant and neo-adjuvant treatment of a subject.

"Isoform" means any of several different forms of the same protein.

"Isozyme" or "isoenzyme" means a closely related variant of an enzyme that differs in amino acid sequence but catalyzes the same chemical reaction.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms), unless otherwise specified or otherwise implicit from the context. For example, as shown in Formula I below, one $R^1$ (wherein a is 1, 2 or 3) may be bonded, valency permitting, to any one of the ring carbon atoms of the 6-membered ring, and $R^2$ (wherein b is 1, 2, 3, or 4) may be bonded, valency permitting, to any one of the ring carbon atoms of the 5-membered ring as shown below:

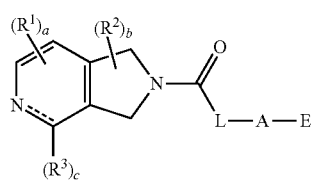

(I)

When a substituted or optionally substituted moiety is described without indicating the atom via which such moiety is bonded to a substituent, then the substituent may be bonded via any appropriate atom in such moiety. For example in an optionally substituted (5- to 10-membered) heteroaryl, a substituent on the heteroaryl can be bonded to any carbon atom on the heteroaryl part or on the heteroatom of the heteroaryl, valency permitting. Combinations of substituents and/or variables are permissible only if such combinations result in stable compounds.

This specification uses the terms "substituent," "radical," and "group" interchangeably.

If substituents are described as being "independently selected" from a group, each instance of a substituent is selected independent of any other. Each substituent therefore may be identical to or different from the other substituent(s).

As used herein the term "Formula I", "Formula Ia" and "Formula Ib" may be hereinafter referred to as a "compound(s) of the invention." Such terms are also defined to include all forms of the compounds of the invention including, but not limited to, hydrates, solvates, isomers (including for example rotational stereoisomers), crystalline and non-crystalline forms, isomorphs, polymorphs, metabolites, prodrugs thereof. For example, the compounds of the invention, or pharmaceutically acceptable salts thereof, may exist in unsolvated and solvated forms with pharmaceutically acceptable solvents such as water, ethanol and the like. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. In general, the solvated forms are considered equivalent to the unsolvated forms for the purposes of the present invention.

The compounds of the invention may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975). Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention may exist as geometric isomers, wherein the compounds have asymmetric carbon atoms, and thus may exist as two or more stereoisomeric forms. The present invention includes all the individual stereoisomers and geometric isomers of the compounds of the invention and mixtures thereof. Individual enantiomers can be obtained by chiral separation or using the relevant enantiomer in the synthesis. The carbon-carbon bonds of the compounds of the invention may be depicted herein using a solid line (-), a solid wedge (⬛), or a dotted wedge (⋯⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry may be marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, atropisomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

In some embodiments, the compounds of the present invention may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the present invention may also exist as an N-oxide thereof, or a pharmaceutically acceptable salt of the compound or N-oxide.

As it is known to the person skilled in the art, amine compounds (i.e., those comprising one or more nitrogen atoms), for example tertiary amines, can form N-oxides (also known as amine oxides or amine N-oxides). An N-oxide has the formula of $(R^{100}R^{200}R^{300})N^+$—$O^-$ wherein the parent amine $(R^{100}R^{200}R^{300})N$ can be for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100}R^{200}R^{300})N$ together forms 1-alkylpiperidine, 1-alkylpyrrolidine, 1-benzylpyrrolidine, or pyridine]. For instance, an imine nitrogen, especially heterocyclic or heteroaromatic imine nitrogen, or pyridine-type nitrogen

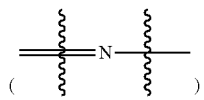

atom [such as a nitrogen atom in pyridine, pyridazine, or pyrazine], can be N-oxidized to form the N-oxide comprising the group

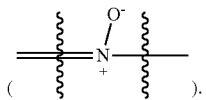

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

As noted above, the compounds of the invention (or N-oxides thereof) may exist in the form of pharmaceutically acceptable salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the present invention with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as, but not limited to, hydrochloric, hydrobromic, hydrofluoric, boric, fluoroboric, phosphoric, meta-phosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylamino-sulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanol-amine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of the invention are known to one of skill in the art.

Compounds of the invention may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$N$^+$) or non-ionic (such as —N$^-$N$^+$(CH$_3$)$_3$) polar head group. For more information, see Crystals and the Polarizing Microscope by N. H. Hartshorne and A. Stuart, 4$^{th}$ Edition (Edward Arnold, 1970).

The invention also relates to prodrugs of the compounds of the present invention. Thus certain derivatives of compounds of the invention which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of the invention may themselves act as prodrugs of other compounds of the invention.

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

Also included within the scope of the invention are metabolites of compounds of the invention, that is, compounds formed in vivo upon administration of the drug.

The present invention also includes all pharmaceutically acceptable isotopically labeled compounds, which are identical to those recited herein, wherein one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of the present invention, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron-emitting isotopes, such as $^{11}$C, $^{15}$F, $^{18}$F, $^{15}$O and $^{13}$N, can be useful in positron emission tomography (PET) studies for examining substrate receptor occupancy. Isotopically labeled compounds of the present invention can generally be prepared by conventional techniques known to those skilled in the art or by processes analogous to those described in the accompanying Schemes and/or in the Examples and Preparations using an appropriate isotopically labeled reagent in place of the non-labeled reagent previously employed.

Pharmaceutically acceptable solvates in accordance with the invention include those wherein the solvent of crystallization may be isotopically substituted, e.g., D$_2$O, acetone-d$_6$, or DMSO-d$_6$. Compounds of the invention, which include compounds exemplified in Examples 1-67 described below, include isotopically labeled versions of these compounds, such as, but not limited to, the deuterated and tritiated isotopes and all other isotopes discussed above.

In certain embodiments, the present invention is directed to novel, selective, radiolabelled M4 activators which are useful for imaging and quantifying distribution of M4 compounds in tissues (e.g., brain), using positron-emission tomography (PET).

Compounds

The compounds of Formula I, as described above, contain a dihydro-pyrrolo-pyridine core wherein the core is optionally substituted on the pyridine ring with up to three R$^1$ and one R$^3$; optionally substituted on the pyrrole ring with up to four R$^2$; and L, A, and E are as defined above, and hereinafter.

In one embodiment, in Formula I as described above, each R$^1$, when present, is selected from the group consisting of halogen, optionally substituted (C$_1$-C$_6$)alkyl, optionally substituted (C$_1$-C$_6$)alkoxy, and —N(R$^4$)(R$^5$); and a is an integer selected from 1, 2 and 3.

In certain embodiments, R$^1$ is a halogen, and the halogen is selected from chloro and fluoro.

In certain embodiments, R$^1$ is an optionally substituted (C$_1$-C$_6$)alkyl, and the (C$_1$-C$_6$)alkyl is selected from methyl and ethyl. Examples of optionally substituted (C$_1$-C$_6$)alkyl include, but are not limited to, fluoromethyl, difluoromethyl, trifluoromethyl, fluoroethyl, difluoroethyl, trifluoroethyl, methanol, and methoxymethyl. In certain embodiments R$^1$ is methyl.

In certain embodiments, R$^1$ is an optionally substituted (C$_1$-C$_6$)alkoxy, and the (C$_1$-C$_6$)alkoxy is selected from methoxy and ethoxy. Examples of optionally substituted (C$_1$-C$_6$)alkoxy include, but are not limited to, fluoromethoxy, difluoromethoxy, trifluoromethoxy, fluoroethoxy, difluoroethoxy and trifluoroethoxy.

It is to be understood that any of the above-mentioned subgenuses (embodiments) of $R^1$ can be combined together with any of the subgenuses for $R^2$, $R^3$, L, A, and E as described above and hereinafter.

In certain other embodiments, in Formula I as described above, each $R^2$, when present, is an optionally substituted ($C_1$-$C_6$)alkyl; and b is an integer selected from 0 and 1.

In certain embodiments, b is 1 and the optionally substituted ($C_1$-$C_6$)alkyl is methyl.

In certain embodiments, b is 0 (i.e., $R^2$ is absent).

It is to be understood that any of the above-mentioned subgenuses (embodiments) of $R^2$ can be combined together with any of the subgenuses for $R^1$, $R^3$, L, A, and E as described above and hereinafter.

In certain other embodiments, in Formula I as described above, $R^3$, when present, is oxo, an optionally substituted ($C_1$-$C_6$)alkyl, an optionally substituted ($C_1$-$C_6$)alkoxy; and c is an integer selected from 0 and 1, provided that when $R^3$ is oxo ===== ==== is a single bond, or when c is 0 then $R^3$ is absent and ===== 1 is a double bond.

In certain embodiments, c is 1, $R^3$ is oxo and ===== is a single bond.

In certain embodiments, c is 1, and $R^3$ is an optionally substituted ($C_1$-$C_6$)alkyl and ===== is a double bond. In certain embodiments, $R^3$ is an optionally substituted ($C_1$-$C_6$)alkyl selected from the group consisting of —($CH_2$)N($CH_3$)$_2$, —CH($F_2$), and —($CH_2$)O($CH_3$) and ===== is a double bond.

In certain embodiments, c is 1, and $R^3$ is an optionally substituted ($C_1$-$C_6$)alkoxy and ===== is a double bond. In certain embodiments, $R^3$ is an optionally substituted ($C_1$-$C_6$)alkoxy selected from the group consisting of —$OCH_3$, and —OCH($F_2$) and ===== is a double bond, In certain other embodiments, c is 1, and $R^3$ is —N($R^4$)($R^5$), wherein $R^4$ and $R^5$ are each independently selected from the group consisting of hydrogen and optionally substituted ($C_1$-$C_6$)alkyl and ===== is a double bond. In certain embodiments, c is 1, and $R^3$ is —N($R^4$)($R^5$), wherein $R^4$ and $R^5$ are each hydrogen and ===== is a double bond. In certain embodiments, c is 1, and $R^3$ is —N($R^4$)($R^5$), wherein $R^4$ and $R^5$ are each methyl and ===== is a double bond. In certain embodiments, c is 1, and $R^3$ is —N($R^4$)($R^5$), wherein one of $R^4$ and $R^5$ is hydrogen and the other is methyl and ===== is a double bond. In certain embodiments, c is 1, and $R^3$ is —N($R^4$)($R^5$), wherein one of $R^4$ and $R^5$ is hydrogen and the other is cyclopropylmethyl and ===== is a double bond.

In certain embodiments, c is 0 (i.e., $R^3$ is absent) and ===== is a double bond.

It is to be understood that any of the above-mentioned subgenuses (embodiments) of $R^3$ can be combined together with any of the subgenuses for $R^1$, $R^2$, L, A, and E as described above and hereinafter.

In certain other embodiments, in Formula I as described above, L is oxygen.

In certain embodiments, in Formula I as described above, L is —($CH_2$)$_m$ and m is an integer selected from 0, 1 and 2.

In certain embodiments, L is —($CH_2$)$_m$— and m is 2.
In certain embodiments, L is —($CH_2$)$_m$— and m is 1.
In certain embodiments, L is —($CH_2$)$_m$— and m is 0.

It is to be understood that any of the above-mentioned subgenuses (embodiments) of L can be combined together with any of the subgenuses for $R^1$, $R^2$, $R^3$, A, and E as described above and hereinafter.

In certain other embodiments, in Formula I as described above, A is a ($C_3$-$C_6$)cycloalkyl selected from the group consisting of cyclopropyl, cyclobutyl, cyclopentyl, and cyclohexyl, wherein said cycloalkyl is optionally substituted with one to three substituents independently selected from the group consisting of halogen, cyano, —N($R^4$)($R^5$), optionally substituted ($C_1$-$C_6$)alkyl, and optionally substituted ($C_1$-$C_6$)alkoxy.

In certain embodiments A is cyclopropyl.

In certain other embodiments, A is a (4- to 6-membered) heterocycloalkyl selected from the group consisting of azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, imidazolidinyl, pyrrolidinyl, piperidinyl, piperazinyl, oxazolidinyl, thiazolidinyl, pyrazolidinyl, tetrahydropyranyl, tetrahydrothiazinyl, tetrahydrothiadiazinyl, tetrahydrooxazolyl, oxetanyl, dioxetanyl, dioxolanyl, dioxanyl, oxazinyl, and oxathiazinyl, wherein said heterocycloalkyl is optionally substituted with one to three substituents independently selected from the group consisting of halogen, cyano, —N($R^4$)($R^5$), optionally substituted ($C_1$-$C_6$)alkyl, and optionally substituted ($C_1$-$C_6$)alkoxy.

In certain embodiments A is a (4- to 6-membered)heterocycloalkyl and the heterocycloalkyl is azetidinyl.

It is to be understood that any of the above-mentioned subgenuses (embodiments) of A can be combined together with any of the subgenuses for $R^1$, $R^2$, $R^3$, L, and E as described above and hereinafter.

In certain embodiments, in Formula I as described above, E is a (5- to 10-membered)heteroaryl selected from the group consisting of triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, thiadiazolyl, isothiazolyl, pyrazolyl, pyridinyl, pyrazinyl, pyrimidinyl, pyridazinyl, indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl, anthranilyl, quinolinyl, isoquinolinyl, cinnolinyl, quinazolinyl, oxochromanyl, and 1,4-benzoxazinyl, wherein said heteroaryl is optionally substituted with one to three substituents independently selected from the group consisting of halogen, cyano, —N($R^4$)($R^5$), optionally substituted ($C_1$-$C_6$)alkyl, and optionally substituted ($C_1$-$C_6$) alkoxy.

In certain other embodiments, E is a (5- to 6-membered) nitrogen-containing heteroaryl selected from the group consisting of triazolyl, thiadiazolyl, imidazolyl, pyrazolyl, pyridinyl, pyrazinyl, pyrimidinyl, and pyridazinyl, wherein said nitrogen-containing heteroaryl is optionally substituted with one to three substituents independently selected from the group consisting of halogen, cyano, —N($R^4$)($R^5$), optionally substituted ($C_1$-$C_6$)alkyl, and optionally substituted ($C_1$-$C_6$)alkoxy.

In certain other embodiments, E is pyridinyl optionally substituted with one to two substituents independently selected from the group consisting of halogen, cyano, —N($R^4$)($R^5$), optionally substituted ($C_1$-$C_6$)alkyl, and optionally substituted ($C_1$-$C_6$)alkoxy.

In certain other embodiments, E is pyrimidinyl optionally substituted with one to two substituents independently selected from the group consisting of halogen, cyano, —N($R^4$)($R^5$), optionally substituted ($C_1$-$C_6$)alkyl, and optionally substituted ($C_1$-$C_6$)alkoxy.

In certain other embodiments, E is pyrazolyl optionally substituted with one to two substituents independently selected from the group consisting of halogen, cyano, —N(R⁴)(R⁵), optionally substituted (C₁-C₆)alkyl, and optionally substituted (C₁-C₆)alkoxy.

In certain other embodiments, E is thiadiazolyl optionally substituted with one to two substituents independently selected from the group consisting of halogen, cyano, —N(R⁴)(R⁵), optionally substituted (C₁-C₆)alkyl, and optionally substituted (C₁-C₆)alkoxy.

In certain other embodiments, E is a (C₃-C₁₂)cycloalkyl, wherein said cycloalkyl is cyclopropyl.

In certain other embodiments, E is a (C₃-C₁₂)cycloalkyl, wherein said cycloalkyl is dihydrocyclopentapyridinyl.

In certain other embodiments, E is a (C₃-C₁₂)cycloalkyl, wherein said cycloalkyl is dihydroindenyl.

In certain other embodiments, E is a (5- to 6-membered) heterocycloalkyl, wherein said heterocycloalkyl is tetrahydrofuranyl.

In certain other embodiments, E is a (C₆-C₁₂) aryl, wherein said aryl is phenyl.

It is to be understood that any of the above-mentioned subgenuses (embodiments) of E can be combined together with any of the subgenuses for R¹, R², R³, L, and A as described above and hereinafter.

In certain other embodiments, the present invention is a compound of Formula Ia:

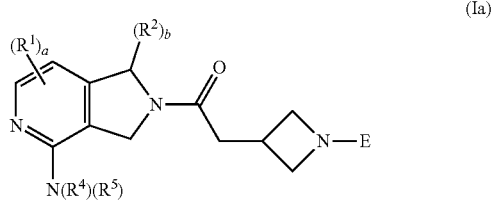

(Ia)

or an N-oxide thereof, or a pharmaceutically acceptable salt of the compound or the N-oxide, wherein:
each R¹ is independently selected from the group consisting of halogen, optionally substituted (C₁-C₆)alkyl, and optionally substituted (C₁-C₆)alkoxy;
a is an integer selected from 1, 2 and 3;
R², when present, is an optionally substituted (C₁-C₆) alkyl;
b is an integer selected from 0 and 1;
R⁴ and R⁵ are each independently selected from hydrogen and optionally substituted (C₁-C₆)alkyl; and
E is a (5- to 6-membered)heteroaryl, wherein said heteroaryl is optionally substituted with one to three substituents independently selected from the group consisting of halogen, cyano, optionally substituted (C₁-C₆)alkyl, optionally substituted (C₁-C₆)alkoxy, and —N(R⁴)(R⁵), wherein R⁴ and R⁵ at each occurrence are each independently selected from hydrogen and optionally substituted (C₁-C₆) alkyl.

In another embodiment, in Formula Ia, as described above, b is 1 and R² is methyl.

In another embodiment, b is 0 (i.e., R² is absent).

In another embodiment, in Formula Ia as described above, E is a (5- to 6-membered)nitrogen-containing heteroaryl selected from the group consisting of pyrazolyl, thiazolyl, thiadiazolyl, pyridinyl, pyrimidinyl, and pyrazinyl, wherein said nitrogen-containing heteroaryl is optionally substituted with one to three substituents independently selected from the group consisting of halogen, cyano, —N(R⁴)(R⁵), optionally substituted (C₁-C₆)alkyl, and optionally substituted (C₁-C₆)alkoxy.

In certain other embodiments, E is pyridinyl optionally substituted with one to two substituents independently selected from the group consisting of halogen, cyano, —N(R⁴)(R⁵), optionally substituted (C₁-C₆)alkyl, and optionally substituted (C₁-C₆)alkoxy.

In certain other embodiments, E is pyrimidinyl optionally substituted with one to two substituents independently selected from the group consisting of halogen, cyano, —N(R⁴)(R⁵), optionally substituted (C₁-C₆)alkyl, and optionally substituted (C₁-C₆)alkoxy.

In certain other embodiments, E is pyrazolyl optionally substituted with one to two substituents independently selected from the group consisting of halogen, cyano, —N(R⁴)(R⁵), optionally substituted (C₁-C₆)alkyl, and optionally substituted (C₁-C₆)alkoxy.

In certain other embodiments, E is thiadiazolyl optionally substituted with one to two substituents independently selected from the group consisting of halogen, cyano, —N(R⁴)(R⁵), optionally substituted (C₁-C₆)alkyl, and optionally substituted (C₁-C₆)alkoxy.

In certain other embodiments, the present invention is a compound of Formula Ib:

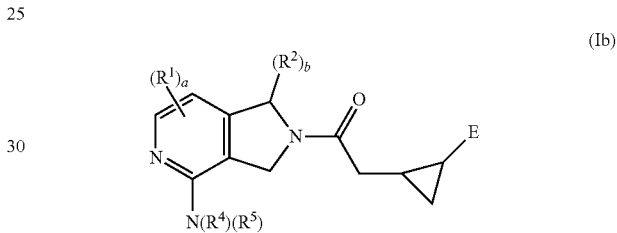

(Ib)

or an N-oxide thereof, or a pharmaceutically acceptable salt of the compound or the N-oxide, wherein:
each R¹ is independently selected from the group consisting of halogen, optionally substituted (C₁-C₆)alkyl, and optionally substituted (C₁-C₆)alkoxy;
a is an integer selected from 1, 2 and 3;
R², when present, is an optionally substituted (C₁-C₆) alkyl;
b is an integer selected from 0 and 1;
R⁴ and R⁵ at each occurrence are each independently selected from hydrogen and optionally substituted (C₁-C₆) alkyl; and
E is a (5- to 6-membered)heteroaryl, wherein said heteroaryl is optionally substituted with one to three substituents independently selected from the group consisting of halogen, cyano, hydroxy, optionally substituted (C₁-C₆) alkyl, optionally substituted (C₁-C₆)alkoxy, and —N(R⁴) (R⁵), wherein R⁴ and R⁵ at each occurrence are each independently selected from hydrogen and optionally substituted (C₁-C₆)alkyl.

In another embodiment, in Formula Ib, as described above, b is 1 and R² is methyl.

In another embodiment, b is 0 (i.e., R² is absent).

In another embodiment, in Formula Ib as described above, E is a (5- to 6-membered)nitrogen-containing heteroaryl selected from the group consisting of pyrazolyl, thiazolyl, thiadiazolyl, pyridinyl, pyrimidinyl, and pyrazinyl, wherein said nitrogen-containing heteroaryl is optionally substituted with one to three substituents independently selected from the group consisting of halogen, cyano, —N(R⁴)(R⁵), optionally substituted (C₁-C₆)alkyl, and optionally substituted (C₁-C₆)alkoxy.

In certain other embodiments, E is pyridinyl optionally substituted with one to two substituents independently selected from the group consisting of halogen, cyano, —N(R⁴)(R⁵), optionally substituted ($C_1$-$C_6$)alkyl, and optionally substituted ($C_1$-$C_6$)alkoxy.

In certain other embodiments, E is pyrimidinyl optionally substituted with one to two substituents independently selected from the group consisting of halogen, cyano, —N(R⁴)(R⁵), optionally substituted ($C_1$-$C_6$)alkyl, and optionally substituted ($C_1$-$C_6$)alkoxy.

In certain other embodiments, E is pyrazolyl optionally substituted with one to two substituents independently selected from the group consisting of halogen, cyano, —N(R⁴)(R⁵), optionally substituted ($C_1$-$C_6$)alkyl, and optionally substituted ($C_1$-$C_6$)alkoxy.

In certain other embodiments, E is thiadiazolyl optionally substituted with one to two substituents independently selected from the group consisting of halogen, cyano, —N(R⁴)(R⁵), optionally substituted ($C_1$-$C_6$)alkyl, and optionally substituted ($C_1$-$C_6$)alkoxy.

In certain other embodiments, the present invention is directed to a compound selected from the group consisting of:

5,6,7-trimethyl-2-{[1-(pyridin-3-yl)azetidin-3-yl]acetyl}-1,2,3,5-tetrahydro-4H-pyrrolo[3,4-c]pyridin-4-one;

1-[6,7-dimethyl-4-(methylamino)-1,3-dihydro-2H-pyrrolo[3,4-c]pyridin-2-yl]-2-[1-(1,2,4-thiadiazol-5-yl)azetidin-3-yl]ethanone;

2-{1-[2-(difluoromethoxy)pyridin-4-yl]azetidin-3-yl}-1-[6,7-dimethyl-4-(methylamino)-1,3-dihydro-2H-pyrrolo[3,4-c]pyridin-2-yl]ethanone;

1-[6,7-dimethyl-4-(methylamino)-1,3-dihydro-2H-pyrrolo[3,4-c]pyridin-2-yl]-2-[1-(pyridin-3-yl)azetidin-3-yl]ethanone;

1-(pyridin-3-yl)azetidin-3-yl 6,7-dimethyl-4-(methylamino)-1,3-dihydro-2H-pyrrolo[3,4-c]pyridine-2-carboxylate;

6,7-dihydro-5H-cyclopenta[b]pyridin-6-yl 6,7-dimethyl-4-(methylamino)-1,3-dihydro-2H-pyrrolo[3,4-c]pyridine-2-carboxylate;

1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone;

1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone;

1-[6,7-dimethyl-4-(methylamino)-1,3-dihydro-2H-pyrrolo[3,4-c]pyridin-2-yl]-2-[trans-2-(pyridin-3-yl)cyclopropyl]ethanone;

2-[1-(pyridin-3-yl)azetidin-3-yl]-1-(4,6,7-trimethyl-1,3-dihydro-2H-pyrrolo[3,4-c]pyridin-2-yl)ethanone;

1-[6,7-dimethyl-4-(1-methyl-1H-pyrazol-4-yl)-1,3-dihydro-2H-pyrrolo[3,4-c]pyridin-2-yl]-2-[1-(pyridin-3-yl)azetidin-3-yl]ethanone;

1-{4-[(dimethylamino)methyl]-6,7-dimethyl-1,3-dihydro-2H-pyrrolo[3,4-c]pyridin-2-yl}-2-[1-(pyridin-3-yl)azetidin-3-yl]ethanone;

1-[6,7-dimethyl-4-(methylamino)-1,3-dihydro-2H-pyrrolo[3,4-c]pyridin-2-yl]-2-[trans-2-(6-fluoropyridin-3-yl)cyclopropyl]ethanone;

1-[4-(dimethylamino)-6,7-dimethyl-1,3-dihydro-2H-pyrrolo[3,4-c]pyridin-2-yl]-2-[1-(pyridin-3-yl)azetidin-3-yl]ethanone;

1-[4-(difluoromethyl)-6,7-dimethyl-1,3-dihydro-2H-pyrrolo[3,4-c]pyridin-2-yl]-2-[1-(pyridin-3-yl)azetidin-3-yl]ethanone;

1-[6,7-dimethyl-4-(methylamino)-1,3-dihydro-2H-pyrrolo[3,4-c]pyridin-2-yl]-2-[1-(pyrimidin-5-yl)azetidin-3-yl]ethanone;

1-[4-(dimethylamino)-6,7-dimethyl-1,3-dihydro-2H-pyrrolo[3,4-c]pyridin-2-yl]-2-[1-(pyrimidin-5-yl)azetidin-3-yl]ethanone;

6,7-dimethyl-2-{[1-(pyridin-3-yl)azetidin-3-yl]acetyl}-1,2,3,5-tetrahydro-4H-pyrrolo[3,4-c]pyridin-4-one;

1-{4-[(cyclopropylmethyl)amino]-6,7-dimethyl-1,3-dihydro-2H-pyrrolo[3,4-c]pyridin-2-yl}-2-[1-(pyrimidin-4-yl)azetidin-3-yl]ethanone;

1-[6,7-dimethyl-4-(methylamino)-1,3-dihydro-2H-pyrrolo[3,4-c]pyridin-2-yl]-2-[1-(pyrimidin-4-yl)azetidin-3-yl]ethanone;

2-(2,3-dihydro-1H-inden-2-yl)-1-[6,7-dimethyl-4-(methylamino)-1,3-dihydro-2H-pyrrolo[3,4-c]pyridin-2-yl]ethanone;

5,6,7-trimethyl-2-({1-[2-(trifluoromethyl)pyridin-4-yl]azetidin-3-yl}acetyl)-1,2,3,5-tetrahydro-4H-pyrrolo[3,4-c]pyridin-4-one;

5,6,7-trimethyl-2-{[trans-2-(pyridin-3-yl)cyclopropyl]acetyl}-1,2,3,5-tetrahydro-4H-pyrrolo[3,4-c]pyridin-4-one;

1-[6,7-dimethyl-4-(methylamino)-1,3-dihydro-2H-pyrrolo[3,4-c]pyridin-2-yl]-2-[trans-2-(pyrimidin-5-yl)cyclopropyl]ethanone;

1-[6,7-dimethyl-4-(methylamino)-1,3-dihydro-2H-pyrrolo[3,4-c]pyridin-2-yl]-2-[trans-2-(pyrimidin-5-yl)cyclopropyl]ethanone;

4-{3-[6,7-dimethyl-4-(methylamino)-1,3-dihydro-2H-pyrrolo[3,4-c]pyridin-2-yl]-3-oxopropyl}benzonitrile;

1-[6,7-dimethyl-4-(methylamino)-1,3-dihydro-2H-pyrrolo[3,4-c]pyridin-2-yl]-3-(4-methoxyphenyl)propan-1-one;

2-[trans-2-(6-chloropyridin-3-yl)cyclopropyl]-1-[6,7-dimethyl-4-(methylamino)-1,3-dihydro-2H-pyrrolo[3,4-c]pyridin-2-yl]ethanone;

1-[6,7-dimethyl-4-(methylamino)-1,3-dihydro-2H-pyrrolo[3,4-c]pyridin-2-yl]-2-{1-[2-(trifluoromethyl)pyridin-4-yl]azetidin-3-yl}ethanone;

1-[6,7-dimethyl-4-(methylamino)-1,3-dihydro-2H-pyrrolo[3,4-c]pyridin-2-yl]-2-[1-(2-methylpyridin-4-yl)azetidin-3-yl]ethanone;

4-(3-{2-[6,7-dimethyl-4-(methylamino)-1,3-dihydro-2H-pyrrolo[3,4-c]pyridin-2-yl]-2-oxoethyl}azetidin-1-yl)pyridine-2-carbonitrile;

1-[6,7-dimethyl-4-(methylamino)-1,3-dihydro-2H-pyrrolo[3,4-c]pyridin-2-yl]-2-[1-(1,3,4-thiadiazol-2-yl)azetidin-3-yl]ethanone;

1-[6,7-dimethyl-4-(methylamino)-1,3-dihydro-2H-pyrrolo[3,4-c]pyridin-2-yl]-3-(1H-pyrazol-4-yl)propan-1-one;

1-[4-(difluoromethyl)-6,7-dimethyl-1,3-dihydro-2H-pyrrolo[3,4-c]pyridin-2-yl]-2-{1-[2-(difluoromethyl)pyridin-4-yl]azetidin-3-yl}ethanone;

1-[6,7-dimethyl-4-(methylamino)-1,3-dihydro-2H-pyrrolo[3,4-c]pyridin-2-yl]-2-[trans-2-(4-fluorophenyl)cyclopropyl]ethanone;

2-{1-[2-(trifluoromethyl)pyridin-4-yl]azetidin-3-yl}-1-[1,6,7-trimethyl-4-(methylamino)-1,3-dihydro-2H-pyrrolo[3,4-c]pyridin-2-yl]ethanone;

2-{1-[2-(trifluoromethyl)pyridin-4-yl]azetidin-3-yl}-1-[1,6,7-trimethyl-4-(methylamino)-1,3-dihydro-2H-pyrrolo[3,4-c]pyridin-2-yl]ethanone;

1-[6,7-dimethyl-4-(methylamino)-1,3-dihydro-2H-pyrrolo[3,4-c]pyridin-2-yl]-2-[trans-2-(6-methylpyridin-3-yl)cyclopropyl]ethanone;

1-[6,7-dimethyl-4-(methylamino)-1,3-dihydro-2H-pyrrolo[3,4-c]pyridin-2-yl]-2-[trans-2-(6-methylpyridin-3-yl)cyclopropyl]ethanone;
[6,7-dimethyl-4-(methylamino)-1,3-dihydro-2H-pyrrolo[3,4-c]pyridin-2-yl](1-methyl-1H-pyrazol-4-yl)methanone;
2-{1-[2-(difluoromethoxy)pyridin-4-yl]azetidin-3-yl}-1-[1,6,7-trimethyl-4-(methylamino)-1,3-dihydro-2H-pyrrolo[3,4-c]pyridin-2-yl]ethanone;
1-[6,7-dimethyl-4-(methylamino)-1,3-dihydro-2H-pyrrolo[3,4-c]pyridin-2-yl]-2-[1-(6-fluoropyridin-3-yl)azetidin-3-yl]ethanone;
1-(6,7-dimethyl-1,3-dihydro-2H-pyrrolo[3,4-c]pyridin-2-yl)-2-[1-(pyridin-3-yl)azetidin-3-yl]ethanone;
1-(4-methoxy-6,7-dimethyl-1,3-dihydro-2H-pyrrolo[3,4-c]pyridin-2-yl)-2-[1-(pyridin-3-yl)azetidin-3-yl]ethanone;
1-[4-(methoxymethyl)-6,7-dimethyl-1,3-dihydro-2H-pyrrolo[3,4-c]pyridin-2-yl]-2-[1-(pyridin-3-yl)azetidin-3-yl]ethanone;
1-(4-methoxy-6,7-dimethyl-1,3-dihydro-2H-pyrrolo[3,4-c]pyridin-2-yl)-2-[1-(pyrimidin-5-yl)azetidin-3-yl]ethanone;
1-[4-(difluoromethoxy)-6,7-dimethyl-1,3-dihydro-2H-pyrrolo[3,4-c]pyridin-2-yl]-2-[1-(pyrimidin-5-yl)azetidin-3-yl]ethanone;
1-[6,7-dimethyl-4-(methylamino)-1,3-dihydro-2H-pyrrolo[3,4-c]pyridin-2-yl]-2-(5-fluoro-2,3-dihydro-1H-inden-2-yl)ethanone;
cyclopropyl[6,7-dimethyl-4-(methylamino)-1,3-dihydro-2H-pyrrolo[3,4-c]pyridin-2-yl]methanone;
[6,7-dimethyl-4-(methylamino)-1,3-dihydro-2H-pyrrolo[3,4-c]pyridin-2-yl][(3R)-tetrahydrofuran-3-yl]methanone; and an N-oxide thereof, or a pharmaceutically acceptable salt thereof or pharmaceutically acceptable salt of the N-oxide.

In certain other embodiments, the present invention is directed to the use of the compounds, or N-oxide, or pharmaceutically acceptable salt of any one the compounds of the present invention in the treatment of an M4-mediated (or M4-associated) disease or disorder.

In certain other embodiments, the present invention is directed to a method for treating an M4-mediated (or M4-associated) disease or disorder in a patient, said method comprising administering to the patient a therapeutically effective amount of a compound, or N-oxide, or pharmaceutically acceptable salt of any one the compounds of the present invention.

In certain embodiments, the compounds of the present invention are M4 receptor agonists, wherein the compound has a binding affinity for and induces an effect on the M4 receptor absent the presence of a native ligand (e.g. acetylcholine).

In certain other embodiments, the compounds of the present invention are positive allosteric modulators (PAM) of the M4 receptor, wherein the compound has a binding affinity for and induces an effect on the receptor in the presence of a suboptimal concentration of native ligand (e.g., acetylcholine).

In another embodiment, the compounds of the present invention induce M4 agonist and M4 PAM activity.

In certain other embodiments, the present invention is directed to the use mentioned above wherein the M4-mediated (or M4-associated) disease or disorder is a disease or disorder selected from the group consisting of Alzheimer's Disease, schizophrenia, pain, addiction, a sleep disorder, a cognitive disorder (e.g. mild cognitive impairment, age-related mild cognitive impairment, and amnestic mild cognitive impairment), Parkinson's Disease, Huntington's Disease, dyskinesia, dry mouth, pulmonary hypertension, chronic obstructive pulmonary disease (COPD), asthma, urinary incontinence, glaucoma, Trisomy 21 (Down Syndrome), cerebral amyloid angiopathy, dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis.

In certain embodiments, the M4-mediated (or M4-associated) disease or disorder is a disease or disorder selected from the group consisting of Alzheimer's Disease, Parkinson's Disease, Huntington's Disease, schizophrenia, pain, addiction, and a sleep disorder.

The present invention also provides compositions (e.g., pharmaceutical compositions) comprising a novel compound of the present invention. Accordingly, in one embodiment, the invention provides a pharmaceutical composition comprising (a therapeutically effective amount of) a novel compound of the present invention and optionally comprising a pharmaceutically acceptable carrier. In one further embodiment, the invention provides a pharmaceutical composition comprising (a therapeutically effective amount of) a compound of the invention, optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

Pharmacology

The muscarinic acetylcholine receptor M4 (also known as muscarinic 4 or CHRM4) is a protein in humans that is encoded for the CHRM4 gene. M4 receptors are predominantly expressed in the brain. Key regions of the brain where M4 receptor expression occurs are the striatum, cortex, and hippocampus with the highest expression occurring in the striatum (approx. 46%) where M4 is the major muscarinic subtype. M4 is sporadically expressed in the periphery (e.g., testis, skin and colon).

M4 receptors are coupled to $G_{q/i}$ proteins and function as inhibitory autoreceptors in the striatum and midbrain (Zhang et al. 2002; Tzavara et al. 2004), and as postsynaptic modulatory receptors in the striatum, neocortex and hippocampus (Levy et al. 1991; Zhang et al. 1997). M4 receptors are also found presynaptically on glutamatergic synapses from cortex to striatum (Pancani, T., et al., "Allosteric activation of M4 improve behavioral and physiological alterations in early symptomatic YAC128 mice", Proceedings of the National Academy of the Sciences of the United States of America, 2015 Nov. 10; 112(45):14078-83), and on hippocampal glutamate neurons (where presynaptic M4 modulates glutamate release. The highest expression of M4 receptors is found in the striatum, M4 receptors also possess a regulatory effect on dopaminergic neurotransmission, and are coexpressed with D1 dopamine receptors in a subset of striatal medium spiny neurons which contain GABA as a major neurotransmitter (Bernard et al. 1992; Di Chiara et al. 1994; Ince et al. 1997).

It has been hypothesized that administration of a selective M4 agonist would provide antipsychotic activity for the treatment of schizophrenia (Felder et al. "Elucidating the Role of Muscarinic Receptors in Psychosis", Life Sci. 68:2605-2613, 2001). This belief was further supported by studies that demonstrated M4 receptors modulate the dynamics of dopaminergic and cholinergic neurotransmission and that a state of dopamine hyperfunctions results with a loss of M4 function (Tzavara et al., "M4 Muscarinic Receptors Regulate the Dynamics of Cholinergic and Dopaminergic Neurotransmission: relevance to the pathophysiology and treatment of related CNS pathologies" FASEB J. 18:1410-1412, 2004).

More recently, work conducted on the discovery of highly selective M4 positive allosteric modulators has helped support the hypothesis that selective activation of the M4 receptors may provide a novel approach for treating some of the symptoms associated with schizophrenia, and this work also raises the possibility that M4 selective modulators may also provide a treatment for other disorders where dopaminergic function is altered in the basal ganglia (e.g., Parkinson's Disease and dystonia) (Brady, et al., "Centrally Active Allosteric Potentiators of the M4 Muscarinic Acetylcholine Receptor Reverse Amphetamine-Induced Hyperlocomotor Activity in Rats", The Journal of Pharmacology and Experimental Therapeutics, Vol. 327, No. 3). Additional work with M1- and M4-selective modulators also suggests that selective activation of M4 receptors can provide viable therapeutic agents for safely and effectively treating Alzheimer's Disease and Schizophrenia.

The compounds of the present invention may also be useful for treating/alleviating the neuropsychiatric symptoms (i.e., behavioral symptoms) associated with Alzheimer's Disease and Schizophrenia (Foster, Daniel J. et. al., "Activation of M1 and M4 muscarinic receptors as potential treatments for Alzheimer's disease and schizophrenia", Neuropsychiatric Disease and Treatment, Volume 2014:10, pp. 183-191). These behavioral symptoms include, but are not limited to, agitation, anxiety, irritability, combativeness, disorientation, illusion, delusion, apathy, depression, disinhibition, aberrant motor and obsessive-compulsive behaviors, as well as sleep disorders (Dillon, Carol, et. al. "Behavioral symptoms related to cognitive impairment", Neuropsychiatric Disease and Treatment 2013:9 1443-1455). By treating/alleviating the above-mentioned behavioral symptoms, it is believed that the compounds of the present invention will also enhance cognition.

In view of the above, the compounds of the present invention may be useful for the treatment of schizophrenia and Alzheimer's Disease. The compounds of the present invention may also be useful for the treatment of Parkinson's Disease, Huntington's Disease, addiction, depression and epilepsy.

It is believed the M4 selective activators of the present invention may also have a wide range of other therapeutic applications for the treatment of conditions or diseases of the central nervous system which include neurologic, neurodegenerative and/or psychiatric disorders. Neurologic, neurodegenerative and/or psychiatric disorders include but are not limited to, (1) mood [affective] disorders; (2) neurotic, stress-related and somatoform disorders including anxiety disorders; (3) disorders comprising the symptom of cognitive deficiency in a mammal, including a human; (4) disorders comprising attention deficits, executive function deficits (working memory deficits), dysfunction of impulse control, extrapyramidal symptoms, disorders that are based on a malfunction of basal ganglia, hippocampus and prefrontal cortex; (5) behavioral and emotional disorders with onset usually occurring in childhood and adolescence; (6) disorders of psychological development; (7) systemic atrophies primarily affecting the central nervous system; (8) extrapyramidal and movement disorders; (9) behavioral syndromes associated with physiological disturbances and physical factors; (10) disorders of adult personality and behavior; (11) schizophrenia and other psychotic disorders; (12) mental and behavioral disorders due to psychoactive substance use; (13) sexual dysfunction comprising excessive sexual drive; (14) mental retardation; (15) factitious disorders, e.g., acute hallucinatory mania; (16) episodic and paroxysmal disorders, epilepsy; (17) narcolepsy; (18) dementia, and (19) amyotrophic lateral sclerosis.

Examples of mood [affective] disorders that can be treated according to the present invention include, but are not limited to, bipolar disorder I, hypomania (manic and mixed form), bipolar disorder II; depressive disorders such as single depressive episode or recurrent major depressive disorder, chronic depression, psychotic depression, minor depressive disorder, depressive disorder with postpartum onset, depressive disorders with psychotic symptoms; persistent mood [affective] disorders such as cyclothymia, dysthymia, euthymia; premenstrual syndrome (PMS) and premenstrual dysphoric disorder.

Examples of neurotic, stress-related and somatoform disorders that can be treated according to the present invention include, but are not limited to, anxiety disorders, social anxiety disorder, general anxiety disorder, panic disorder with or without agoraphobia, specific phobia, social phobia, chronic anxiety disorders; obsessive compulsive disorder; reaction to severe stress and adjustment disorders, such as post-traumatic stress disorder (PTSD), acute stress disorder; other neurotic disorders such as depersonalization-derealization syndrome.

The phrase "cognitive deficiency" as used herein and "disorders comprising the symptom of cognitive deficiency" refers to a subnormal functioning or a suboptimal functioning in one or more cognitive aspects such as memory, intellect, learning and logic ability, or attention and executive function (working memory) in a particular individual comparative to other individuals within the same general age population.

Examples of "disorders comprising the symptom of cognitive deficiency" that can be treated according to the present invention include, but are not limited to, cognitive deficits primarily but not exclusively related to amnesia, psychosis (schizophrenia), Parkinson's disease, Alzheimer's Disease, multi-infarct dementia, senile dementia, Lewis body dementia, stroke, frontotemporal dementia, progressive supranuclear palsy, Huntington's disease, HIV disease (HIV-associated dementia), cerebral trauma and drug abuse; mild cognitive disorder ADHD, Asperger's syndrome, and age-associated memory impairment; cognitive decline or delerium post-operative or in association with intensive care therapy.

Examples of disorders usually first diagnosed in infancy, childhood and adolescence that can be treated according to the present invention include, but are not limited to, hyperkinetic disorders including disturbance of activity and attention, attention deficit/hyperactivity disorder (ADHD), hyperkinetic conduct disorder; attention deficit disorder (ADD); conduct disorders, including but not limited to depressive conduct disorder; tic disorders including transient tic disorder, chronic motor or vocal tic disorder, combined vocal and multiple motor tic disorder (Gilles de la Tourette's syndrome), substance-induced tic disorders; autistic disorders; Batten disease, excessive masturbation, nail-biting, nose-picking and thumb-sucking.

Examples of disorders of psychological development that can be treated according to the present invention include, but are not limited to pervasive developmental disorders, including but not limited to Asperger's syndrome and Rett syndrome, autistic disorders, childhood autism and overactive disorder associated with mental retardation and stereotyped movements, specific developmental disorder of motor function, specific developmental disorders of scholastic skills.

Examples of systemic atrophies primarily affecting the central nervous system that can be treated according to the present invention include, but are not limited to, multiple sclerosis systemic atrophies primarily affecting the basal ganglia including Huntington's disease, and amyotrophic lateral sclerosis.

Examples of extrapyramidal and movement disorders with malfunction and/or degeneration of basal ganglia that can be treated according to the present invention include, but are not limited to, Huntington's disease; Parkinson's disease; second Parkinsonism such as postencephalitic Parkinsonism; Parkinsonism comprised in other disorders; Niemann-Pick disease, Lewy body disease; degenerative diseases of the basal ganglia; other extrapyramidal and movement disorders including tremor, essential tremor and drug-induced tremor, myoclonus, chorea and drug-induced chorea, drug-induced tics and tics of organic origin, drug-induced acute dystonia, drug-induced tardive dyskinesia, muscular spasms and disorders associated with muscular spasticity or weakness including tremors; mental deficiency (including spasticity, Down syndrome and fragile X syndrome), L-dopa-induced dyskinesia; restless leg syndrome and Stiff-man syndrome.

Further examples of movement disorders with malfunction and/or degeneration of basal ganglia that can be treated according to the present invention include, but are not limited to, dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), or mandibular dystonia and spasmodic dysphonia (cramp of the vocal cord); neuroleptic-induced movement disorders including but not limited to neuroleptic malignant syndrome (NMS), neuroleptic-induced Parkinsonism, neuroleptic-induced early onset or acute dyskinesia, neuroleptic-induced acute dystonia, neuroleptic-induced acute akathisia, neuroleptic-induced tardive dyskinesia, and neuroleptic-induced tremor.

Examples of behavioral syndromes associated with physiological disturbances and physical factors according to the present invention include, but are not limited to, nonorganic sleep disorders, including but not limited to nonorganic hypersomnia, nonorganic disorder of the sleep-wake schedule (circadian rhythm sleep disorder), insomnia, parasomnia and sleep deprivation; mental and behavioral disorders associated with the puerperium including postnatal and postpartum depression; eating disorders, including but not limited to anorexia nervosa, bulimia nervosa, binge eating disorder, hyperphagia, obesity, compulsive eating disorders and pagophagia.

Examples of disorders of adult personality and behavior that can be treated according to the present invention include, but are not limited to, personality disorders, including but not limited to emotionally unstable, borderline, obsessive-compulsive, anankastic, dependent and passive-aggressive personality disorder; habit and impulse disorders (impulse-control disorder) including intermittent explosive disorder, pathological gambling, pathological fire-setting (pyromania), pathological stealing (kleptomania), trichotillomania; Munchausen syndrome.

Examples of schizophrenia and other psychotic disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis such as social withdrawal in schizophrenia.

Examples of mental and behavioral disorders due to psychoactive substance use that can be treated according to the present invention include, but are not limited to, mental and behavioral disorders due to use of alcohol, opioids, cannabinoids, sedatives or hypnotics, cocaine; mental and behavioral disorders due to the use of other stimulants including caffeine, mental and behavioral disorders due to drug dependence and abuse (e.g., narcotic dependence, alcoholism, amphetamine and methamphetamine dependence, opioid dependence, cocaine addiction, nicotine dependence, and drug withdrawal syndrome, and relapse prevention), use of hallucinogens, tobacco (nicotine), volatile solvents and mental and behavioral disorders due to multiple drug use and use of other psychoactive substances including the following subtype symptoms: harmful use, dependence syndrome, withdrawal state, and withdrawal state with delirium.

Examples of dementia that can be treated according to the present invention include, but are not limited to, vascular dementia, dementia due to Creutzfeld-Jacob disease, HIV, head trauma, Parkinson's, Huntington's, Pick's disease, dementia of the Alzheimer's type.

In certain embodiments, the present invention is directed to the use of the compounds of the present invention for the treatment of schizophrenia by administration of a therapeutically effective amount of a compound of the present invention to a patient in need thereof.

In certain other embodiments, the invention is further directed to the use of the compounds of the present invention for the treatment of cognitive impairment associated with schizophrenia by administration of a therapeutically effective amount of a compound of the present invention to a patient in need thereof.

Schizophrenia or psychosis for which the compounds, N-oxide thereof, and pharmaceutically acceptable salts of the foregoing of the invention may be useful includes one or more of the following conditions: schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthesia, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's Disease and post-traumatic stress syndrome), including both the positive and the negative symptoms of schizophrenia and other psychoses; cognitive disorders including dementia (associated with Alzheimer's Disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders, or age related cognitive decline.

In addition to the central nervous system disorders mentioned above, the compounds of the present invention may be used to treat other M4-mediated (or M4-associated) disorders such as, but not limited to, addiction (e.g. substance addiction such as addiction to opioids, cocaine, or alcohol), pain (e.g. acute pain, inflammatory pain, and neuropathic pain), and a sleep disorder (such as those related to REM sleep regulation, for example, those related to REM sleep onset). Additional M4-mediated (or M4-associated) disorders or conditions that may be treated by the compounds of the invention include, dry mouth, a cognitive disorder (e.g. mild cognitive impairment), dyskinesia, pulmonary hypertension, chronic obstructive pulmonary disease (COPD), asthma, urinary incontinence, glaucoma, Trisomy 21 (Down Syndrome), cerebral amyloid angiopathy, dementia (e.g. degenerative dementia), Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis. See e.g. U.S. Pat. No. 8,664,234.

Potential sleep disorders for which the compounds, N-oxide thereof, and pharmaceutically acceptable salts of the foregoing of the invention may be useful include: enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds, N-oxide thereof, and pharmaceutically acceptable salts of the foregoing of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, tenosynovitis and gout), headache, migraine and cluster headache, headache, primary hyperalgesia, secondary hyperalgesia, primary allodynia, secondary allodynia, or other pain caused by central sensitization.

The compounds, N-oxides thereof, and pharmaceutically acceptable salts of the foregoing of the invention may be used to decrease tolerance and/or dependence to opioid treatment of pain, and for treatment of withdrawal syndrome of e.g., alcohol, opioids, and cocaine.

Formulations

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be formulated such that administration topically to the skin or mucosa (i.e., dermally or transdermally) leads to systemic absorption of the compound. In another embodiment, the compounds of the invention can also be formulated such that administration intranasally or by inhalation leads to systemic absorption of the compound. In another embodiment, the compounds of the invention may be formulated such that administration rectally or vaginally leads to systemic absorption of the compound.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically (e.g., intranasal or ophthalmic).

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents, and include depot formulations.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of an M4 activator compound of the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-ß (or fragments thereof), such as $Aß_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-ß (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huCO91, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko *biloba* extract EGb-761 (ROKAN, TEBONIN), tramiprosate (CEREBRIL, ALZHEMED), eprodisate (FIBRILLEX, KIACTA), compound W [3,5-bis(4-nitrophenoxy)benzoic acid], NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SEC- TRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxapine, risperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and aminoeptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrolidin-1-ylmethyl)phenyl]-cyclobutanecarboxamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-lL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecyl-2H-pyrrol-2-ylidene)methyl]-1H, 1'H-2,2'-bipyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (1-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, riluzole, N-hydroxy-1,2,4,9-tetrahydro-3H-carbazol-3-imine, desmoteplase, anatibant, astaxanthin, neuropeptide NAP (e.g., AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-ß-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitors such as 2-({4-[1-methyl-4-(pyridin-4-yl)-1H-pyrazol-3-yl]phenoxy}methyl)quinolin-3(4H)-one and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, AcrER (N²-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[(2S)-3-ethyl-1-hydroxypentan-2-yl]benzenesulfonamide;

(xxxiii) serotonin (5-hydroxytryptamine) 1A (5-$HT_{1A}$) receptor antagonists, such as spiperone, levo-pindolol, BMY 7378, NAD-299, S-(−)-UH-301, NAN 190, lecozotan;

(xxxiv) serotonin (5-hydroxytryptamine) 2C (5-$HT_{2c}$) receptor agonists, such as vabicaserin and zicronapine;

(xxxv) serotonin (5-hydroxytryptamine) 4 (5-$HT_4$) receptor agonists, such as PRX-03140 (Epix);

(xxxvi) serotonin (5-hydroxytryptamine) 6 (5-$HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydro-furan-3-yl}propane-2-sulfonamide, and the like.

(xli) Janus kinase inhibitors (JAK) such as, but not limited to, tofacitinib, ruxolitinib, baricitinib, CYT387, GLPG0634, lestaurtinib, pacritinib, and TG101348.

(xlii) Interleukin-1 receptor-associated kinase 4 inhibitors (IRAK4) such as, but not limited to, PF-06650833.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

As noted above, the compounds of the present invention may be used in combination with one or more additional anti-schizophrenia agents which are described herein. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention (or an N-oxide thereof or a pharmaceutically acceptable salt of the foregoing).

The invention also provides a pharmaceutical composition for the treatment of schizophrenia in a mammal, including a human, which comprises an amount of a compound of the present invention (including an N-oxide thereof or a salt of the compound or the N-oxide), as defined above (including hydrates, solvates and polymorphs of said compound or pharmaceutically acceptable salts thereof), in combination with one or more (for example one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

The invention also provides a pharmaceutical composition for treating an M4-mediated (or M4-associated) disease or disorder in a mammal, including a human, which comprises an amount of a compound of the present invention (including an N-oxide thereof or a salt of the compound or the N-oxide), as defined above (including hydrates, solvates and polymorphs of said compound N-oxide or a pharmaceutically acceptable salt of the foregoing), in combination with one or more (for example one to three) other agents for treating the M4-mediated (or M4-associated) disease or disorder, wherein the amount of the active agents and the combination when taken as a whole are therapeutically effective for treating the M4-mediated (or M4-associated) disease or disorder.

It will be understood that the compounds of the present invention depicted above (Formula I, Formula Ia and Formula Ib) are not limited to a particular stereoisomer (e.g. enantiomer or atropisomer) shown, but also include all stereoisomers and mixtures thereof.

General Schemes

The compounds of the invention, or their pharmaceutically acceptable salts, or tautomers and radioisotopes may be prepared by a variety of methods that are analogously known in the art. The reaction schemes described below, together with synthetic methods known in the art of organic chemistry, or modifications and derivatizations that are familiar to those of ordinary skill in the art, illustrate a method for preparing the compounds. Others, including modifications thereof, will be readily apparent to one skilled in the art. Unless otherwise indicated, the substituents in the Schemes are defined as above. Isolation and purification of the products is accomplished by standard procedures, which are known to a chemist of ordinary skill.

The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999; and T. W. Greene and P. G. M. Wuts, Protective Groups in Organic Chemistry, John Wiley & Sons, 2006, which are hereby incorporated by reference.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin-layer chromatography (TLC).

One skilled in the art will recognize that in some cases, the compounds in Schemes 1-9 will be generated as a mixture of diastereomers and/or enantiomers; these may be separated at various stages of the synthetic Scheme using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the Scheme, methods and examples are used for convenience of representation and/or to reflect the order in which they are introduced in the Scheme, and are not intended to necessarily correspond to the symbols, superscripts or subscripts in the appended claims. The Scheme is representative of methods useful in synthesizing the compounds of the present invention. They are not to constrain the scope of the invention in any way.

Compounds of the invention and intermediates thereof may be prepared according to the following reaction schemes and accompanying discussion. Unless otherwise indicated, $R^1$, $R^2$, $R^3$, a, b, c, L, A, and E and structural Formula I in the reaction schemes and discussion that follow are as defined above. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1

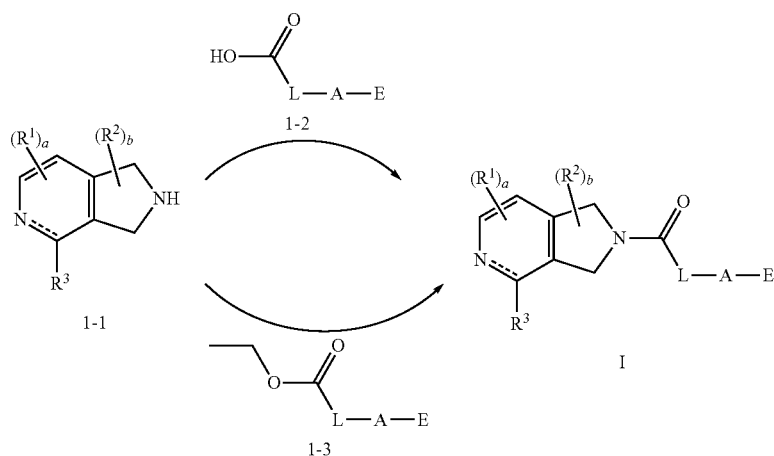

Scheme 1 refers to preparation of compounds of Formula I. Referring to Scheme 1, amines of Formula 1-1, carboxylic acids of Formula 1-2 and esters of Formula 1-3, wherein $R^1$, $R^2$, $R^3$, a, b, L, A, and E are as described above, are either commercially available or can be obtained by the methods described herein in subsequent schemes. A compound of Formula I can be prepared by reacting an amine of Formula 1-1 with a carboxylic acid of Formula 1-2 under amide coupling conditions well known in the art, typically involving a suitable activating reagent, such as O-(7-azabenzotriazol-1-yl)-N,N,N',N'-tetramethyluronium hexafluorophosphate (HATU) or 1,1'-carbonyldiimidazole, with or without a suitable base, e.g., N,N-diisopropylethylamine, and in a suitable solvent, such as N,N-dimethylformamide (DMF) or tetrahydrofuran (THF). Alternatively, a compound of Formula I can be prepared by direct coupling of an amine of Formula 1-1 and an ester of Formula 1-3, under reaction conditions such as heating with 1,3,4,6,7,8-hexahydro-2H-pyrimido[1,2-a]pyrimidine in a suitable solvent, such as DMF, or treatment with trimethylaluminum in a suitable solvent, such as 1,2-dichloroethane, at reaction n temperatures ranging from 50° C. to 100° C. During either of these amide formation reaction steps, the $R^1$, $R^2$, $R^3$, a and b substituents of the amine of Formula 1-1, and the L, A and E substituents of the carboxylic acids of Formula 1-2 and the esters of Formula 1-3 should be represented by the same moiety as is desired in the final product, Formula I, or a protected variation thereof.

Scheme 2

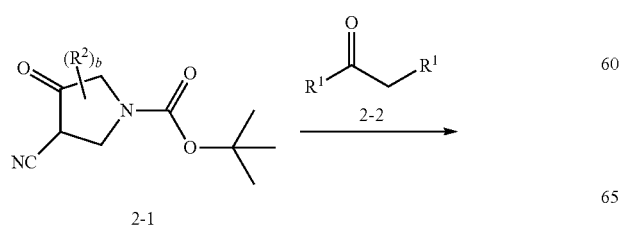

-continued

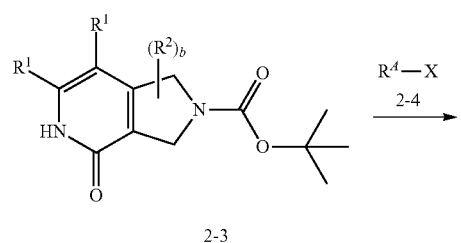

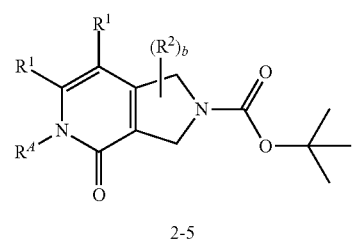

+

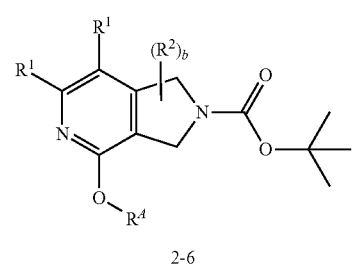

-continued

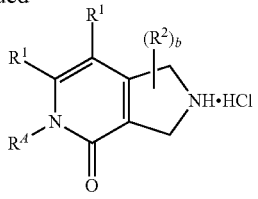

2-7

+

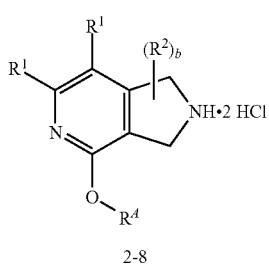

2-8

Scheme 2 refers to preparation of intermediates of Formula 2-7 and 2-8 that can be used in the amide formation reaction described in Scheme 1. Referring to Scheme 2, compounds of Formula 2-1, wherein $R^2$ and b are as described above, are either commercially available or can be obtained by methods well known in the art. A compound of Formula 2-1 can be converted to a pyridone of Formula 2-3 via condensation with a ketone of Formula 2-2, wherein the two $R^1$ groups may be the same or different, in the presence of a suitable dehydrating agent, such as polyphosphoric acid. The pyridone moiety of the compound of Formula 2-3 can then be alkylated with an alkylation reagent of Formula 2-4, wherein $R^A$ is equal to $R^1$ as described above for synthesizing Formula 2-5 and 2-7 or $R^A$ is equal to an optionally substituted —($C_1$-$C_6$)alkyl, —($C_3$-$C_6$)cycloalkyl, or —C(=O)—N($R^4$)($R^5$) when synthesizing a compound of Formula 2-6 and 2-8, wherein X is a suitable leaving group, such as Br or I, to provide a pair of regioisomers: a pyridone of Formula 2-5 and a pyridine of Formula 2-6. The formation of the pyridine regioisomer of Formula 2-6 can be promoted by utilization of a suitable base, such as silver carbonate. The Boc protecting group can then be removed using an excess of hydrogen chloride in a suitable solvent, such as methanol or dichloromethane, to give the desired intermediates of Formula 2-7 and 2-8. During this reaction scheme, the $R^2$ substituent and b of Formula 2-1 and the $R^1$ substituent of Formula 2-2 should be represented by the same moiety as is desired in the final product, Formula I, or a protected variation thereof.

Scheme 3

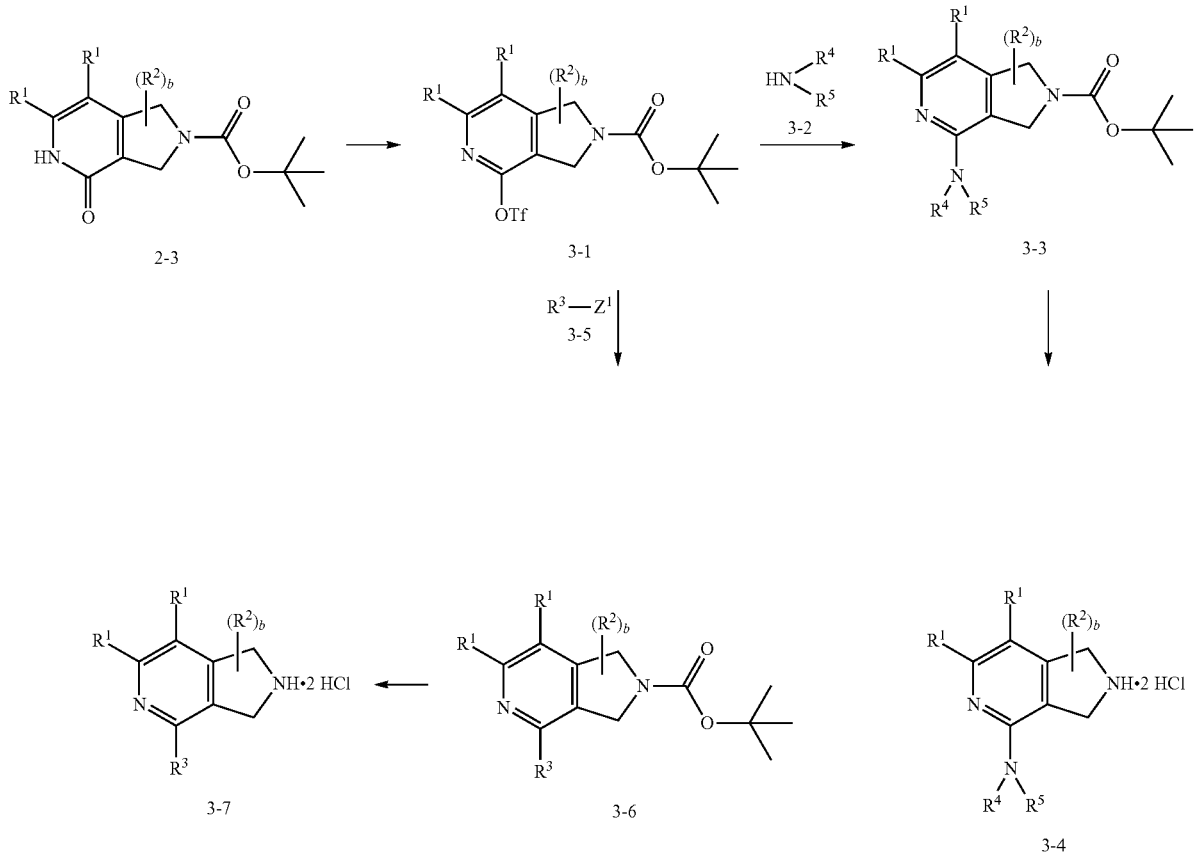

Scheme 3 refers to preparation of intermediates of Formula 3-4 and Formula 3-7 that can be used in the amide formation reactions described in Scheme 1, wherein $R^1$, $R^2$, $R^3$, $R^4$, $R^5$, a and b are as described above. Referring to Scheme 3, an intermediate of Formula 2-3 can be converted to the corresponding triflate of Formula 3-1 using trifluoromethanesulfonic anhydride, in the presence of a suitable base, such as triethylamine, and a suitable solvent, such as dichloromethane. A compound of Formula 3-3 can then be obtained by heating the triflate of Formula 3-1 with an amine of Formula 3-2, in a suitable solvent, such as tetrahydrofuran, at a reaction temperature ranging from 50° C. to 90° C. Alternatively, the amine substitutent of a compound of Formula 3-3 can be introduced via coupling with an amine of Formula 3-2 under reaction conditions well known in the art, consisting of a suitable catalyst, such as palladium(II) acetate or tris(dibenzylideneacetone)dipalladium(0) [$Pd_2(dba)_3$], a suitable ligand, such as 1,1'-binaphthalene-2,2'-diylbis(diphenylphosphane) (BINAP) or 4,5-bis(diphenylphosphino)-9,9-dimethylxanthene (Xantphos), and a suitable base, such as cesium carbonate, in a suitable solvent, such as toluene or 1,4-dioxane. The Boc protecting group can then be removed using an excess of hydrogen chloride in a suitable solvent, such as methanol, to give the desired intermediates of Formula 3-4. The triflate intermediate of Formula 3-1 can also be reacted with a reagent of Formula 3-5, wherein $R^3$ can be optionally substituted heteroaryls and aryls, and $Z^1$ can be $B(OR)_2$, wherein each R is independently H or $C_{1-6}$ alkyl, or wherein two (OR) groups, together with the B atom to which they are attached, form a 5- to 10-membered heterocycloalkyl optionally substituted with one or more $C_{1-6}$ alkyl], in the presence of a suitable catalyst such as [1,1'-bis(diphenylphosphino)ferrocene]dichloropalladium(II), a suitable base such as sodium carbonate, and in a suitable solvent, such as 1,4-dioxane, to give a compound of Formula 3-6. Finally, an intermediate of Formula 3-7 can then be prepared via removal of the Boc protecting group from the compound of Formula 3-6 using an excess of hydrogen chloride in a suitable solvent, such as methanol or dichloromethane. During this reaction scheme, $R^1$, $R^2$ and b of Formula 2-3; the $R^3$ substituent of Formula 3-5; and $R^4$ and $R^5$ of Formula 3-3 should be represented by the same moiety as is desired in the final product, Formula I, or a protected variation thereof.

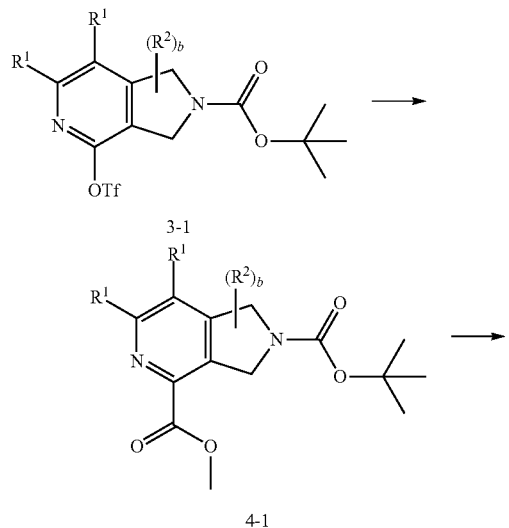

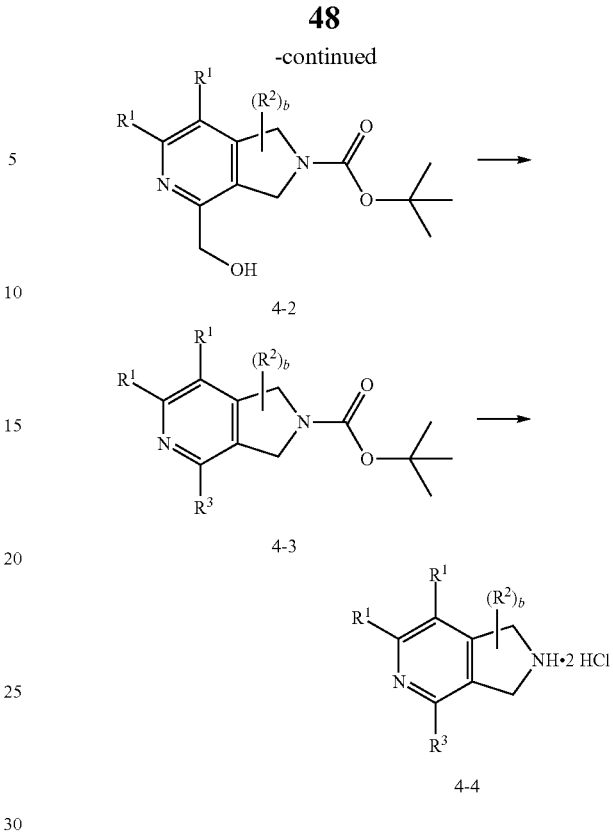

Scheme 4 refers to preparation of intermediates of Formula 4-4 that can be used in the amide formation reactions described in Scheme 1; $R^3$ represents substituents that can be easily derived from an alcohol at the benzylic position using methods well known in the art, such as, but not limited to, benzyl amines, alkoxymethyl groups, and fluorinated alkyl groups, such as fluoromethyl or difluoromethyl groups. Referring to Scheme 4, a triflate of Formula 3-1 can be converted to a methyl ester of Formula 4-1 via carbonylation in methanol with carbon monoxide (e.g., 50 psi) in the presence of a suitable catalyst, such as [1,1'-bis(diphenylphosphino)ferrocene]dichloropalladium(II) and a suitable base, such as triethylamine. The corresponding alcohol of Formula 4-2 can then be prepared by treating a compound of Formula 4-1 with a suitable reducing agent, such as lithium borohydride, in a suitable solvent, such as methanol. A compound of Formula 4-3 can then be prepared using reaction conditions and synthetic sequences well known in the art to convert the alcohol group of Formula 4-2 to substituent $R^3$. The Boc protecting group can then be removed using an excess of hydrogen chloride in a suitable solvent, such as methanol or dichloromethane, to give the desired intermediates of Formula 4-4. During this reaction scheme, $R^1$, $R^2$ and b of Formula 3-1; and the $R^3$ substituent of Formula 4-3 should be represented by the same moiety as is desired in the final product, Formula I, or a protected variation thereof.

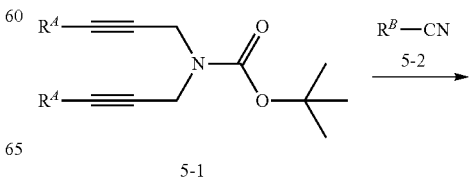

-continued

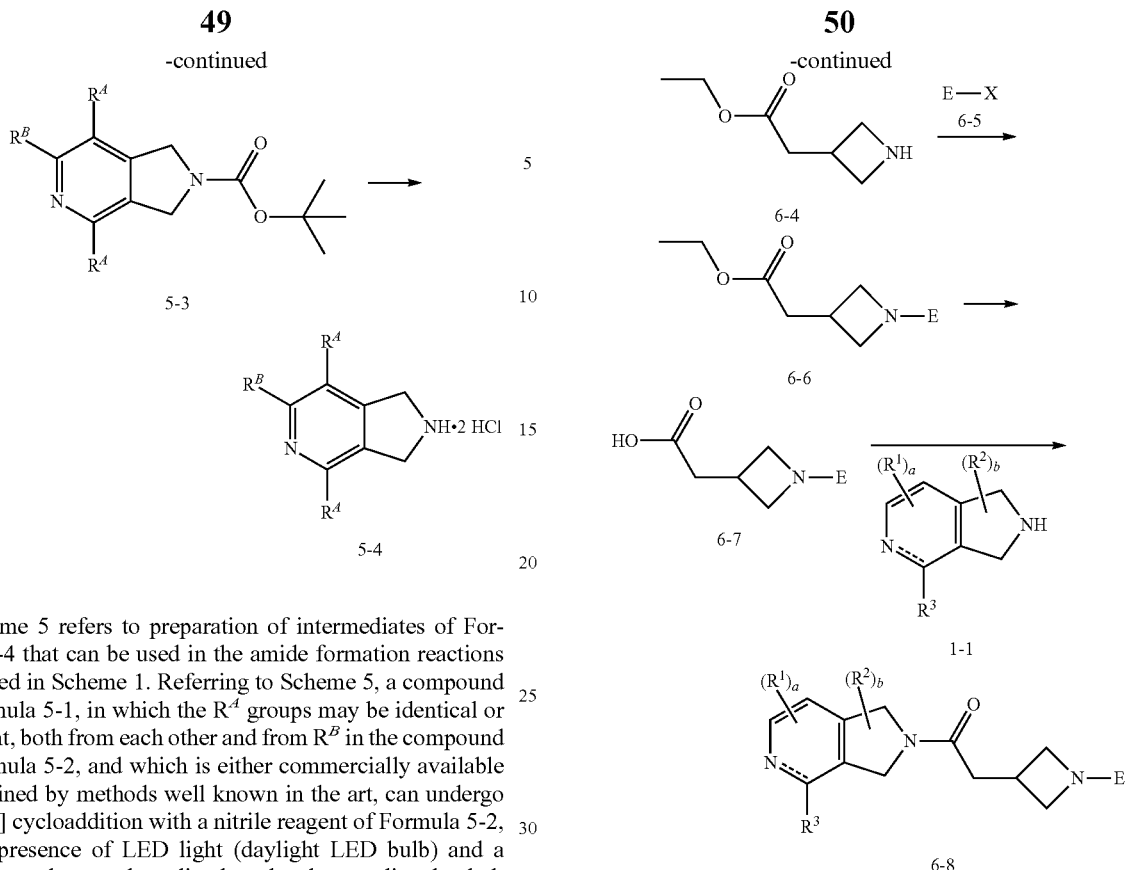

Scheme 5 refers to preparation of intermediates of Formula 5-4 that can be used in the amide formation reactions described in Scheme 1. Referring to Scheme 5, a compound of Formula 5-1, in which the $R^A$ groups may be identical or different, both from each other and from $R^B$ in the compound of Formula 5-2, and which is either commercially available or obtained by methods well known in the art, can undergo [2+2+2] cycloaddition with a nitrile reagent of Formula 5-2, in the presence of LED light (daylight LED bulb) and a suitable catalyst, such as dicarbonylcyclopentadienyl cobalt (I), in a suitable solvent, such as xylene, at elevated temperature, such as 135° C. For example, $R^A$ of Formula 5-1 can be represented by the substituents described in $R^1$ and/or $R^3$ as described above, and $R^B$ of Formula 5-2 can be represented by the substituents described in $R^1$ as described above. The resulting pyridine of Formula 5-3 can then be deprotected using an excess of hydrogen chloride in a suitable solvent, such as methanol or dichloromethane, to give the desired intermediates of Formula 5-4. During this reaction scheme, $R^A$ of Formula 5-1; and the $R^B$ substituent of Formula 5-2 should be represented by the same moiety as is desired in the final product, Formula I, or a protected variation thereof.

Scheme 6

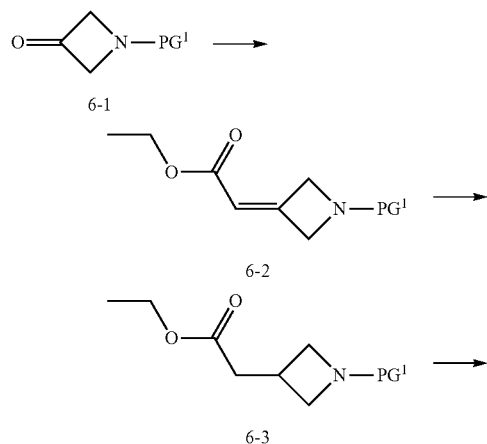

Scheme 6 refers to preparation of a compound of Formula 6-8. Referring to Scheme 6, a compound of Formula 6-1 is either commercially available or can be obtained by methods well known in the art, wherein $PG^1$ is a suitable protecting group such as Boc. A compound of Formula 6-1 can be converted to a compound of Formula 6-2 via Wittig olefination using a suitable reagent, such as (carboethoxymethylene)-triphenylphosphorane. A compound of Formula 6-3 can then be obtained via hydrogenation in the presence of a suitable catalyst, such as 10% palladium on carbon, in a suitable solvent, such as tert-butyl methyl ether. Upon removal of $PG^1$ using methods well known in the art, an azetidine intermediate of Formula 6-4 can be obtained. Suitable terminal substituents (E as described above) can be introduced via suitable coupling conditions well known in the art with a reagent of Formula 6-5, wherein E is as described above and X is Cl, Br, or I, to give compounds of Formula 6-6. For example, when E is a heteroaryl and X is ortho- or para- to a heteroaryl nitrogen atom, the coupling reaction can be achieved via an $S_NAr$ reaction well known in the art, in the presence of a suitable base, such as triethylamine, and a suitable salt, such as cesium fluoride, in a suitable solvent, such as dimethyl sulfoxide (DMSO). In another example, wherein E is an aryl or heteroaryl and X is Cl, Br, or I not activated by a heteroaryl nitrogen, the coupling reaction can be achieved in the presence of a suitable catalyst, such as tris(dibenzylideneacetone)dipalladium(0) [$Pd_2(dba)_3$], a suitable ligand, such as 1,1'-binaphthalene-2,2'-diylbis(diphenylphosphane) (BINAP) or 4,5-bis(diphenylphosphino)-9,9-dimethylxanthene (Xantphos), and a suitable base, such as cesium carbonate, in a suitable solvent, such as toluene or 1,4-dioxane. A compound of Formula 6-6 can then be converted to the corresponding carboxylic acid of Formula 6-7 via ester hydrolysis, using a suitable base such as sodium hydroxide or lithium hydroxide. A compound of Formula 6-8 can then be prepared from a carboxylic acid of Formula 6-7 and an amine of Formula 1-1 via amide formation as described in Scheme 1. During this reaction scheme, $R^1$, $R^2$, $R^3$, a and b of Formula 1-1; and E in Formula 6-5 should be represented by the same moiety as is desired in the final product, Formula I, or a protected variation thereof.

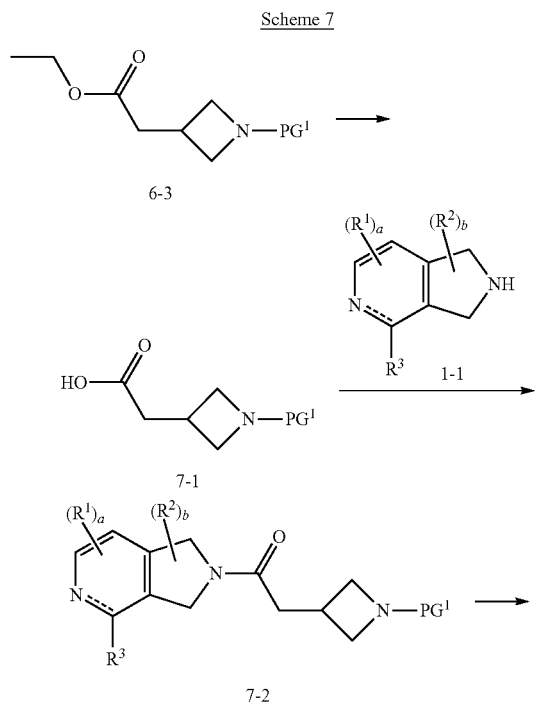

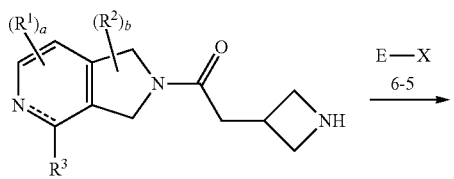

Scheme 7 refers to an alternative preparation of a compound of Formula 6-8. Referring to Scheme 7, a compound of Formula 6-3, wherein $PG^1$ is as described above, can be converted to the corresponding carboxylic acid of Formula 7-1, which can be coupled with an amine of Formula 1-1 using the conditions described in Scheme 1 to give a compound of Formula 7-2. Protecting group $PG^1$ can be removed using methods well known in the art, to afford a compound of Formula 7-3, which can be converted to a compound of Formula 6-8 using the coupling conditions described in Scheme 6. During this reaction scheme, $R^1$, $R^2$, $R^3$, a and b of Formula 1-1; and E in Formula 6-5 should be represented by the same moiety as is desired in the final product, Formula I, or a protected variation thereof.

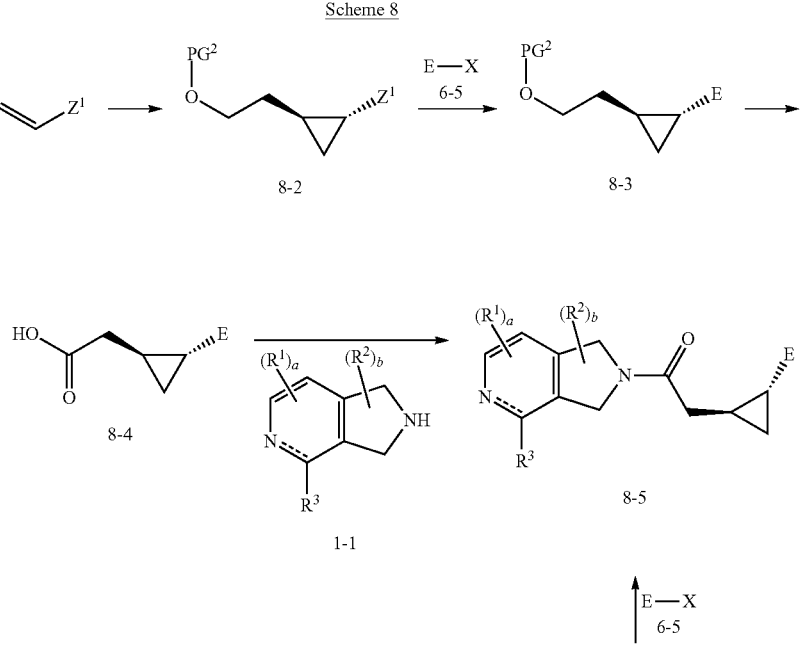

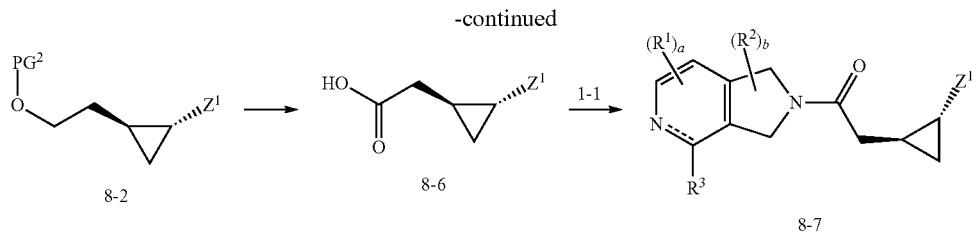

Scheme 8 refers to preparation of a compound of Formula 8-5, wherein $R^1$, $R^2$, $R^3$, a, b, and E are as described above. The compounds in this scheme are depicted as single enantiomers for illustration purposes only: they can be either enantiomer, or a mixture thereof. Referring to Scheme 8, a compound of Formula 8-1, wherein $PG^2$ is a suitable silyl-based protecting group, such as a tert-butyl(dimethyl)silyl (TBDMS) group, and $Z^1$ is a boronic ester $B(OR)_2$' wherein each R is independently H or $C_{1-6}$ alkyl, or wherein the two —OR groups, together with the B atom to which they are attached, form an optionally substituted 5- to 10-membered heterocycloalkyl, is either commercially available or can be obtained by methods well known in the art. A compound of Formula 8-1 can be converted to a compound of Formula 8-2 via a cyclopropanation reaction well known in the art. A typical procedure involves treating an alkene with a zincate species derived from diiodomethane and diethylzinc in the presence of a suitable acid, such as trichloroacetic acid, in a suitable solvent, such as dichloromethane. A compound of Formula 8-3 can be prepared via a Suzuki coupling of a compound of Formula 8-2 and a reagent of Formula 6-5, wherein E is an aryl or heteroaryl and X is Cl, Br, or I, in the presence of a suitable catalyst, such as palladium(II) acetate, and a suitable ligand, such as di(1-adamantyl)-n-butylphosphine (cataCXium® A), in the presence of a suitable base, such as cesium carbonate, and in a suitable solvent, such as 2-methylbutan-2-ol. Upon oxidation with a suitable reagent, such as sodium periodate, in the presence of a suitable catalyst, such as ruthenium(III) chloride, a compound of Formula 8-3 can be converted to the corresponding carboxylic acid of Formula 8-4, which in turn can be coupled with an amine of Formula 1-1 to give a compound of Formula 8-5 using the amide formation conditions described in Scheme 1. Alternatively, a compound of Formula 8-2 can be converted to the corresponding carboxylic acid 8-6 using the conditions described above, which can then be coupled with an amine of Formula 1-1 to afford a compound of Formula 8-7 via amide formation. A compound of Formula 8-5 can then be obtained via coupling reaction of a compound of Formula 8-7 with a reagent of Formula 6-5 using the conditions described above. During this reaction scheme, $R^1$, $R^2$, $R^3$, a, and b of Formula 1-1; and E in Formula 6-5 should be represented by the same moiety as is desired in the final product, Formula I, or a protected variation thereof.

Scheme 9

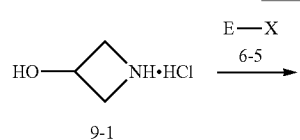

Scheme 9 refers to preparation of a compound of Formula 9-3, wherein $R^1$, $R^2$, $R^3$, a, b, and E are as described above. Referring to Scheme 9, a compound of Formula 9-2 can be prepared via coupling of azetidin-3-ol, hydrochloride salt (9-1) with a reagent of Formula 6-5 wherein E is an aryl or heteroaryl and X is Cl, Br, or I. For example, when E is a heteroaryl and X is ortho- or para- to a heteroaryl nitrogen atom, the coupling reaction can be achieved via an $S_NAr$ reaction well known in the art, in the presence of a suitable base, such as triethylamine, and a suitable salt, such as cesium fluoride, in a suitable solvent, such as dimethyl sulfoxide (DMSO). In another example, wherein E is an aryl or heteroaryl and X is Cl, Br, or I not activated by a heteroaryl nitrogen, the coupling reaction can be achieved in the presence of a suitable catalyst, such as tris(dibenzylideneacetone)dipalladium(0) $[Pd_2(dba)_3]$, a suitable ligand, such as 1,1'-binaphthalene-2,2'-diylbis(diphenylphosphane) (BINAP) and 4,5-bis(diphenylphosphino)-9,9-dimethylxanthene (Xantphos), and a suitable base, such as cesium carbonate, in a suitable solvent, such as toluene or 1,4-dioxane. The desired compound of Formula 9-3 can then be prepared from coupling of an alcohol of Formula 9-2 and an amine of Formula 1-1 using a suitable activating reagent, such as bis(pentafluorophenyl) carbonate or bis(trichloromethyl) carbonate, in the presence of a suitable base, such as triethylamine, and an optional catalyst, such as 4-(dimethylamino)pyridine, in a suitable solvent, such as acetonitrile or dichloromethane. During this reaction scheme, $R^1$, $R^2$, $R^3$, a, and b of Formula 1-1; and E in Formula 6-5 should be represented by the same moiety as is desired in the final product, Formula I, or a protected variation thereof.

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a part of the compound structure such as a substituent group, for example $R^1$, $R^2$, $R^3$, L, A, and E etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion ($CN^-$). For another example, an —S— can be oxidized to —S(=O)— and/or —S(=O)$_2$—. For yet another example, an unsaturated bond such as C=C or C≡C can be reduced to a saturated bond by hydrogenation. In some embodiments, a primary amine or a secondary amine moiety (present on a substituent group such as $R^1$, $R^2$, L, A, E, etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^1$, $R^2$, $R^3$, L, A, and E, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an $NH_2$ group can be protected by a benzyloxycarbonyl (Cbz) or Boc group; conversion back to the $NH_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, with mixed solvent systems, such as but limited to aqueous plus acetonitrile, either or both of which may contain additives such as trifluoroacetic acid, formic acid, concentrated ammonium hydroxide, or with supercritical fluid chromatography, carried out using a combination of carbon dioxide and an organic solvent such as methanol or acetonitrile, optionally containing an additive such as diethylamine or ammonium hydroxide. on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well known to those of ordinary skill in the art.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "mL" means milliliter, "mmol" means millimoles, "μmol" means micromoles, "eq." means equivalent, "° C." means degrees Celsius, "MHz" means megahertz, "HPLC" means high-performance liquid chromatography.

EXPERIMENTAL PROCEDURES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride, or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

The following are abbreviations which may appear in the experimental procedures described herein:

BINAP=1,1'-binaphthalene-2,2'-diylbis(diphenylphosphane); Boc=tert-butoxycarbonyl; br=broad; n-BuLi=n-butyllithium; $CDCl_3$=deuterochloroform; $CD_3OD$=deuteromethanol; $CF_3COOH$=trifluoroacetic acid; $CpCo(CO)_2$=dicarbonylcyclopentadienyl cobalt(I); $Cs_2CO_3$=cesium carbonate; d=doublet; dd=doublet of doublets; ddd=doublet of doublet of doublets; cataCXium® A=bis(1-adamantyl)-butylphosphane; ENT-1=first-eluting enantiomer; ENT-2=second-eluting enantiomer; g=gram; GCMS=gas chromatography-mass spectrometry; HATU=0-(7-azabenzotriazol-1-yl)-N,N,N',N'-tetramethyluronium hexafluorophosphate; HCl=hydrochloric acid; HPLC=high-performance liquid chromatography; Hz=hertz; $K_2CO_3$=potassium carbonate; LCMS=liquid chromatography mass spectrometry; m=multiplet; M=molar; mg=milligram; MHz=megahertz; mL=milliliter; μL=microliter; mmol=millimole; μmol=micromole; mol=mole; NaH=sodium hydride; $NaHCO_3$=sodium bicarbonate; NaOAc=sodium acetate; $NEt_3$=triethylamine; $NH_4Cl$=ammonium chloride; $NH_2OH \cdot HCl$=hydroxylamine hydrochloride; NMR=nuclear magnetic resonance; NOE=Nuclear Overhauser effect; $Pd_2(dba)_3$=tris(dibenzylideneacetone)dipalladium(0); $Pd(dppf)Cl_2$=[1,1'-bis(diphenylphosphino)-ferrocene]dichloropalladium(II); $Pd(OAc)_2$=palladium(II) acetate; $PPh_3$=triphenylphosphine; psi=pounds per square inch; q=quartet; s=singlet; SPhos Pd G2=chloro(2-dicyclohexylphosphino-2',6'-dimethoxy-1'-biphenyl)[2-(2'-amino-1,1'-biphenyl)]palladium(II); t=triplet; Xantphos=4,5-bis(diphenylphosphino)-9,9-dimethylxanthene.

Preparation P1 tert-Butyl 5,6,7-trimethyl-4-oxo-1,3,4,5-tetrahydro-2H-pyrrolo[3,4-c]pyridine-2-carboxylate (P1)

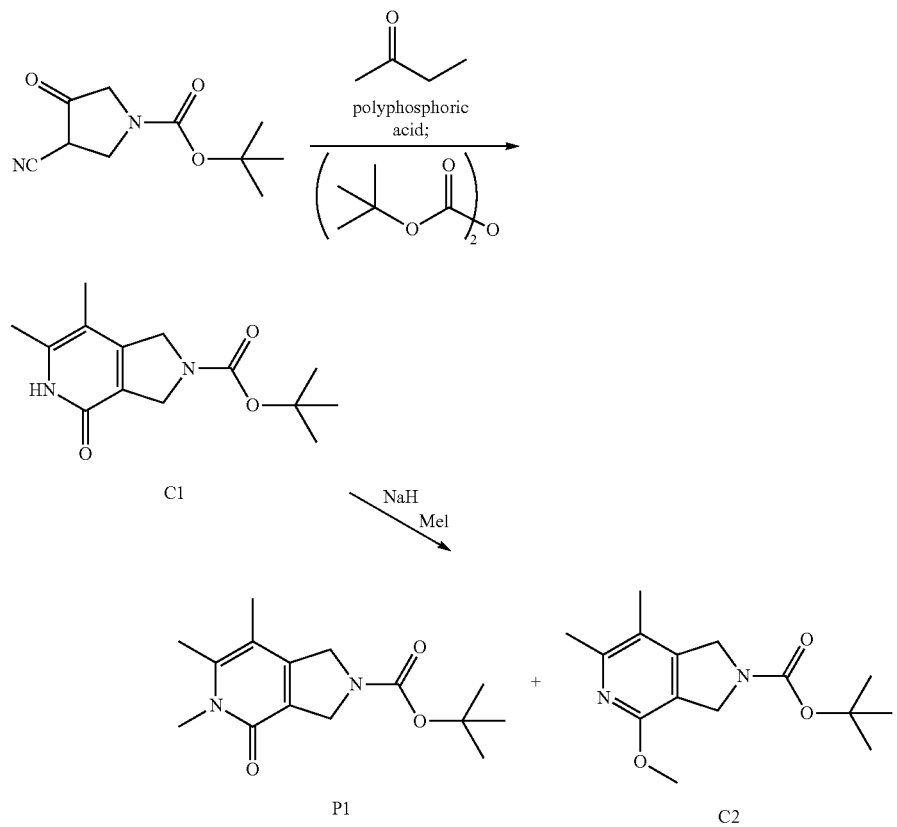

Step 1. Synthesis of tert-butyl 6,7-dimethyl-4-oxo-1,3,4,5-tetrahydro-2H-pyrrolo[3,4-c]pyridine-2-carboxylate (C1)

A mixture of tert-butyl 3-cyano-4-oxopyrrolidine-1-carboxylate (5.00 g, 23.8 mmol) in butan-2-one (20 mL) was added to polyphosphoric acid (100 g) at 100° C., and the reaction mixture was stirred at 100° C. to 120° C. for 4 hours. After the reaction mixture had been cooled to 15° C., it was quenched via addition of water (1.5 L), and the pH of the mixture was adjusted to 10-11 using solid sodium hydroxide. Di-tert-butyl dicarbonate (10.0 g, 45.8 mmol) was added, and the reaction mixture was stirred for 15 hours at 15° C., whereupon it was filtered. The collected solid was washed sequentially with water (7×50 mL) and with a mixture of tert-butyl methyl ether and petroleum ether (1:1; 7×40 mL) to afford the product as an off-white solid. From analysis of the $^1$H NMR, this material was presumed to exist as a mixture of rotamers. Yield: 4.0 g, 15 mmol, 63%. LCMS m/z 264.8 [M+H]$^+$. $^1$H NMR (400 MHz, CDCl$_3$) δ 12.6-12.5 (br s, 1H), 4.65-4.48 (m, 4H), 2.32 (s, 3H), 1.97 (s, 3H), [1.52 (s) and 1.51 (s), total 9H].

Step 2. Synthesis of tert-butyl 5,6,7-trimethyl-4-oxo-1,3,4,5-tetrahydro-2H-pyrrolo[3,4-c]pyridine-2-carboxylate (P1)

Sodium hydride (60% dispersion in mineral oil; 567 mg, 14.2 mmol) was added in portions to a 0° C. suspension of C1 (2.50 g, 9.46 mmol) in N,N-dimethylformamide (100 mL), and the reaction mixture was stirred at room temperature (18° C.) for 30 minutes. Iodomethane (1.61 g, 11.3 mmol) was then added to the reaction mixture and stirring was continued for 2 hours, whereupon the reaction mixture was poured into water (200 mL) and extracted with ethyl acetate (3×150 mL). The combined extracts were washed with water (3×300 mL) and with saturated aqueous sodium chloride solution (500 mL), dried over sodium sulfate, filtered, and concentrated in vacuo. Chromatography on silica gel (Eluent: 60:1 dichloromethane/methanol) afforded P1 as a pale yellow solid. Yield: 912 mg, 3.28 mmol, 35%. LCMS m/z 278.9 [M+H]$^+$. $^1$H NMR (400 MHz, CDCl$_3$) δ 4.62-4.50 (m, 4H), 3.58 (s, 3H), 2.32 (s, 3H), 2.02 (s, 3H), [1.52 (s) and 1.50 (s), total 9H].

Also isolated, and further purified via silica gel chromatography (Eluent: 15:1 petroleum ether/ethyl acetate), was byproduct tert-butyl 4-methoxy-6,7-dimethyl-1,3-dihydro-2H-pyrrolo[3,4-c]pyridine-2-carboxylate (C2), as a pale yellow solid. Yield: 100 mg, 0.36 mmol, 4%. LCMS m/z 278.9 [M+H]$^+$. $^1$H NMR (400 MHz, CDCl$_3$) δ 4.63-4.49 (m, 4H), [3.94 (s) and 3.93 (s), total 3H], 2.41 (s, 3H), 2.10 (s, 3H), [1.53 (s) and 1.51 (s), total 9H]. From analysis of their $^1$H NMR spectra, both P1 and C2 were presumed to exist as mixtures of rotamers.

Preparation P2

N,6,7-Trimethyl-2,3-dihydro-1H-pyrrolo[3,4-c]pyridin-4-amine, dihydrochloride Salt (P2)

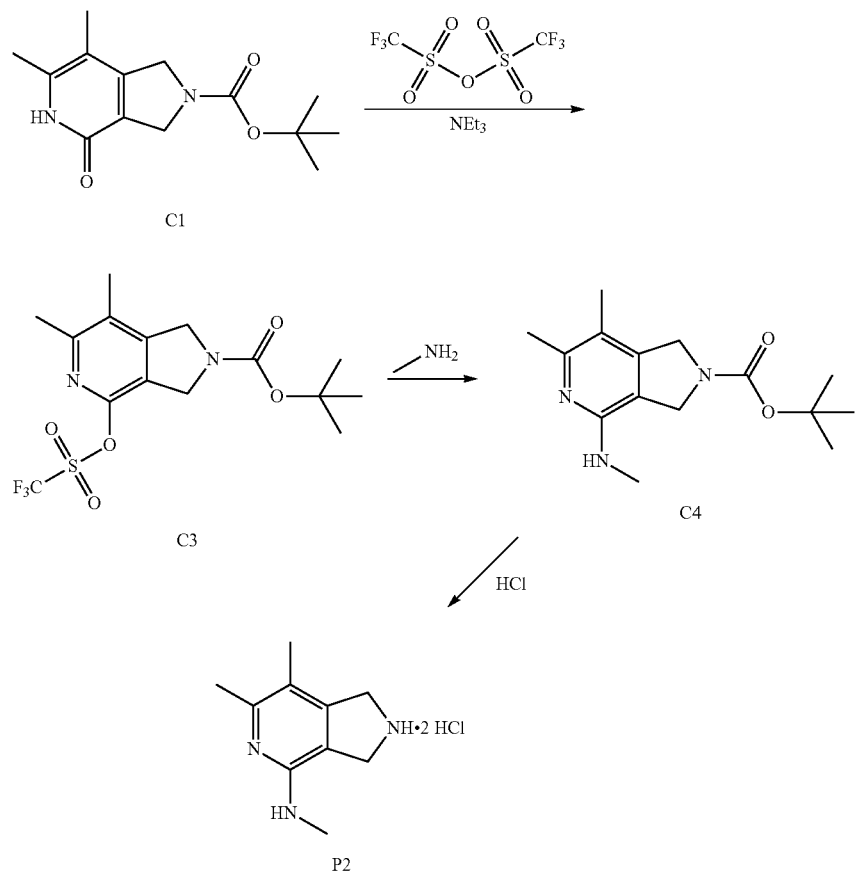

Step 1. Synthesis of tert-butyl 6,7-dimethyl-4-{[(trifluoromethyl)sulfonyl]oxy}-1,3-dihydro-2H-pyrrolo[3,4-c]pyridine-2-carboxylate (C3)

Triethylamine (24.9 g, 246 mmol) and trifluoromethanesulfonic anhydride (58.7 g, 208 mmol) were added to a 0° C. solution of C1 (50.0 g, 189 mmol) in dichloromethane (2 L). The reaction mixture was stirred for 2 hours at 0° C., whereupon it was quenched with water (50 mL) and extracted with dichloromethane (3×200 mL). The combined organic layers were washed with saturated aqueous sodium chloride solution (500 mL), dried over sodium sulfate, filtered, and concentrated in vacuo. Silica gel chromatography (Eluent: 5:1 petroleum ether/ethyl acetate) afforded the product as a pale yellow solid. Yield: 54.0 g, 136 mmol, 72%. $^1$H NMR (400 MHz, CDCl$_3$) δ 4.79-4.61 (m, 4H), 2.49 (s, 3H), 2.22 (s, 3H), 1.53 (s, 9H).

Step 2. Synthesis of tert-butyl 6,7-dimethyl-4-(methylamino)-1,3-dihydro-2H-pyrrolo[3,4-c]pyridine-2-carboxylate (C4)

Compound C3 (3.5 g, 8.8 mmol) was mixed with a solution of methylamine in tetrahydrofuran (2.0 M, 70 mL, 140 mmol), and the reaction mixture was stirred at 90° C. for 40 hours. It was then concentrated in vacuo, and the residue was purified by silica gel chromatography (Gradient: 20% to 33% ethyl acetate in petroleum ether) to provide the product as a white solid. From analysis of the $^1$H NMR, this material was presumed to exist as a mixture of rotamers. Yield: 1.25 g, 4.51 mmol, 51%. $^1$H NMR (400 MHz, CDCl$_3$) δ 4.59-4.41 (m, 4H), 3.81-3.66 (m, 1H), 3.03 (d, J=5.0 Hz, 3H), 2.40 (s, 3H), 2.06 (s, 3H), [1.53 (s) and 1.52 (s), total 9H].

Step 3. Synthesis of N,6,7-trimethyl-2,3-dihydro-1H-pyrrolo[3,4-c]pyridin-4-amine, dihydrochloride Salt (P2)

A solution of hydrogen chloride in methanol (4 M, 206 mL) was added in a drop-wise manner to a 0° C. solution of C4 (11.45 g, 41.28 mmol) in dichloromethane (200 mL). The reaction mixture was stirred at room temperature for 1 hour, whereupon the solvent was removed in vacuo, affording the product as a white solid. Yield: 10.32 g, 41.25 mmol, quantitative. LCMS m/z 178.2 [M+H]$^+$. $^1$H NMR (400 MHz, DMSO-d$_6$), characteristic peaks: δ 10.38-10.23 (br s, 2H), 4.58 (br s, 2H), 4.43 (br s, 2H), 3.04 (br s, 3H), 2.07 (s, 3H).

Preparation P3

6,7-Dimethyl-2,3-dihydro-1H-pyrrolo[3,4-c]pyridine-4-amine, dihydrochloride Salt (P3)

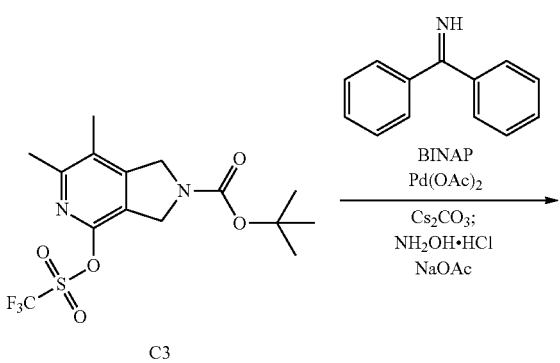

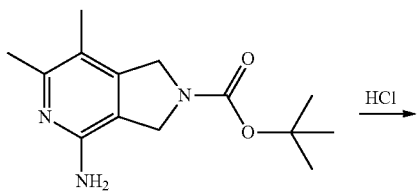

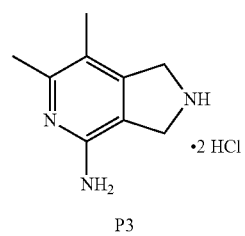

Step 1. Synthesis of tert-butyl 4-amino-6,7-dimethyl-1,3-dihydro-2H-pyrrolo[3,4-c]pyridine-2-carboxylate (C5)

A mixture of C3 (9.20 g, 23.2 mmol), 1,1-diphenylmethanimine (6.31 g, 34.8 mmol), palladium(II) acetate (521 mg, 2.32 mmol), 1,1'-binaphthalene-2,2'-diylbis(diphenylphosphane) (BINAP; 1.45 g, 2.33 mmol), and cesium carbonate (11.3 g, 34.7 mmol) in toluene (100 mL) was heated at 100° C. for 16 hours, whereupon the reaction mixture was filtered, and the filtrate was concentrated in vacuo. The residue was dissolved in methanol (100 mL) and treated with sodium acetate (4.0 g, 48.8 mmol) and hydroxylamine hydrochloride (3.39 g, 48.8 mmol). This reaction mixture was stirred at room temperature for 72 hours. It was then filtered, and the filtrate was concentrated under reduced pressure. Silica gel chromatography (Gradient: 33% to 100% ethyl acetate in petroleum ether) was followed by crystallization from ethyl acetate. The resulting solid was washed with tert-butyl methyl ether (3×10 mL) to provide the product as an off-white solid. Yield: 5.0 g, 19 mmol, 82%. LCMS m/z 264.0 [M+H]$^+$.

Step 2. Synthesis of 6,7-dimethyl-2,3-dihydro-1H-pyrrolo[3,4-c]pyridine-4-amine, dihydrochloride Salt (P3)

A solution of hydrogen chloride in methanol (4 M, 20 mL, 80 mmol) was added to a solution of C5 (3.10 g, 11.8 mmol) in methanol (100 mL), and the reaction mixture was stirred at room temperature (10° C.) for 18 hours. Removal of solvent under reduced pressure afforded the product as a white solid. Yield: 2.2 g, 9.3 mmol, 79%. $^1$H NMR (400 MHz, DMSO-d$_6$) δ 10.39-10.21 (br s, 2H), 7.88-7.69 (br s, 2H), 4.58 (s, 2H), 4.42 (s, 2H), 2.42 (s, 3H), 2.07 (s, 3H).

Preparation P4

4,6,7-Trimethyl-2,3-dihydro-1H-pyrrolo[3,4-c]pyridine, dihydrochloride Salt (P4)

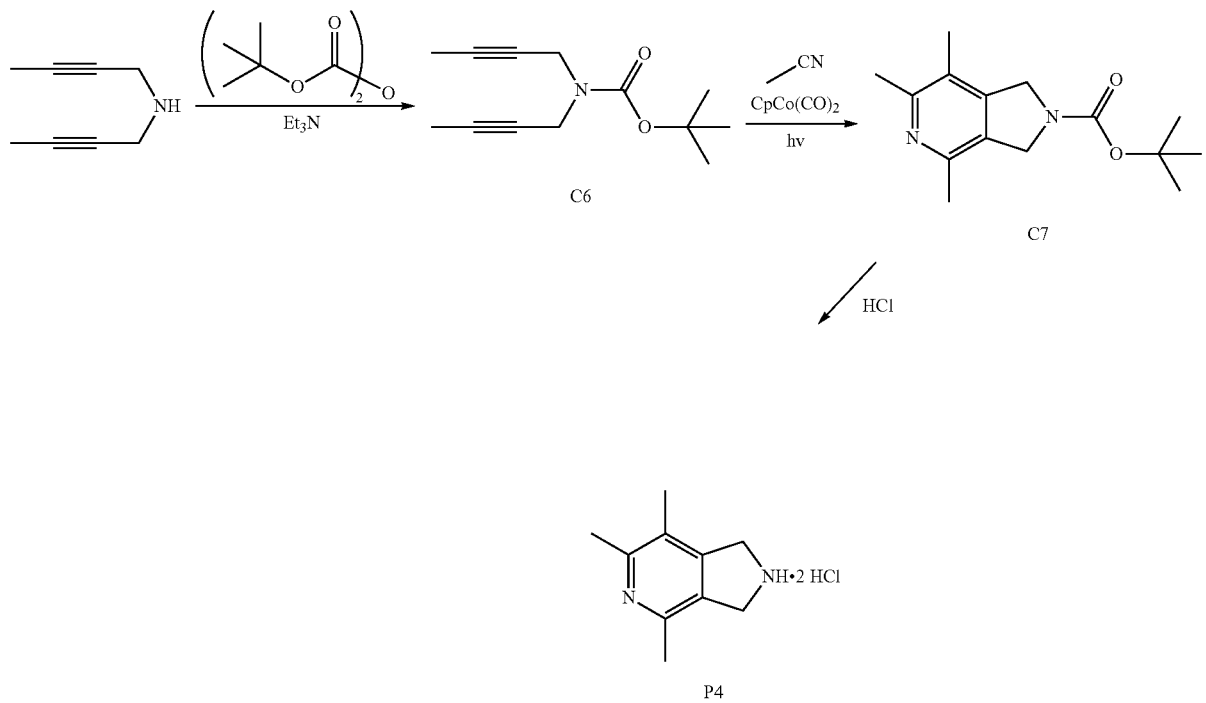

Step 1. Synthesis of tert-butyl dibut-2-yn-1-ylcarbamate (C6)

To a 0° C. solution of N-(but-2-yn-1-yl)but-2-yn-1-amine (1.00 g, 8.25 mmol) in dichloromethane (30 mL) was added triethylamine (2.30 mL, 16.5 mmol), followed by di-tert-butyl dicarbonate (2.70 g, 12.4 mmol). The ice bath was allowed to melt and the reaction mixture was stirred at room temperature overnight. It was then washed twice with water and once with saturated aqueous sodium chloride solution; the organic layer was dried over sodium sulfate, filtered, and concentrated in vacuo. The resulting material was chromatographed twice on silica gel (Gradient: 0% to 100% ethyl acetate in heptane, followed by 0% to 30% ethyl acetate in heptane), affording the product as a colorless oil. Yield: 1.09 g, 4.93 mmol, 60%. GCMS m/z 221.1 [M$^+$]. $^1$H NMR (400 MHz, CDCl$_3$) δ 4.11 (br s, 4H), 1.82 (t, J=2.4 Hz, 6H), 1.48 (s, 9H).

Step 2. Synthesis of tert-butyl 4,6,7-trimethyl-1,3-dihydro-2H-pyrrolo[3,4-c]pyridine-2-carboxylate (C7)

Dicarbonylcyclopentadienyl cobalt(I) (10.2 mg, 56.5 μmol) was added to a mixture of C6 (115 mg, 0.520 mmol), acetonitrile (0.30 mL, 5.7 mmol), and xylenes (6 mL). The reaction vial was blanketed with argon, sealed, and heated at 135° C. overnight while being irradiated with a 120 watt daylight LED bulb. The reaction mixture was then concentrated in vacuo, and the residue was purified via silica gel chromatography (Gradient: 0% to 100% ethyl acetate in heptane). The product was obtained as an off-white solid. Yield: 30 mg, 0.11 mmol, 21%. LCMS m/z 263.4 [M+H]$^+$. $^1$H NMR (400 MHz, CDCl$_3$) δ 4.65-4.54 (m, 4H), 2.47 (s, 3H), 2.39 (s, 3H), 2.15 (s, 3H), 1.52 (s, 9H).

Step 3. Synthesis of 4,6,7-trimethyl-2,3-dihydro-1H-pyrrolo[3,4-c]pyridine, dihydrochloride Salt (P4)

A solution of hydrogen chloride in 1,4-dioxane (4 M; 1 mL, 4 mmol) was added to a solution of C7 (30 mg, 0.11 mmol) in dichloromethane (2 mL) and the reaction mixture was stirred at room temperature overnight. It was then concentrated in vacuo and used in further syntheses without purification. Yield: assumed quantitative.

Preparation P5

6,7-Dimethyl-4-(1-methyl-1H-pyrazol-4-yl)-2,3-dihydro-1H-pyrrolo[3,4-c]pyridine, dihydrochloride Salt (P5)

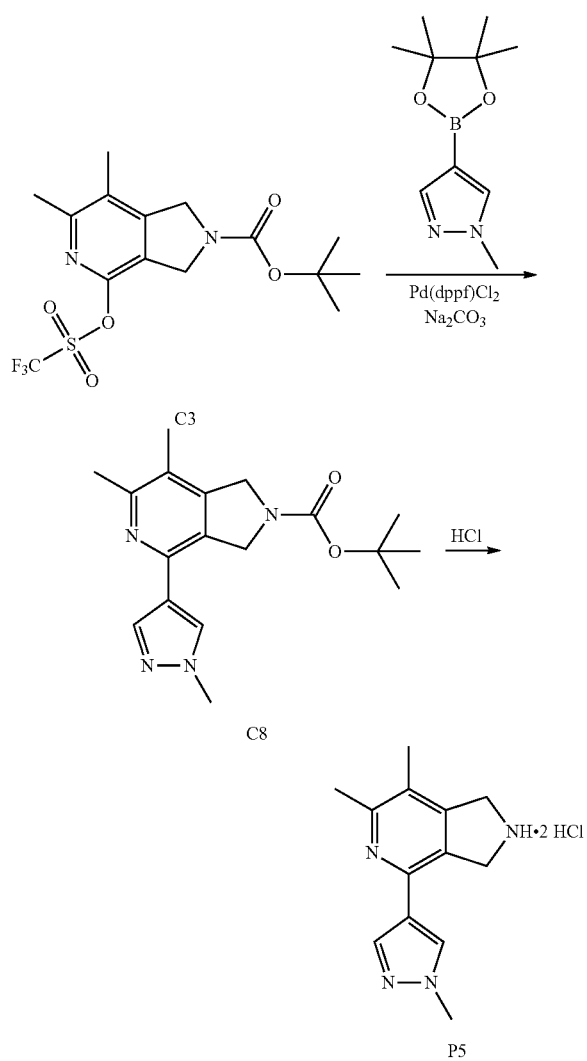

Step 1. Synthesis of tert-butyl 6,7-dimethyl-4-(1-methyl-1H-pyrazol-4-yl)-1,3-dihydro-2H-pyrrolo[3,4-c]pyridine-2-carboxylate (C8)

A mixture of C3 (500 mg, 1.26 mmol), 1-methyl-4-(4,4,5,5-tetramethyl-1,3,2-dioxaborolan-2-yl)-1H-pyrazole (289 mg, 1.39 mmol), and [1,1'-bis(diphenylphosphino)ferrocene]dichloropalladium(II) (46.1 mg, 63.0 μmol), in a mixture of saturated aqueous sodium carbonate solution (5 mL) and 1,4-dioxane (15 mL), was degassed three times and stirred at 100° C. After 16 hours, the reaction mixture was poured into water (50 mL) and extracted with ethyl acetate (3×50 mL). The combined organic layers were washed sequentially with water (100 mL) and with saturated aqueous sodium chloride solution (100 mL), dried over sodium sulfate, filtered, and concentrated in vacuo. Silica gel chromatography (Gradient: 25% to 50% ethyl acetate in petroleum ether) provided the product as a pale yellow solid. From analysis of the $^1$H NMR, this material was presumed to exist as a mixture of rotamers. Yield: 220 mg, 0.670 mmol, 53%. $^1$H NMR (400 MHz, CDCl$_3$) δ [7.94 (s) and 7.89 (s), total 1H], [7.83 (s) and 7.81 (s), total 1H], [4.82 (s), 4.78 (s), 4.65 (s), and 4.60 (s), total 4H], [3.98 (s) and 3.95 (s), total 3H], 2.53 (s, 3H), 2.20 (s, 3H), 1.55 (s, 9H).

Step 2. Synthesis of 6,7-dimethyl-4-(1-methyl-1H-pyrazol-4-yl)-2,3-dihydro-1H-pyrrolo[3,4-c]pyridine, dihydrochloride Salt (P5)

To a solution of C8 (220 mg, 0.670 mmol) in dichloromethane (5 mL) was added hydrogen chloride (solution in ethyl acetate; 5 mL). The reaction mixture was stirred at 20° C. for 30 minutes, whereupon it was concentrated in vacuo to afford the product as a yellow solid, which was used in further syntheses without additional purification. Yield: 175 mg, 0.581 mmol, 87%.

Preparation P6

1-(6,7-Dimethyl-2,3-dihydro-1H-pyrrolo[3,4-c]pyridin-4-yl)-N,N-dimethylmethanamine, trihydrochloride Salt (P6)

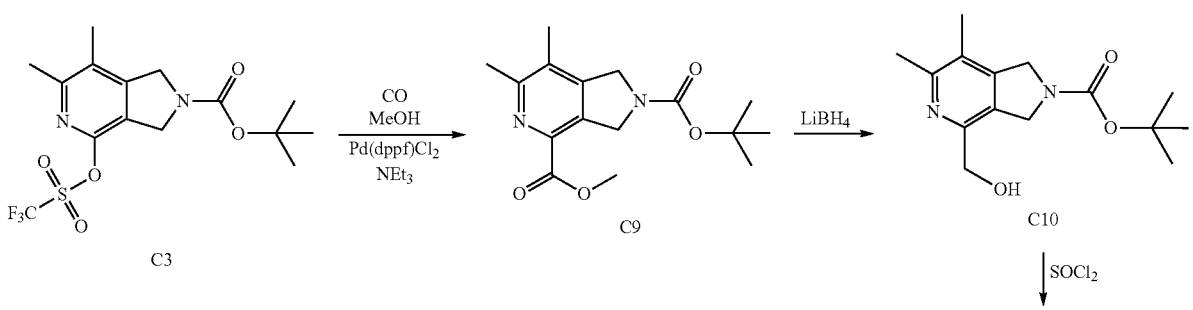

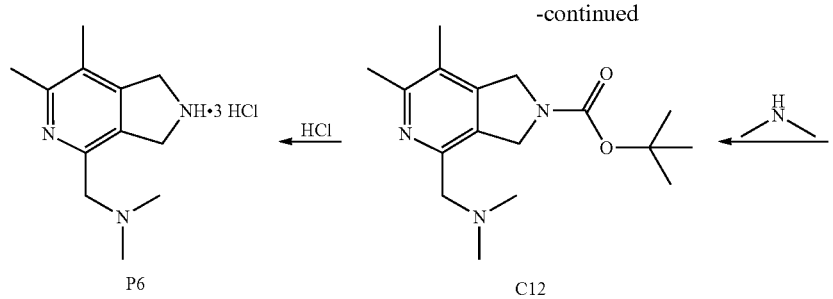
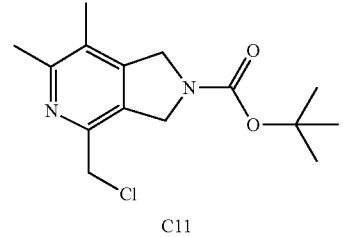

Step 1. Synthesis of 2-tert-butyl 4-methyl 6,7-dimethyl-1,3-dihydro-2H-pyrrolo[3,4-c]pyridine-2,4-dicarboxylate (C9)

[1,1'-Bis(diphenylphosphino)ferrocene]dichloropalladium(II) (369 mg, 0.504 mmol) and triethylamine (1.53 g, 15.1 mmol) were added to a 20° C. suspension of C3 (4.00 g, 10.1 mmol) in methanol (180 mL). The reaction mixture was stirred for 22 hours in an autoclave at 50° C. under 50 psi of carbon monoxide, whereupon it was concentrated in vacuo. The residue was purified using silica gel chromatography (Gradient: 25% to 50% ethyl acetate in petroleum ether) to afford the product as a pale yellow solid. From analysis of the $^1$H NMR, this material was presumed to exist as a mixture of rotamers. Yield: 2.80 g, 9.14 mmol, 90%. $^1$H NMR (400 MHz, CDCl$_3$) δ [5.01 (s) and 4.99 (s), total 2H], [4.68 (s) and 4.62 (s), total 2H], [4.01 (s) and 3.98 (s), total 3H], 2.62 (s, 3H), 2.28 (s, 3H), 1.54 (s, 9H).

Step 2. Synthesis of tert-butyl 4-(hydroxymethyl)-6,7-dimethyl-1,3-dihydro-2H-pyrrolo[3,4-c]pyridine-2-carboxylate (C10)

Lithium borohydride (711 mg, 32.6 mmol) was added to a solution of C9 (2.0 g, 6.53 mmol) in methanol (50 mL), and the reaction mixture was stirred at room temperature (20° C.) for 18 hours. It was then evaporated to dryness, redissolved in dichloromethane (30 mL) and treated with saturated aqueous sodium bicarbonate solution (30 mL); the aqueous layer was extracted with dichloromethane (2×30 mL), and the combined organic layers were washed with saturated aqueous sodium chloride solution, dried over magnesium sulfate, filtered, and concentrated in vacuo. Chromatography on silica gel (Gradient: 50% to 100% ethyl acetate in petroleum ether) provided the product as a white solid. Yield: 1.50 g, 5.39 mmol, 83%. $^1$H NMR (400 MHz, CDCl$_3$) δ 4.67-4.54 (m, 6H), 4.37-4.21 (v br s, 1H), 2.53 (s, 3H), 2.20 (s, 3H), 1.53 (s, 9H).

Step 3. Synthesis of tert-butyl 4-(chloromethyl)-6,7-dimethyl-1,3-dihydro-2H-pyrrolo[3,4-c]pyridine-2-carboxylate (C11)

A solution of thionyl chloride (513 mg, 4.31 mmol) in dichloromethane (5 mL) was added drop-wise to a 0° C. solution of C10 (400 mg, 1.44 mmol) in dichloromethane (45 mL). After the addition had been completed, the reaction mixture was stirred at room temperature (20° C.) for 2 hours, whereupon it was poured into saturated aqueous sodium bicarbonate solution (30 mL). The aqueous layer was extracted with dichloromethane (2×30 mL), and the combined organic layers were washed with saturated aqueous sodium chloride solution, dried over magnesium sulfate, filtered, and concentrated in vacuo to afford the product as a pale yellow oil. Yield: 400 mg, 1.35 mmol, 94%. $^1$H NMR (400 MHz, CDCl$_3$) δ 4.87-4.60 (m, 6H), 2.61 (br s, 3H), 2.24 (s, 3H), 1.54 (s, 9H).

Step 4. Synthesis of tert-butyl 4-[(dimethylamino)methyl]-6,7-dimethyl-1,3-dihydro-2H-pyrrolo[3,4-c]pyridine-2-carboxylate (C12)

Dimethylamine (33% solution in water; 5 mL) was added to a solution of C11 (400 mg, 1.35 mmol) in methanol (5 mL). The reaction mixture was stirred at 22° C. for 17 hours, whereupon it was concentrated in vacuo. Water (20 mL) was added, and the resulting mixture was extracted with ethyl acetate (3×30 mL). The combined organic layers were washed with saturated aqueous sodium chloride solution (30 mL), dried over sodium sulfate, filtered, and concentrated under reduced pressure to provide the product as a pale yellow oil. From analysis of the $^1$H NMR, this material was presumed to exist as a mixture of rotamers. Yield: 400 mg, 1.31 mmol, 97%. $^1$H NMR (400 MHz, CDCl$_3$) δ [4.77 (s), 4.68 (s), 4.62 (s), and 4.57 (s), total 4H], 3.47 (s, 2H), 2.51 (s, 3H), 2.26 (br s, 3H), 2.23 (s, 3H), 2.18 (s, 3H), 1.54 (s, 9H).

Step 5. Synthesis of 1-(6,7-dimethyl-2,3-dihydro-1H-pyrrolo[3,4-c]pyridin-4-yl)-N,N-dimethylmethanamine, trihydrochloride Salt (P6)

A solution of C12 (400 mg, 1.31 mmol) in methanol (8 mL) was treated with hydrogen chloride (4 M solution in methanol; 4.0 mL, 16 mmol), and the reaction mixture was stirred at room temperature (20° C.) for 15 hours. Removal of solvent under reduced pressure provided the product as a pale brown solid. Yield: 300 mg, 0.953 mmol, 73%. $^1$H NMR (400 MHz, CD$_3$OD) δ 4.85 (s, 2H), 4.77 (s, 2H), 4.54 (s, 2H), 3.01 (s, 6H), 2.66 (s, 3H), 2.36 (s, 3H).

Preparation P7 tert-Butyl 4-(difluoromethyl)-6,7-dimethyl-1,3-dihydro-2H-pyrrolo[3,4-c]pyridine-2-carboxylate (P7)

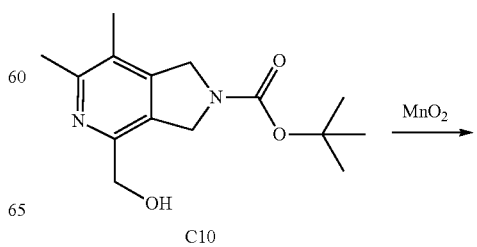

-continued

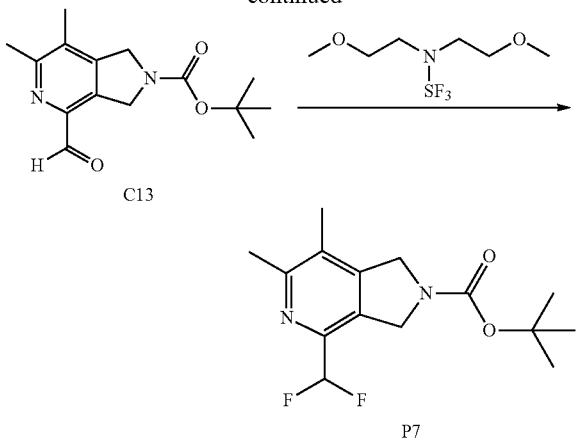

Step 1. Synthesis of tert-butyl 4-formyl-6,7-dimethyl-1,3-dihydro-2H-pyrrolo[3,4-c]pyridine-2-carboxylate (C13)

A mixture of C10 (500 mg, 1.80 mmol) and manganese (IV) oxide (781 mg, 8.98 mmol) in 1,4-dioxane (30 mL) was stirred at 90° C. for 18 hours. The oxidant was then removed via filtration, and the filter cake was washed with dichloromethane (50 mL); the combined filtrates were concentrated in vacuo to afford the product as a pale green solid. From analysis of the $^1$H NMR, this material was presumed to exist as a mixture of rotamers. Yield: 400 mg, 1.45 mmol, 81%. $^1$H NMR (400 MHz, CDCl$_3$) δ 10.08 (s, 1H), [5.01 (s) and 4.96 (s), total 2H], [4.66 (s) and 4.60 (s), total 2H], 2.62 (s, 3H), 2.30 (s, 3H), 1.54 (s, 9H).

Step 2. Synthesis of tert-butyl 4-(difluoromethyl)-6,7-dimethyl-1,3-dihydro-2H-pyrrolo[3,4-c]pyridine-2-carboxylate (P7)

A solution of [bis(2-methoxyethyl)amino]sulfur trifluoride (Deoxo-Fluor®; 641 mg, 2.90 mmol) in dichloromethane (5 mL) was added drop-wise over 5 minutes to a −20° C. solution of C13 (400 mg, 1.45 mmol) in dichloromethane (20 mL). The reaction mixture was allowed to warm from −20° C. to room temperature (10° C. to 15° C.) over 4 hours, whereupon LCMS analysis indicated formation of the product: LCMS m/z 298.8 [M+H]$^+$. Saturated aqueous sodium bicarbonate solution (50 mL) was added, and the resulting mixture was extracted with dichloromethane (3×40 mL). The combined organic layers were washed with saturated aqueous sodium chloride solution (50 mL), dried over sodium sulfate, filtered, and concentrated in vacuo. Purification via silica gel chromatography (Gradient: 17% to 33% ethyl acetate in petroleum ether) afforded the product as a pale yellow solid. Yield: 270 mg, 0.905 mmol, 62%. $^1$H NMR (400 MHz, CDCl$_3$) δ [6.60 (t, $J_{HF}$=55.2 Hz) and 6.59 (t, $J_{HF}$=55.0 Hz), total 1H], [4.90 (s) and 4.84 (s), total 2H], [4.65 (s) and 4.60 (s), total 2H], 2.54 (s, 3H), 2.25 (s, 3H), 1.54 (s, 9H).

Preparation P8

N,1,6,7-Tetramethyl-2,3-dihydro-1H-pyrrolo[3,4-c]pyridin-4-amine, dihydrochloride Salt (P8)

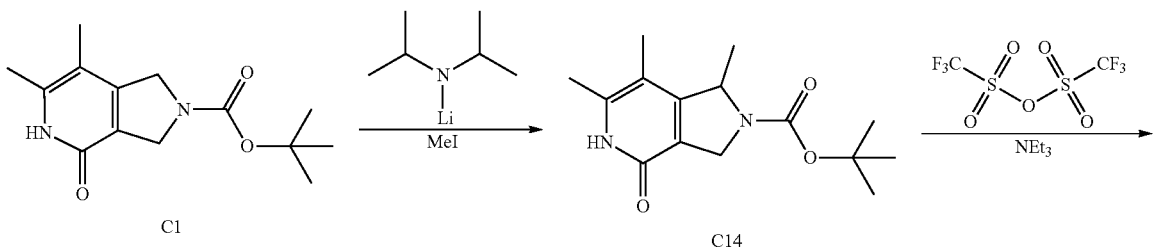

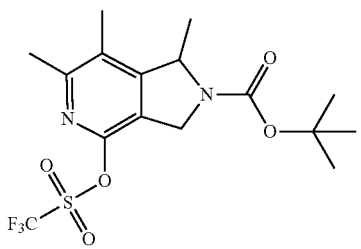

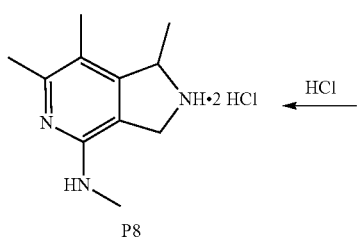

P8

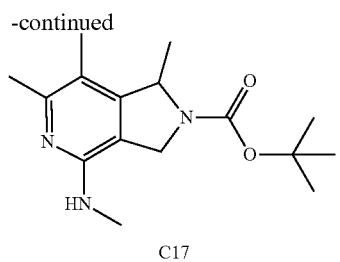

C17

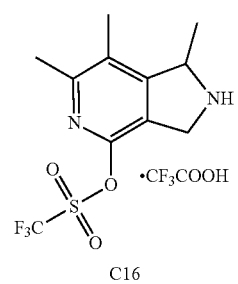

C16

Step 1. Synthesis of tert-butyl 1,6,7-trimethyl-4-oxo-1,3,4,5-tetrahydro-2H-pyrrolo[3,4-c]pyridine-2-carboxylate (C14)

A solution of diisopropylamine (307 µL, 2.19 mmol) in tetrahydrofuran (9.5 mL) was cooled to −78° C. and treated in a drop-wise manner with n-butyllithium (2.7 M solution; 0.77 mL, 2.1 mmol). After the solution had been stirred for 30 minutes at −78° C., it was removed from the cooling bath for approximately 4 minutes, and then recooled, whereupon C1 (250 mg, 0.946 mmol) was added in one portion. Stirring was continued for 30 minutes at −78° C., and then iodomethane (70.7 µL, 1.14 mmol) was added. After 5 minutes, the reaction mixture was removed from the −78° C. bath and stirred for 30 minutes, at which time the reaction was quenched by addition of saturated aqueous ammonium chloride solution, followed by saturated aqueous sodium chloride solution (25 mL). The resulting mixture was partitioned between water (25 mL) and ethyl acetate (50 mL), and the aqueous layer was extracted with ethyl acetate (2×40 mL). The combined organic layers were washed with saturated aqueous sodium chloride solution, dried over sodium sulfate, filtered, and concentrated in vacuo. Chromatography on silica gel (Gradient: 0% to 10% methanol in dichloromethane) provided a mixture of starting material and product as an orange solid (181 mg); this mixture was taken directly to the following step. From analysis of the $^1$H NMR, this material consisted of a roughly 1:1 mixture of C14 and C1; C14 was presumed to exist as a mixture of rotamers. LCMS m/z 279.3 [M+H]$^+$. $^1$H NMR (400 MHz, CDCl$_3$); both starting material and product peaks were tabulated: δ 12.85-12.70 (br s, 2H), [5.13-5.05 (m) and 4.99-4.91 (m), total 1H], 4.69-4.42 (m, 6H), 2.33 (s, 6H), 2.01 (s, 3H), 1.97 (s, 3H), [1.52 (s), 1.52 (s), 1.51 (s), and 1.50 (s), total 18H], [1.45 (d, J=6.2 Hz) and 1.42 (d, J=6.2 Hz), total 3H].

Step 2. Synthesis of tert-butyl 1,6,7-trimethyl-4-{[(trifluoromethyl)sulfonyl]oxy}-1,3-dihydro-2H-pyrrolo[3,4-c]pyridine-2-carboxylate (C15)

Trifluoromethanesulfonic anhydride (118 µL, 0.701 mmol) was added in a drop-wise manner to a 0° C. solution of C14 (from the previous step; 181 mg) and triethylamine (123 µL, 0.882 mmol) in dichloromethane (6 mL). The reaction mixture was stirred for 3 hours at 0° C., whereupon it was concentrated in vacuo and purified by silica gel chromatography (Gradient: 0% to 60% ethyl acetate in heptane) to afford the product as a gum. From analysis of the $^1$H NMR, this material was presumed to exist as a mixture of rotamers. Yield: 91.7 mg, 0.223 mmol, 24% over 2 steps. LCMS m/z 411.3 [M+H]$^+$. $^1$H NMR (400 MHz, CDCl$_3$) δ [5.22 (qd, J=6.4, 2.0 Hz) and 5.08 (qd, J=6.3, 2.2 Hz), total 1H], [4.81 (d, half of AB quartet, J=15.6) and 4.71 (d, half of AB quartet, J=15.3 Hz), total 1H], 4.60 (br d, half of AB quartet, J=15.3 Hz, 1H), 2.48 (s, 3H), 2.25 (s, 3H), [1.54 (s) and 1.52 (s), total 9H], [1.49 (d, J=6.6 Hz) and 1.46 (d, J=6.3 Hz), total 3H].

A small amount of this material was deprotected via dissolution in a 1:1 mixture of trifluoroacetic acid and dichloromethane. After the reaction mixture had been stirred for 30 minutes at room temperature, it was concentrated in vacuo to afford 1,6,7-trimethyl-2,3-dihydro-1H-pyrrolo[3,4-c]pyridin-4-yl trifluoromethanesulfonate, trifluoroacetate salt (C$_{16}$). $^1$H NMR (400 MHz, DMSO-d$_6$) δ 10.0-9.8 (br s, 2H), 5.23 (q, J=6.9 Hz, 1H), 4.72 (AB quartet, J$_{AB}$=14.9 Hz, Δv$_{AB}$=65.6 Hz, 2H), 2.47 (s, 3H), 2.28 (s, 3H), 1.50 (d, J=6.6 Hz, 3H). Two-dimensional NOE study of this material revealed an interaction between the methine proton at the 1-position and the aromatic methyl group at the 7-position; this confirmed the indicated regiochemistry of the methylation reaction in step 1.

Step 3. Synthesis of tert-butyl 1,6,7-trimethyl-4-(methylamino)-1,3-dihydro-2H-pyrrolo[3,4-c]pyridine-2-carboxylate (C17)

A solution of C15 (91.7 mg, 0.223 mmol) and methylamine (2.0 M solution in tetrahydrofuran; 1.79 mL, 3.58 mmol) in tetrahydrofuran (2.0 mL) was stirred at 110° C. for 24 hours. After the reaction mixture had been concentrated in vacuo, the residue was purified via silica gel chromatography (Gradient: 0% to 15% methanol in dichloromethane) to afford the product as a solid. From analysis of the $^1$H NMR, this material was presumed to exist as a mixture of rotamers. Yield: 48 mg, 0.16 mmol, 72%. $^1$H NMR (400 MHz, CDCl$_3$) δ [5.09 (br q, J=6 Hz) and 4.96 (br q, J=6 Hz), total 1H], [4.50 (d, half of AB quartet, J=13.7 Hz) and 4.43 (d, half of AB quartet, J=13.7 Hz), total 1H], [4.36 (br d, half of AB quartet, J=13.3 Hz) and 4.35 (br d, half of AB quartet, J=13.3 Hz), total 1H], 3.81-3.67 (br m, 1H), [3.04 (s) and 3.03 (s), total 3H], 2.40 (s, 3H), 2.10 (s, 3H), [1.53 (s) and 1.51 (s), total 9H], [1.44 (d, J=6.2 Hz) and 1.40 (d, J=6.2 Hz), total 3H].

Step 4. Synthesis of N, 1,6,7-tetramethyl-2,3-dihydro-1H-pyrrolo[3,4-c]pyridin-4-amine, dihydrochloride Salt (P8)

Hydrogen chloride (4.0 M solution in 1,4-dioxane; 2.06 mL, 8.24 mmol) was added in a drop-wise manner to an ice-cooled flask containing C17 (48 mg, 0.16 mmol). The cooling bath was removed, and the reaction was monitored via thin-layer chromatography; when the starting material had been consumed, methanol (1 mL) was added, and the resulting mixture was concentrated in vacuo, affording the product as a cream-colored solid. Yield: 38 mg, 0.14 mmol, 88%. $^1$H NMR (400 MHz, CD$_3$OD) δ 5.23 (br q, J=7 Hz, 1H), 4.59 (br AB quartet, J$_{AB}$=14.4 Hz, Δv$_{AB}$=44.1 Hz, 2H), 3.15 (s, 3H), 2.58 (s, 3H), 2.21 (s, 3H), 1.64 (d, J=6.6 Hz, 3H).

Preparation P9

6,7-Dimethyl-2,3-dihydro-1H-pyrrolo[3,4-c]pyridine, hydrochloride Salt (P9)

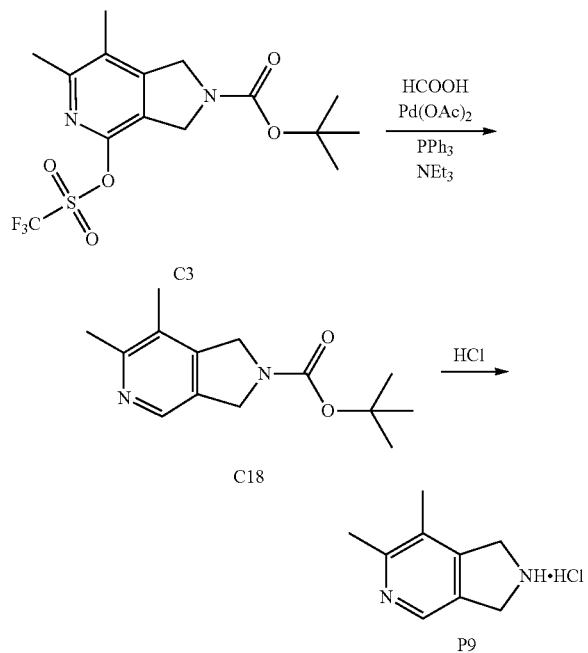

Step 1. Synthesis of tert-butyl 6,7-dimethyl-1,3-dihydro-2H-pyrrolo[3,4-c]pyridine-2-carboxylate (C18)

To a solution of C3 (2.50 g, 6.31 mmol) in N,N-dimethylformamide (30 mL) were added triphenylphosphine (165 mg, 0.629 mol), palladium(II) acetate (70.8 mg, 0.315 mol), triethylamine (1.91 g, 18.9 mmol), and formic acid (581 mg, 12.6 mmol). After the reaction mixture had been purged with nitrogen, it was heated to 60° C. for 90 minutes, whereupon it was poured into water (25 mL). The aqueous layer was extracted with ethyl acetate (2×20 mL) and the combined organic layers were washed sequentially with water (3×20 mL) and with saturated aqueous sodium chloride solution (2×20 mL), dried over magnesium sulfate, filtered, and concentrated in vacuo. The residue was combined with material from a similar reaction carried out using C3 (100 mg, 0.25 mmol) and purified via silica gel chromatography (Eluent: 1:1 ethyl acetate/petroleum ether). The product was obtained as a pale yellow solid. From analysis of the $^1$H NMR, this material was presumed to exist as a mixture of rotamers. Combined yield: 1.45 g, 5.84 mmol, 89%. $^1$H NMR (400 MHz, CDCl$_3$) δ [8.27 (s) and 8.23 (s), total 1H], [4.71 (s), 4.68 (s), 4.64 (s), and 4.58 (s), total 4H], 2.52 (s, 3H), 2.21 (s, 3H), [1.53 (s) and 1.52 (s), total 9H].

Step 2. Synthesis of 6,7-dimethyl-2,3-dihydro-1H-pyrrolo[3,4-c]pyridine, hydrochloride Salt (P9)

Hydrogen chloride (4 M solution in methanol; 2 mL, 8 mmol) was added to a solution of C18 (1.45 g, 5.84 mmol) in methanol (5 mL), and the reaction mixture was stirred at room temperature (20° C.) for 1.5 hours. Removal of solvent in vacuo provided the product as a white solid. Yield: 950 mg, 5.14 mmol, 88%. $^1$H NMR (400 MHz, DMSO-d$_6$) δ 10.55-10.35 (br s, 2H), 8.58 (s, 1H), 4.74 (s, 2H), 4.67 (s, 2H), 2.67 (s, 3H), 2.33 (s, 3H).

Preparation P10

4-Methoxy-6,7-dimethyl-2,3-dihydro-1H-pyrrolo[3,4-c]pyridine, di(trifluoroacetate) Salt (P10)

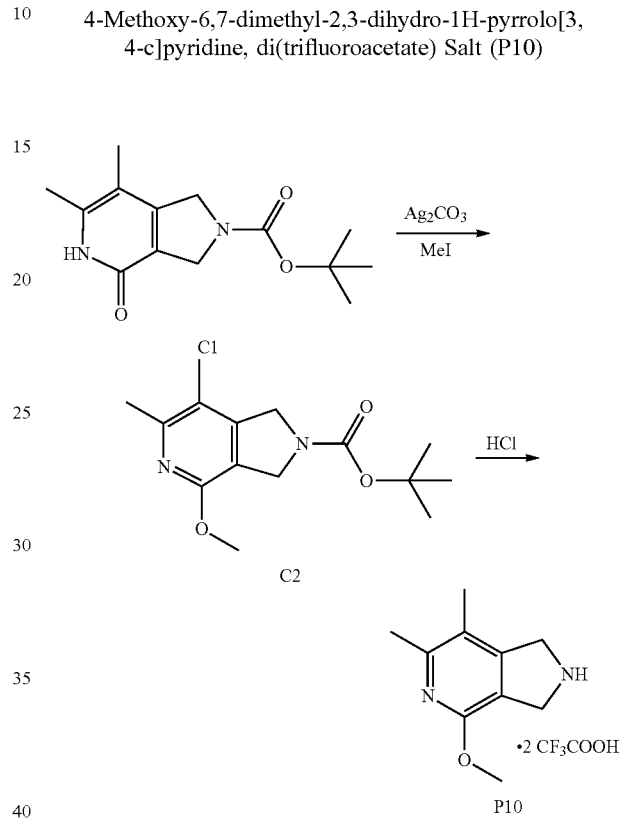

Step 1. Alternate synthesis of tert-butyl 4-methoxy-6,7-dimethyl-1,3-dihydro-2H-pyrrolo[3,4-c]pyridine-2-carboxylate (C2)

To a suspension of C1 (300 mg, 1.13 mmol) in chloroform (4 mL) were added iodomethane (483 mg, 3.40 mmol) and silver carbonate (469 mg, 1.70 mmol). The reaction mixture was heated at 50° C. for 18 hours, whereupon it was filtered. The filtrate was concentrated in vacuo, and the residue was purified using silica gel chromatography (Eluent: 17% ethyl acetate in petroleum ether), affording the product as a white solid. From analysis of the $^1$H NMR, this material was presumed to exist as a mixture of rotamers. Yield: 250 mg, 0.898 mmol, 79%. $^1$H NMR (400 MHz, CDCl$_3$) δ 4.62-4.51 (m, 4H), [3.94 (s) and 3.94 (s), total 3H], 2.41 (s, 3H), 2.11 (s, 3H), [1.53 (s) and 1.52 (s), total 9H].

Step 2. Synthesis of 4-methoxy-6,7-dimethyl-2,3-dihydro-1H-pyrrolo[3,4-c]pyridine, di(trifluoroacetate) Salt (P10)

Trifluoroacetic acid (2 mL) was added to a solution of C2 (250 mg, 0.898 mmol) in dichloromethane (6 mL). The reaction mixture was stirred at 22° C. for 2 hours, whereupon it was concentrated in vacuo to provide the product as a pale yellow oil, which was used without additional purification. This material exhibited some extraneous signals in the NMR spectrum. Yield: 370 mg, quantitative. $^1$H NMR (400 MHz, CDCl$_3$), product peaks only: δ 4.67 (s, 4H), 4.05 (s, 3H), 2.50 (s, 3H), 2.18 (s, 3H).

Preparation P11

4-(Methoxymethyl)-6,7-dimethyl-2,3-dihydro-1H-pyrrolo[3,4-c]pyridine, dihydrochloride Salt (P11)

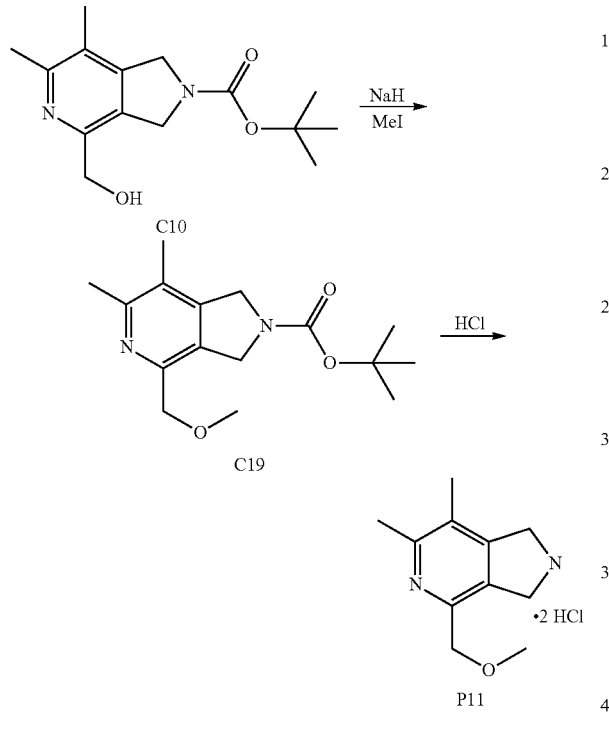

Step 1. Synthesis of tert-butyl 4-(methoxymethyl)-6,7-dimethyl-1,3-dihydro-2H-pyrrolo[3,4-c]pyridine-2-carboxylate (C19)

Sodium hydride (69.0 mg, 2.88 mmol) was added to a 0° C. suspension of C10 (400 mg, 1.44 mmol) in N,N-dimethylformamide (2 mL). The reaction mixture was stirred for 30 minutes, whereupon iodomethane (306 mg, 2.16 mmol) was added, and stirring was continued for 2 hours at room temperature (24° C.). The reaction mixture was poured into water (20 mL) and extracted with ethyl acetate (3×20 mL); concentrated of the combined organic layers in vacuo afforded the product as a pale yellow solid. From analysis of the $^1$H NMR, this material was presumed to exist as a mixture of rotamers. Yield: 350 mg, 1.20 mmol, 83%. $^1$H NMR (400 MHz, CDCl$_3$) δ [4.77 (s), 4.71 (s), 4.63 (s), and 4.57 (s), total 4H], [4.53 (s) and 4.51 (s), total 2H], 3.41 (s, 3H), 2.51 (s, 3H), 2.19 (s, 3H), 1.53 (s, 9H).

Step 2. Synthesis of 4-(methoxymethyl)-6,7-dimethyl-2,3-dihydro-1H-pyrrolo[3,4-c]pyridine, dihydrochloride Salt (P11)

Hydrogen chloride (4 M solution in methanol; 3 mL, 12 mmol) was added to a solution of C19 (350 mg, 1.20 mmol) in methanol (6 mL), and the reaction mixture was stirred at room temperature (20° C.) for 15 hours. Removal of solvent under reduced pressure afforded the product as an off-white solid. Yield: 300 mg, 1.13 mmol, 94%. $^1$H NMR (400 MHz, CD$_3$OD) δ 4.97-4.81 (m, 6H, assumed; partially obscured by water peak), 3.54 (s, 3H), 2.79 (s, 3H), 2.44 (s, 3H).

Preparation P12

4-(Difluoromethoxy)-6,7-dimethyl-2,3-dihydro-1H-pyrrolo[3,4-c]pyridine, hydrochloride Salt (P12)

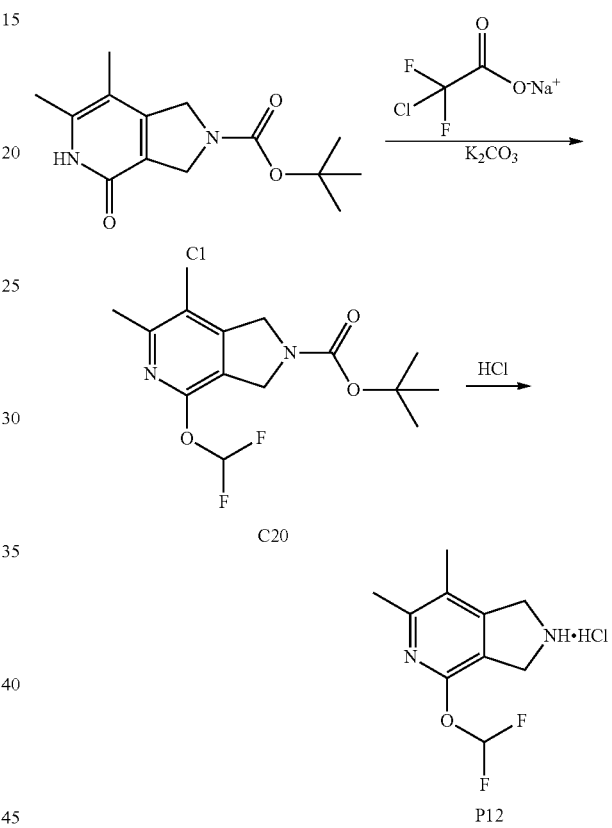

Step 1. Synthesis of tert-butyl 4-(difluoromethoxy)-6,7-dimethyl-1,3-dihydro-2H-pyrrolo[3,4-c]pyridine-2-carboxylate (C20)

Sodium chloro(difluoro)acetate (577 mg, 3.78 mmol) and potassium carbonate (392 mg, 2.84 mmol) were added to a solution of C1 (500 mg, 1.89 mmol) in N,N-dimethylformamide (10 mL) at room temperature (15° C.). The reaction mixture was stirred at 95° C. for 1 hour, whereupon water (20 mL) was added, and the resulting mixture was extracted with ethyl acetate (3×30 mL). The combined organic layers were washed sequentially with water (3×50 mL) and with saturated aqueous sodium chloride solution (50 mL), dried over sodium sulfate, filtered, and concentrated in vacuo. Silica gel chromatography (Eluent: 10:1 petroleum ether/ ethyl acetate) afforded the product as a white solid. From analysis of the $^1$H NMR, this material was presumed to exist as a mixture of rotamers. Yield: 300 mg, 0.954 mmol, 50%. $^1$H NMR (400 MHz, CDCl$_3$) δ [7.55 (t, $J_{HF}$=73.5 Hz) and 7.52 (t, $J_{HF}$=73.3 Hz), total 1H], 4.68-4.55 (m, 4H), 2.42 (s, 3H), 2.15 (s, 3H), 1.53 (s, 9H).

Step 2. Synthesis of 4-(difluoromethoxy)-6,7-dimethyl-2,3-dihydro-1H-pyrrolo[3,4-c]pyridine, hydrochloride Salt (P12)

A solution of hydrogen chloride in ethyl acetate (10 mL) was combined with C20 (300 mg, 0.954 mmol), and the reaction mixture was stirred at 20° C. for 30 minutes. Removal of solvent in vacuo provided the product as a white solid. Yield: 150 mg, 0.598 mmol, 63%. $^1$H NMR (400 MHz, CD$_3$OD) δ 7.62 (t, $J_{HF}$=72.8 Hz, 1H), 4.66 (s, 2H), 4.61 (s, 2H), 2.47 (s, 3H), 2.24 (s, 3H).

Example 1

5,6,7-Trimethyl-2-{[1-(pyridin-3-yl)azetidin-3-yl]acetyl}-1,2,3,5-tetrahydro-4H-pyrrolo[3,4-c]pyridin-4-one (1)

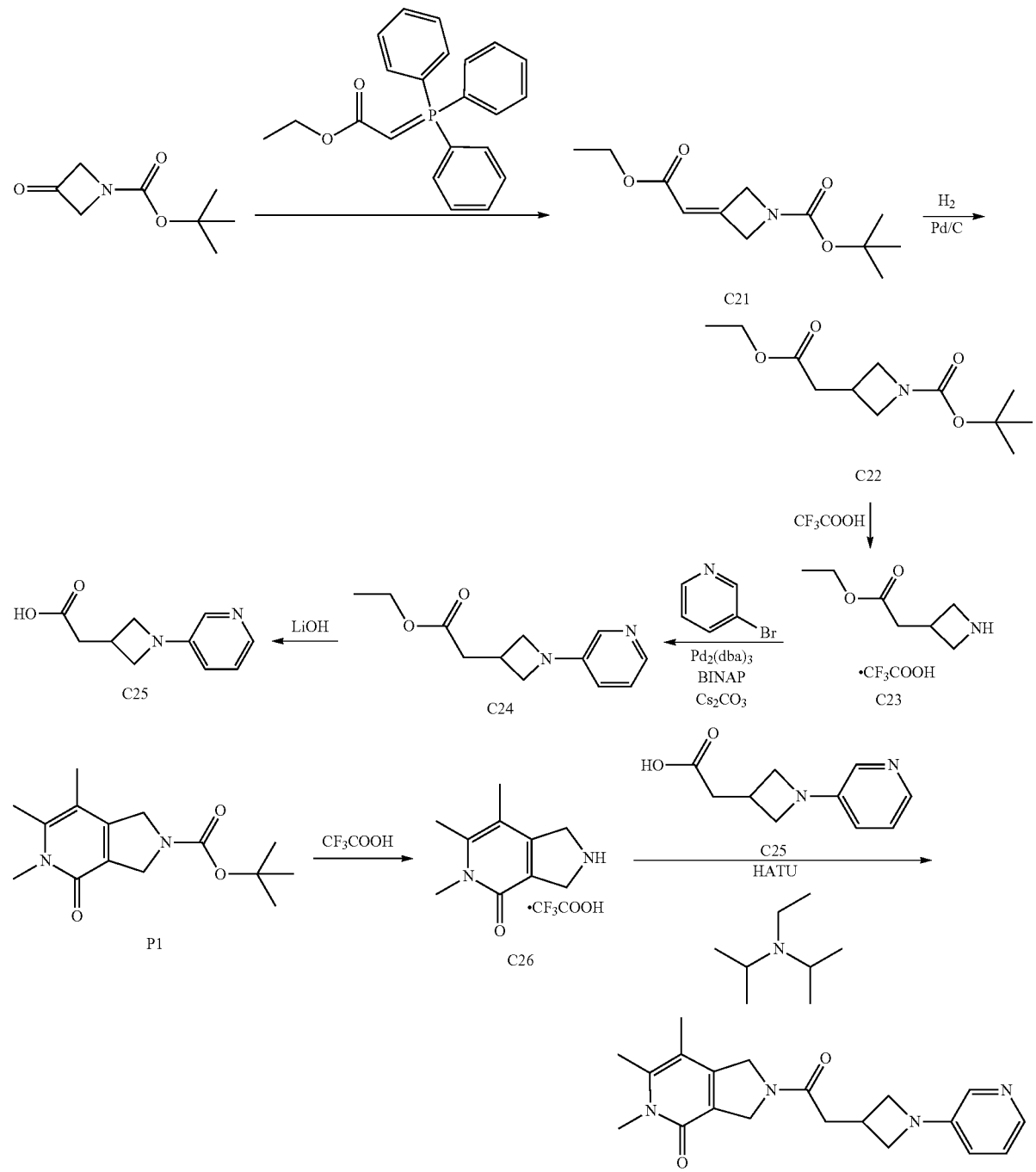

Step 1. Synthesis of tert-butyl 3-(2-ethoxy-2-oxo-ethylidene)azetidine-1-carboxylate (C21)

tert-Butyl 3-oxoazetidine-1-carboxylate (100 g, 584 mmol) was dissolved in dichloromethane (750 mL), cooled in an ice bath, and vigorously stirred while (carboethoxymethylene)triphenylphosphorane (220 g, 631 mmol) was added portion-wise over 15 minutes. The reaction mixture was then heated to 40° C. for 4 hours, whereupon most of the dichloromethane was removed in vacuo. The resulting thick slurry was diluted with a mixture of hexanes and tert-butyl methyl ether (2:1, 1 L), and stirred at room temperature for 1.5 hours. Triphenylphosphine oxide was removed via filtration; the filter cake was washed with a 2:1 mixture of hexanes and tert-butyl methyl ether, and the combined filtrates were concentrated in vacuo. Silica gel chromatography (Eluent: 2:1 hexanes/tert-butyl methyl ether) afforded the product as a clear, slightly yellow oil. Yield: 141.8 g, quantitative.

Step 2. Synthesis of tert-butyl 3-(2-ethoxy-2-oxo-ethyl)azetidine-1-carboxylate (C22)

A solution of C21 (141 g, 584 mmol) in tert-butyl methyl ether (500 mL) was placed in a Parr bottle and treated with 10% palladium on carbon (~50% water by weight; 2.5 g). The reaction vessel was evacuated and charged with nitrogen. This evacuation cycle was repeated several times, and then the bottle was pressurized to 40 psi with hydrogen and shaken for 30 minutes, whereupon the vessel was purged with additional nitrogen/vacuum cycles. The reaction mixture was filtered through a pad of diatomaceous earth/powdered cellulose, which was subsequently rinsed with tert-butyl methyl ether. The combined filtrates were concentrated in vacuo to provide the product as a clear, colorless oil. Yield: 140.1 g, 576 mmol, 99%. $^1$H NMR (400 MHz, DMSO-$d_6$) δ 4.04 (q, J=7.0 Hz, 2H), 3.99-3.85 (m, 2H), 3.58-3.45 (m, 2H), 2.84-2.71 (m, 1H), 2.62 (d, J=7.4 Hz, 2H), 1.36 (s, 9H), 1.17 (t, J=7.0 Hz, 3H).

Step 3. Synthesis of ethyl azetidin-3-ylacetate, trifluoroacetate Salt (C23)

Trifluoroacetic acid (60 mL) was added in a drop-wise manner to a solution of C22 (15.0 g, 61.6 mmol) in dichloromethane (200 mL) and the reaction mixture was stirred at room temperature for 2 hours. Removal of solvents in vacuo afforded the product as a pale yellow oil. Yield: 15.85 g, 61.62 mmol, quantitative. $^1$H NMR (400 MHz, CDCl$_3$) δ 8.23-7.99 (br s, 1H), 7.99-7.77 (br s, 1H), 4.41-4.27 (m, 2H), 4.16 (q, J=7.2 Hz, 2H), 4.11-3.99 (m, 2H), 3.40-3.25 (m, 1H), 2.74 (d, J=7.2 Hz, 2H), 1.26 (t, J=7.2 Hz, 3H).

Step 4. Synthesis of ethyl [1-(pyridin-3-yl)azetidin-3-yl]acetate (C24)

A mixture of C23 (10.0 g, 38.9 mmol), 3-bromopyridine (16.6 g, 105 mmol), 1,1'-binaphthalene-2,2'-diylbis(diphenylphosphane) (8.7 g, 14 mmol), tris(dibenzylideneacetone)dipalladium(0) (Pd$_2$(dba)$_3$; 6.4 g, 7.0 mmol), and cesium carbonate (91.0 g, 279 mmol) in toluene (300 mL) was heated at 90° C. for 16 hours. Most of the toluene was removed via concentration in vacuo, and the residue was diluted with water (3×200 mL) and extracted with ethyl acetate (3×100 mL). The combined organic layers were washed with saturated aqueous sodium chloride solution (2×100 mL), dried over sodium sulfate, filtered, and concentrated under reduced pressure. Silica gel chromatography (Gradient: 17% to 20% ethyl acetate in petroleum ether) provided the product as a brown oil. Yield: 4.0 g, 18 mmol, 46%. LCMS m/z 220.9 [M+H]$^+$. $^1$H NMR (400 MHz, CDCl$_3$) δ 8.01 (dd, J=4.6, 1.3 Hz, 1H), 7.85 (d, J=2.9 Hz, 1H), 7.10 (dd, J=8.2, 4.7 Hz, 1H), 6.71 (ddd, J=8.3, 2.8, 1.4 Hz, 1H), 4.16 (q, J=7.2 Hz, 2H), 4.11 (dd, J=7.9, 7.5 Hz, 2H), 3.61 (dd, J=7.2, 5.6 Hz, 2H), 3.20-3.08 (m, 1H), 2.72 (d, J=7.8 Hz, 2H), 1.27 (t, J=7.2 Hz, 3H).

Step 5. Synthesis of [1-(pyridin-3-yl)azetidin-3-yl] acetic Acid (C25)

Lithium hydroxide (652 mg, 27.2 mmol) was added to a solution of C24 (3.00 g, 13.6 mmol) in a mixture of methanol (20 mL) and water (5 mL). The reaction mixture was stirred at room temperature for 2 hours, whereupon it was cooled to 0° C., and concentrated hydrochloric acid was added until the pH of the reaction mixture reached 7. Concentration in vacuo afforded the product. Yield: 3.3 g, assumed quantitative. $^1$H NMR (400 MHz, DMSO-$d_6$) δ 7.91-7.82 (m, 1H), 7.75 (s, 1H), 7.17-7.07 (m, 1H), 6.80-6.71 (m, 1H), 3.97 (dd, J=7, 7 Hz, 2H), 3.48 (dd, J=6, 6 Hz, 2H), 3.02-2.89 (m, 1H), 2.5 (2H, assumed; obscured by solvent peak).

Step 6. Synthesis of 5,6,7-trimethyl-1,2,3,5-tetrahydro-4H-pyrrolo[3,4-c]pyridin-4-one, trifluoroacetate Salt (C26)

Trifluoroacetic acid (2 mL) was added to a solution of P1 (125 mg, 0.449 mmol) in dichloromethane (6 mL) at 27° C. The reaction mixture was stirred at 27° C. for 2 hours, whereupon it was concentrated in vacuo to provide the product as a green oil (260 mg). A portion of this material was used directly in the next step.

Step 7. Synthesis of 5,6,7-trimethyl-2-{[1-(pyridin-3-yl)azetidin-3-yl]acetyl}-1,2,3,5-tetrahydro-4H-pyrrolo[3,4-c]pyridin-4-one (1)

O-(7-Azabenzotriazol-1-yl)-N,N,N',N'-tetramethyluronium hexafluorophosphate (HATU; 89.0 mg, 0.234 mmol) and C26 (from the previous step; 54.7 mg, 594 µmol) were added to a solution of C25 (30.0 mg, 0.156 mmol) in N,N-dimethylformamide (1 mL) at room temperature (24° C.). N,N-Diisopropylethylamine (121 mg, 0.936 mmol) was added, and the reaction mixture was stirred at room temperature (24° C.) for 10 minutes. The reaction mixture was directly purified via reversed-phase HPLC (Column: Phenomenex Gemini C18, 5 µm; Mobile phase A: 0.01 M aqueous ammonium bicarbonate solution; Mobile phase B: acetonitrile; Gradient: 14% to 44% B) to afford the product as a white solid. From analysis of the $^1$H NMR, this material was presumed to exist as a mixture of rotamers. Yield: 12.7 mg, 36 µmol, 38% over 2 steps. LCMS m/z 353.0 [M+H]$^+$. $^1$H NMR (400 MHz, CDCl$_3$) δ 8.00 (dd, J=4.7, 1.3 Hz, 1H), 7.86 (d, J=2.6 Hz, 1H), 7.10 (dd, J=8.2, 4.7 Hz, 1H), 6.72 (ddd, J=8.2, 2.8, 1.3 Hz, 1H), 4.74-4.67 (m, 4H), 4.21-4.14 (m, 2H), 3.68-3.62 (m, 2H), 3.60 (s, 3H), 3.31-3.18 (m, 1H), 2.79 (d, J=7.6 Hz, 2H), 2.35 (br s, 3H), [2.06 (s) and 2.05 (s), total 3H].

Example 2

1-[6,7-Dimethyl-4-(methylamino)-1,3-dihydro-2H-pyrrolo[3,4-c]pyridin-2-yl]-2-[1-(1,2,4-thiadiazol-5-yl)azetidin-3-yl]ethanone (2)

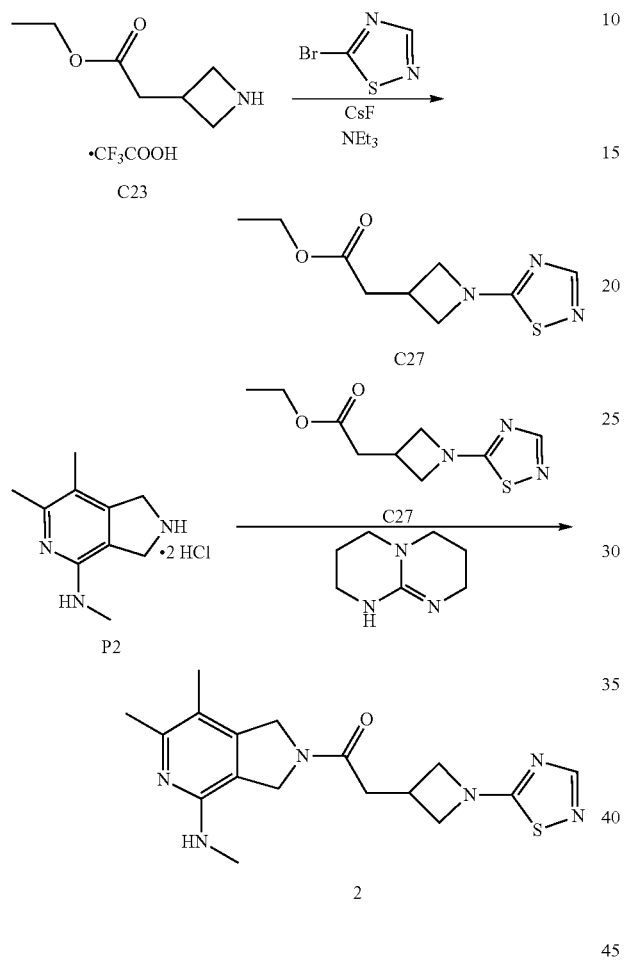

Step 1. Synthesis of ethyl [1-(1,2,4-thiadiazol-5-yl)azetidin-3-yl]acetate (C27)

A mixture of 5-bromo-1,2,4-thiadiazole (1.05 g, 6.36 mmol), C23 (2.00 g, 7.78 mmol), cesium fluoride (967 mg, 6.37 mmol), and triethylamine (1.93 g, 19.1 mmol) in dimethyl sulfoxide (15 mL) was stirred at 100° C. for 12 hours. The reaction mixture was then poured into water (30 mL), and extracted with dichloromethane (3×100 mL); the combined organic layers were washed sequentially with water (3×100 mL) and saturated aqueous sodium chloride solution (100 mL), dried over sodium sulfate, filtered, and concentrated in vacuo. Chromatography on silica gel (Gradient: 25% to 67% ethyl acetate in petroleum ether) afforded the product as a yellow oil. Yield: 1.10 g, 4.84 mmol, 76%. $^1$H NMR (400 MHz, CDCl$_3$) δ 7.93 (s, 1H), 4.37-4.31 (m, 2H), 4.15 (q, J=7.2 Hz, 2H), 3.89 (dd, J=9.1, 5.6 Hz, 2H), 3.32-3.21 (m, 1H), 2.74 (d, J=7.9 Hz, 2H), 1.26 (t, J=7.2 Hz, 3H).

Step 2. Synthesis of 1-[6,7-dimethyl-4-(methylamino)-1,3-dihydro-2H-pyrrolo[3,4-c]pyridin-2-yl]-2-[1-(1,2,4-thiadiazol-5-yl)azetidin-3-yl]ethanone (2)

A mixture of P2 (100 mg, 0.400 mmol), C27 (90.8 mg, 0.400 mmol), and 1,3,4,6,7,8-hexahydro-2H-pyrimido[1,2-a]pyrimidine (167 mg, 1.20 mmol) in N,N-dimethylformamide (5 mL) was stirred at 85° C. for 16 hours. The reaction mixture was then poured into water (10 mL) and extracted with ethyl acetate (3×10 mL). The combined organic layers were washed sequentially with water (3×10 mL) and saturated aqueous sodium chloride solution (10 mL), dried over sodium sulfate, filtered, and concentrated in vacuo. Purification of the residue via reversed-phase HPLC (Column: Waters XBridge C18 OBD, 5 μm; Mobile phase A: water containing 0.05% ammonium hydroxide; Mobile phase B: acetonitrile; Gradient: 17% to 32% B) afforded the product as a white solid. From analysis of the $^1$H NMR, this material was presumed to exist as a mixture of rotamers. Yield: 21.6 mg, 60.2 μmol, 15%. LCMS m/z 359.1 [M+H]$^+$. $^1$H NMR (400 MHz, CDCl$_3$) δ 7.94 (s, 1H), 4.66 (br s, 2H), 4.60 (br s, 1H), 4.57 (br s, 1H), 4.43 (dd, J=8.3, 8.3 Hz, 2H), 3.95-3.88 (m, 2H), 3.46-3.35 (m, 1H), 3.04 (d, J=4.5 Hz, 3H), [2.84 (d, J=7.6 Hz) and 2.82 (d, J=7.6 Hz), total 2H], 2.41 (s, 3H), [2.08 (s) and 2.08 (s), total 3H].

Example 3

2-{1-[2-(Difluoromethoxy)pyridin-4-yl]azetidin-3-yl}-1-[6,7-dimethyl-4-(methylamino)-1,3-dihydro-2H-pyrrolo[3,4-c]pyridin-2-yl]ethanone (3)

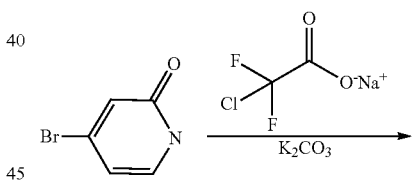

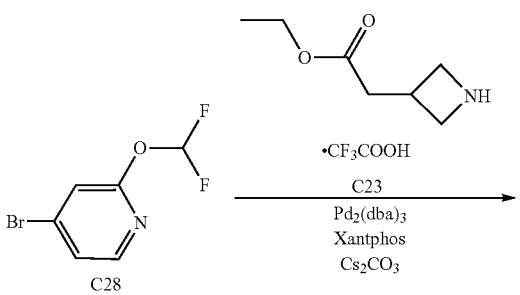

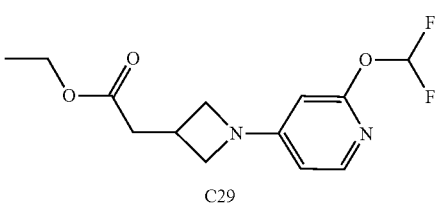

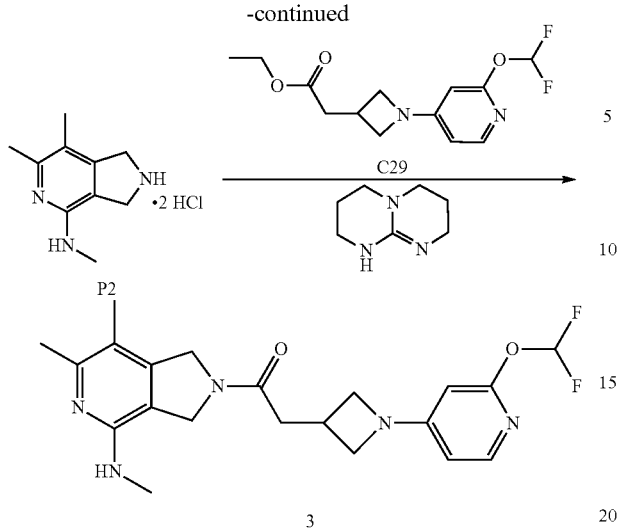

Step 1. Synthesis of 4-bromo-2-(difluoromethoxy)pyridine (C28)

Sodium chloro(difluoro)acetate (5.26 g, 34.5 mmol) and potassium carbonate (3.57 g, 25.8 mmol) were added to a solution of 4-bromopyridin-2(1H)-one (3.00 g, 17.2 mmol) in N,N-dimethylformamide (30 mL), and the reaction mixture was stirred at 95° C. for 2 hours. Water (100 mL) was added, and the resulting mixture was extracted with ethyl acetate (3×50 mL). The combined organic layers were washed sequentially with water (200 mL) and with saturated aqueous sodium chloride solution (150 mL), dried over sodium sulfate, filtered, and concentrated in vacuo. Silica gel chromatography (Eluent: 15:1 petroleum ether/ethyl acetate) afforded the product as a pale yellow oil. Yield: 1.5 g, 6.7 mmol, 39%. $^1$H NMR (400 MHz, CDCl$_3$) δ 8.04 (d, J=5.5 Hz, 1H), 7.44 (t, J$_{HF}$=72.6 Hz, 1H), 7.27 (dd, J=5.4, 1.6 Hz, 1H), 7.12 (br d, J=1.5 Hz, 1H).

Step 2. Synthesis of ethyl {1-[2-(difluoromethoxy)pyridin-4-yl]azetidin-3-yl}acetate (C29)

A mixture of C23 (120 mg, 0.467 mmol), C28 (105 mg, 0.469 mmol), tris(dibenzylideneacetone)dipalladium(0) (12.8 mg, 14.0 μmol), 4,5-bis(diphenylphosphino)-9,9-dimethylxanthene (Xantphos; 17.8 mg, 30.8 μmol), and cesium carbonate (608 mg, 1.87 mmol) in 1,4-dioxane (5 mL) was stirred at 100° C. for 16 hours. After cooling to room temperature, the reaction mixture was filtered, and the filtrate was concentrated. The residue was purified using silica gel chromatography (Eluent: 20:1 petroleum ether/ethyl acetate) to provide the product as a yellow oil. Yield: 50 mg, 0.17 mmol, 36%. $^1$H NMR (400 MHz, CDCl$_3$) δ 7.81 (d, J=5.9 Hz, 1H), 7.42 (t, J$_{HF}$=73.7 Hz, 1H), 6.08 (dd, J=5.8, 2.1 Hz, 1H), 5.75 (d, J=2.0 Hz, 1H), 4.20-4.11 (m, 4H), 3.66 (dd, J=8.0, 5.5 Hz, 2H), 3.20-3.09 (m, 1H), 2.71 (d, J=7.9 Hz, 2H), 1.28 (t, J=7.1 Hz, 3H).

Step 3. Synthesis of 2-{1-[2-(difluoromethoxy)pyridin-4-yl]azetidin-3-yl}-1-[6,7-dimethyl-4-(methylamino)-1,3-dihydro-2H-pyrrolo[3,4-c]pyridin-2-yl]ethanone (3)

A mixture of P2 (100 mg, 0.400 mmol), C29 (162 mg, 0.566 mmol), and 1,3,4,6,7,8-hexahydro-2H-pyrimido[1,2-a]pyrimidine (314 mg, 2.26 mmol) in N,N-dimethylformamide (4 mL) was heated at 80° C. for 16 hours. The reaction mixture was purified using preparative HPLC to afford the product as a white solid. From analysis of the $^1$H NMR, this material was presumed to exist as a mixture of rotamers. Yield: 54.3 mg, 0.130 mmol, 32%. LCMS m/z 418.2 [M+H]$^+$. $^1$H NMR (400 MHz, CDCl$_3$) δ 7.81 (d, J=6.0 Hz, 1H), 7.43 (t, J$_{HF}$=73.8 Hz, 1H), 6.09 (dd, J=5.5, 2.0 Hz, 1H), 5.76 (d, J=1.5 Hz, 1H), [4.66 (s), 4.60 (s), and 4.58 (s), total 4H], 4.22 (br dd, J=8.0, 8.0 Hz, 2H), 3.71-3.64 (m, 2H), 3.34-3.22 (m, 1H), 3.07-3.01 (m, 3H), 2.83-2.76 (m, 2H), 2.41 (s, 3H), [2.09 (s) and 2.08 (s), total 3H].

Example 4

1-[6,7-Dimethyl-4-(methylamino)-1,3-dihydro-2H-pyrrolo[3,4-c]pyridin-2-yl]-2-[1-(pyridin-3-yl)azetidin-3-yl]ethanone (4)

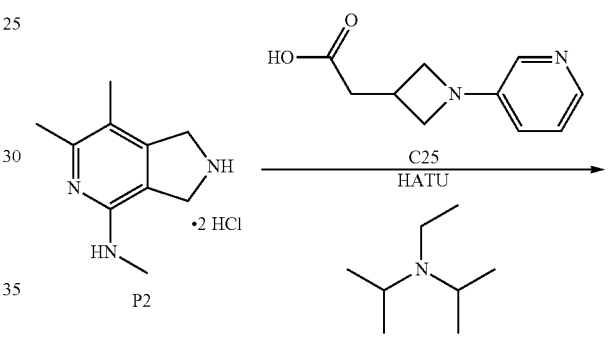

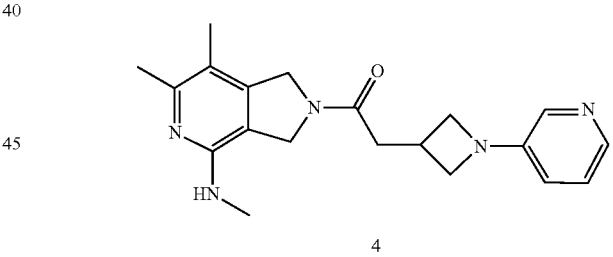

To a suspension of P2 (64.0 mg, 0.256 mmol) in N,N-dimethylformamide (3 mL) were added O-(7-azabenzotriazol-1-yl)-N,N,N',N'-tetramethyluronium hexafluorophosphate (171 mg, 0.450 mmol) and C25 (57.6 mg, 0.300 mmol) at room temperature (16° C.). N,N-Diisopropylethylamine (116 mg, 0.897 mmol) was then added, and the reaction mixture was stirred at room temperature (16° C.) for another 20 minutes before being poured into water (50 mL). The resulting mixture was extracted with ethyl acetate (3×30 mL), and the combined extracts were washed sequentially with water (100 mL) and saturated aqueous sodium chloride solution (100 mL), dried over sodium sulfate, filtered, and concentrated in vacuo. Purification via reversed-phase HPLC (Column: Waters XSelect C18, 5 μm; Mobile phase A: 0.1% ammonium hydroxide in water; Mobile phase B: acetonitrile; Gradient: 19% to 49% B), followed by silica gel chromatography (Eluents: 80:1 ethyl acetate/methanol, followed by 10:1 dichloromethane/methanol) afforded the product as a pale yellow solid. From analysis of the $^1$H NMR, this material was presumed to exist as a mixture of rotamers. Yield: 57.6 mg, 0.164 mmol, 64%. LCMS m/z 351.9 [M+H]$^+$. $^1$H NMR (400 MHz, CDCl$_3$) δ 8.01 (br d, J=4.3 Hz, 1H), 7.87 (d, J=2.8 Hz, 1H), 7.11 (dd, J=8.0, 4.8 Hz, 1H), 6.76-6.70 (m, 1H), 4.69-4.65 (br s, 2H), [4.63-4.60 (br s) and 4.60-4.57 (br s), total 2H], [4.19 (dd, J=7.8, 7.5 Hz) and 4.18 (dd, J=7.8, 7.5 Hz), total 2H], 3.69-3.61 (m, 2H), 3.33-3.22 (m, 1H), 3.07-3.02 (m, 3H), [2.83 (d, J=7.3 Hz) and 2.81 (d, J=7.3 Hz), total 2H], 2.41 (s, 3H), [2.09 (s) and 2.08 (s), total 3H].

Example 5

1-(Pyridin-3-yl)azetidin-3-yl 6,7-dimethyl-4-(methylamino)-1,3-dihydro-2H-pyrrolo[3,4-c]pyridine-2-carboxylate (5)

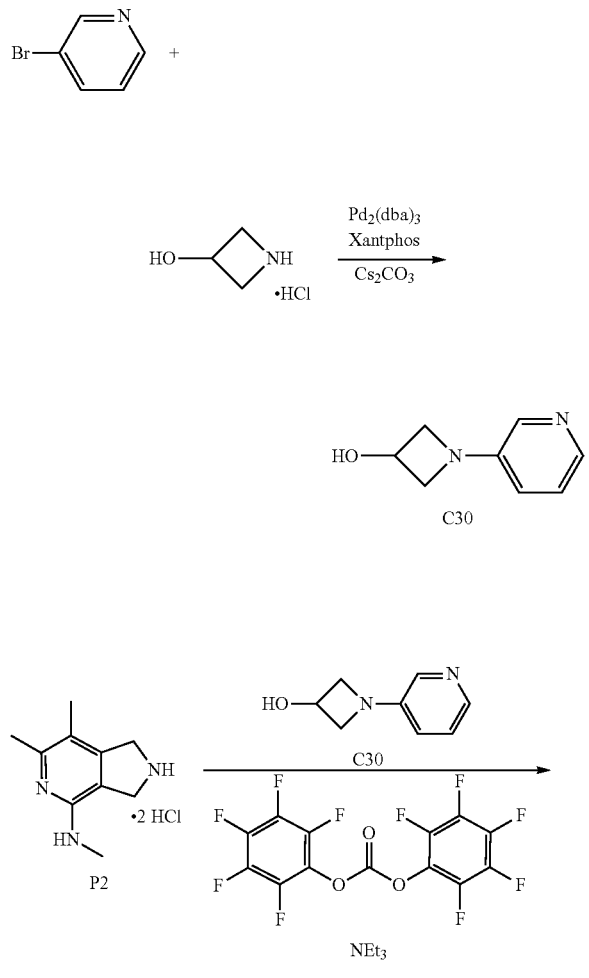

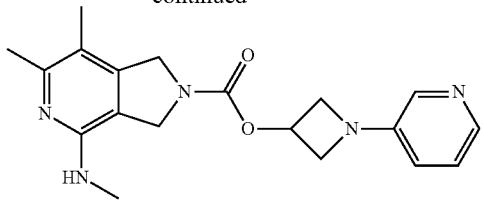

Step 1. Synthesis of 1-(pyridin-3-yl)azetidin-3-ol (C30)

A mixture of azetidin-3-ol, hydrochloride salt (347 mg, 3.17 mmol), 3-bromopyridine (500 mg, 3.16 mmol), tris(dibenzylideneacetone)dipalladium(0) (86.9 mg, 94.9 μmol), 4,5-bis(diphenylphosphino)-9,9-dimethylxanthene (110 mg, 0.190 mmol), and cesium carbonate (3.09 g, 9.48 mmol) in 1,4-dioxane (20 mL) was stirred at 95° C. to 100° C. for 18 hours. After the reaction mixture had cooled to room temperature, water (50 mL) was added, and the resulting mixture was washed with ethyl acetate (3×50 mL). The combined organic layers were washed with saturated aqueous sodium chloride solution (50 mL), dried over sodium sulfate, filtered, and concentrated in vacuo. Silica gel chromatography (Eluent: 30:1 dichloromethane/methanol) provided the product as a yellow solid. Yield: 249 mg, 1.66 mmol, 52%. $^1$H NMR (400 MHz, CDCl$_3$) δ 8.01 (dd, J=4.6, 1.3 Hz, 1H), 7.86 (d, J=2.9 Hz, 1H), 7.11 (dd, J=8.2, 4.6 Hz, 1H), 6.75 (ddd, J=8.3, 2.8, 1.3 Hz, 1H), 4.82 (tt, J=6.4, 4.6 Hz, 1H), 4.26-4.20 (m, 2H), 3.74 (br dd, J=8.7, 4.6 Hz, 2H).

Step 2. Synthesis of 1-(pyridin-3-yl)azetidin-3-yl 6,7-dimethyl-4-(methylamino)-1,3-dihydro-2H-pyrrolo[3,4-c]pyridine-2-carboxylate (5)

Bis(pentafluorophenyl) carbonate (287 mg, 0.728 mmol) was added to a solution of C30 (84 mg, 0.56 mmol) in acetonitrile (4 mL). Triethylamine (0.23 mL, 1.6 mmol) was then added, and the reaction mixture was allowed to stir for 6 hours at room temperature (20° C.), whereupon it was cooled to 0° C. To the cold solution was added P2 (140 mg, 0.560 mmol), followed by drop-wise addition of triethylamine (0.23 mL, 1.65 mmol). After the reaction mixture had been allowed to warm to room temperature and stir for 16 hours, it was concentrated in vacuo. The residue was subjected to reversed-phase HPLC (Column: Waters XBridge C18 OBD, 5 μm; Mobile phase A: water containing 0.05% ammonium hydroxide; Mobile phase B: acetonitrile; Gradient: 22% to 52% B) to provide the product as a white solid. From analysis of the $^1$H NMR, this material was presumed to exist as a mixture of rotamers. Yield: 79.0 mg, 0.224 mmol, 40%. LCMS m/z 353.9 [M+H]$^+$. $^1$H NMR (400 MHz, CDCl$_3$) δ 8.06 (dd, J=4.8, 1.3 Hz, 1H), 7.93-7.90 (m, 1H), 7.14 (dd, J=8.3, 4.5 Hz, 1H), 6.80-6.75 (m, 1H), 5.44 (tt, J=6.3, 4.3 Hz, 1H), 4.64-4.60 (m, 2H), 4.57-4.52 (br s, 2H), 4.37-4.31 (m, 2H), 3.98-3.90 (m, 2H), [3.84-3.76 (br s) and 3.76-3.69 (br s), total 1H], [3.04 (d, J=5.3 Hz) and 3.02 (d, J=5.5 Hz), total 3H], 2.40 (s, 3H), [2.08 (s) and 2.06 (s), total 3H].

Example 6

6,7-Dihydro-5H-cyclopenta[b]pyridin-6-yl 6,7-dimethyl-4-(methylamino)-1,3-dihydro-2H-pyrrolo[3,4-c]pyridine-2-carboxylate (6)

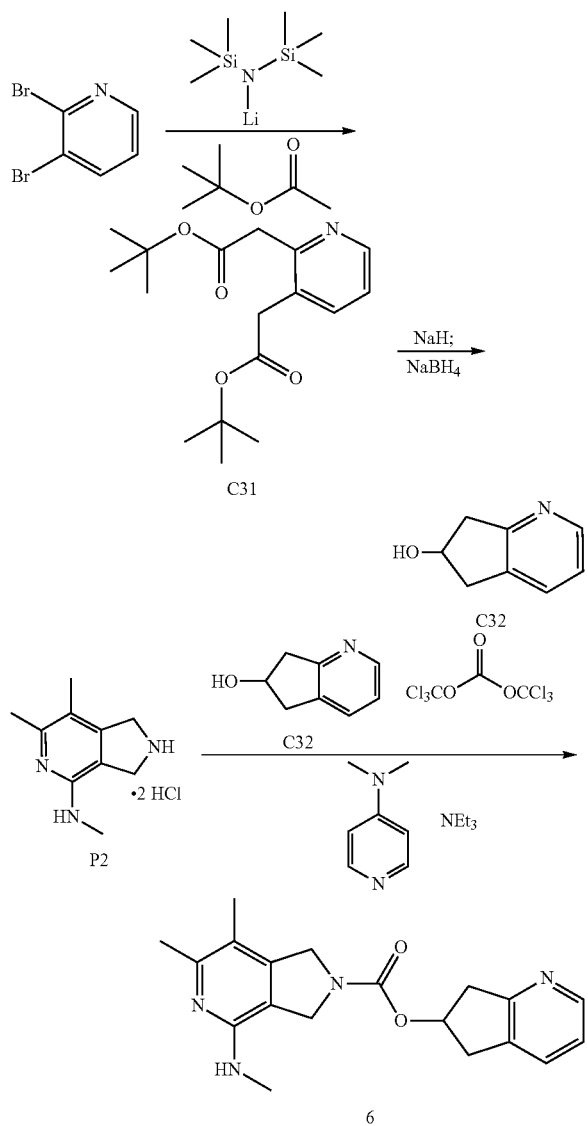

Step 1. Synthesis of di-tert-butyl 2,2'-pyridine-2,3-diyldiacetate (C31)

A flask containing 2,3-dibromopyridine (1.52 g, 6.42 mmol) and chloro(2-dicyclohexylphosphino-2',6'-dimethoxy-1,1'-biphenyl)[2-(2'-amino-1,1'-biphenyl)]palladium (II) (SPhos Pd G2; 231 mg, 0.321 mmol) was evacuated and charged with nitrogen. Toluene (40 mL) was added, followed by a fairly rapid drop-wise addition of lithium bis(trimethylsilyl)amide (1 M solution in toluene; 38.5 mL, 38.5 mmol) and then a fairly rapid drop-wise addition of tert-butyl acetate (2.58 mL, 19.1 mmol). The reaction mixture was allowed to stir at room temperature for 1 hour, whereupon it was quenched with saturated aqueous ammonium chloride solution (75 mL) and then extracted with ethyl acetate (3×75 mL). The combined organic layers were dried over sodium sulfate, filtered, and concentrated in vacuo. Silica gel chromatography (Gradient: 0% to 100% ethyl acetate in heptane) afforded the product as a thick yellow oil. Yield: 986 mg, 3.21 mmol, 50%. $^1$H NMR (400 MHz, CDCl$_3$) δ 8.47 (dd, J=4.7, 1.6 Hz, 1H), 7.57 (dd, J=7.6, 1.4 Hz, 1H), 7.18 (dd, J=7.6, 4.9 Hz, 1H), 3.87 (s, 2H), 3.59 (s, 2H), 1.45 (s, 9H), 1.44 (s, 9H).

Step 2. Synthesis of 6,7-dihydro-5H-cyclopenta[b]pyridin-6-ol (C32)

Sodium hydride (60% dispersion in mineral oil; 163 mg, 4.08 mmol) was washed with heptane (2×2 mL) and suspended in tetrahydrofuran (10 mL). A solution of C31 (727 mg, 2.37 mmol) in tetrahydrofuran (12 mL) was added, and the reaction mixture was stirred at 62° C. for 2.5 hours. After cooling to room temperature, the reaction mixture was concentrated in vacuo, and the resulting paste was overlaid with hydrochloric acid (20%; 6 mL) and stirred at 55° C. for 0.5 hours. This mixture was allowed to cool slightly before being concentrated under reduced pressure to a brown paste, which was slurried in methanol (10 mL) and cooled to 0° C. Sodium borohydride (313 mg, 8.27 mmol) was added in portions, and the reaction mixture was stirred at 0° C. for 15 minutes. It was then allowed to stir at room temperature overnight, whereupon it was diluted w/ aqueous sodium bicarbonate solution (40 mL) and extracted w/ ethyl acetate (5×50 mL). The combined organic layers were dried over sodium sulfate, filtered, and concentrated in vacuo; the residue was subjected to chromatography on silica gel (Gradient: 0% to 10% methanol in dichloromethane), affording the product as a brown oil. Yield: 159 mg, 1.18 mmol, 50%. $^1$H NMR (400 MHz, CDCl$_3$) δ 8.35 (d, J=4.7 Hz, 1H), 7.54 (d, J=7.4 Hz, 1H), 7.08 (dd, J=7.8, 5.1 Hz, 1H), 4.80-4.73 (m, 1H), 3.33 (dd, component of ABX pattern, J=17.2, 5.8 Hz, 1H), 3.25 (dd, component of ABX pattern, J=16.6, 6.0 Hz, 1H), 3.04 (dd, component of ABX pattern, J=17.2, 3.1 Hz, 1H), 2.96 (dd, component of ABX pattern, J=16.6, 2.5 Hz, 1H), 2.47 (br s, 1H).

Step 3. Synthesis of 6,7-dihydro-5H-cyclopenta[b]pyridin-6-yl 6,7-dimethyl-4-(methylamino)-1,3-dihydro-2H-pyrrolo[3,4-c]pyridine-2-carboxylate (6)

A mixture of C32 (47 mg, 0.35 mmol), 4-(dimethylamino)pyridine (85 mg, 0.70 mmol), and bis(trichloromethyl) carbonate (85.1 mg, 0.287 mmol) in dichloromethane (5 mL) was stirred at room temperature for 2.5 hours, whereupon a mixture of P2 (223 mg, 0.891 mmol) and triethylamine (291 μL, 2.09 mmol) in dichloromethane (3 mL) was added rapidly, in a drop-wise manner. After the reaction mixture had been stirred at room temperature for 3 hours, it was diluted with aqueous sodium bicarbonate solution (20 mL), and extracted w/ ethyl acetate (5×20 mL). The combined organic layers were dried over sodium sulfate, filtered, and concentrated in vacuo. Silica gel chromatography (Gradient: 0% to 10% methanol in dichloromethane) afforded the product as a solid. From analysis of the $^1$H NMR, this material was presumed to exist as a mixture of rotamers. Yield: 86.3 mg, 0.255 mmol, 73%. LCMS m/z 339.3 [M+H]$^+$. $^1$H NMR (400 MHz, CDCl$_3$) δ 8.43 (d, J=5.1 Hz, 1H), 7.55 (d, J=7.4 Hz, 1H), 7.15-7.09 (m, 1H), 5.64-5.57 (m, 1H), 4.65-4.56 (m, 2H), 4.49-4.39 (m, 2H), 3.53-3.37 (m, 2H), [3.23 (dd, component of ABX pattern, J=17.6, 2.7 Hz) and 3.21 (dd, component of ABX pattern, J=18.0, 2.7 Hz), total 1H], [3.14 (dd, component of ABX pattern, J=17.6, 2.3 Hz) and 3.12 (dd, component of ABX pattern, J=17.4, 2.1 Hz), total 1H], [3.04 (d, J=5.1 Hz) and 2.99 (d, J=5.1 Hz), total 3H], [2.40 (s) and 2.39 (s), total 3H], [2.07 (s) and 2.01 (s), total 3H].

Examples 7, 8, and 9
1-(4-Amino-6,7-dimethyl-1,3-dihydro-2H-pyrrolo[3,4-c]pyridin-2-yl)-2-[trans-2-(6-fluoropyridin-3-yl)cyclopropyl]ethanone (7), 1-(4-Amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-1 (8), and 1-(4-Amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-2 (9)
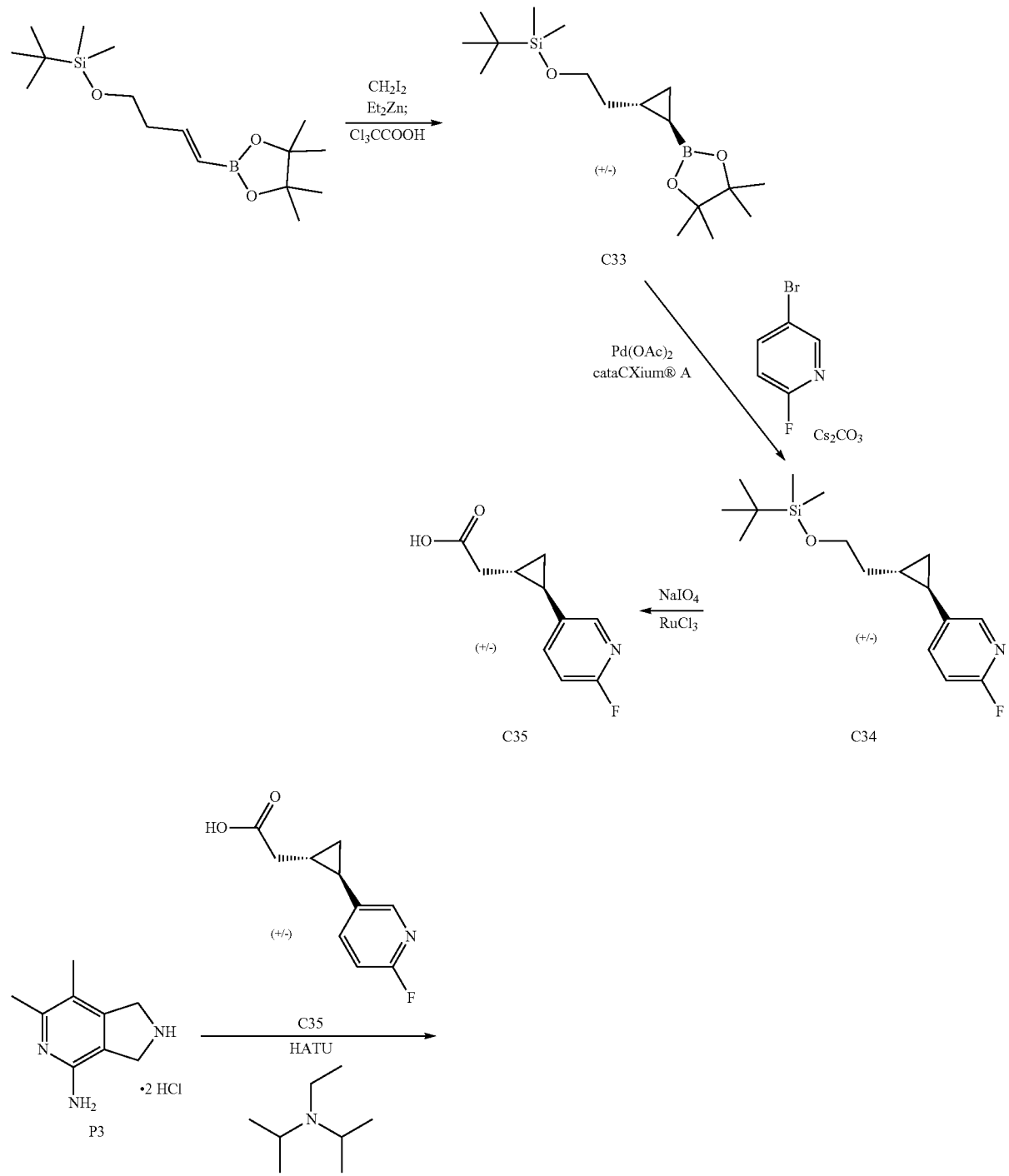

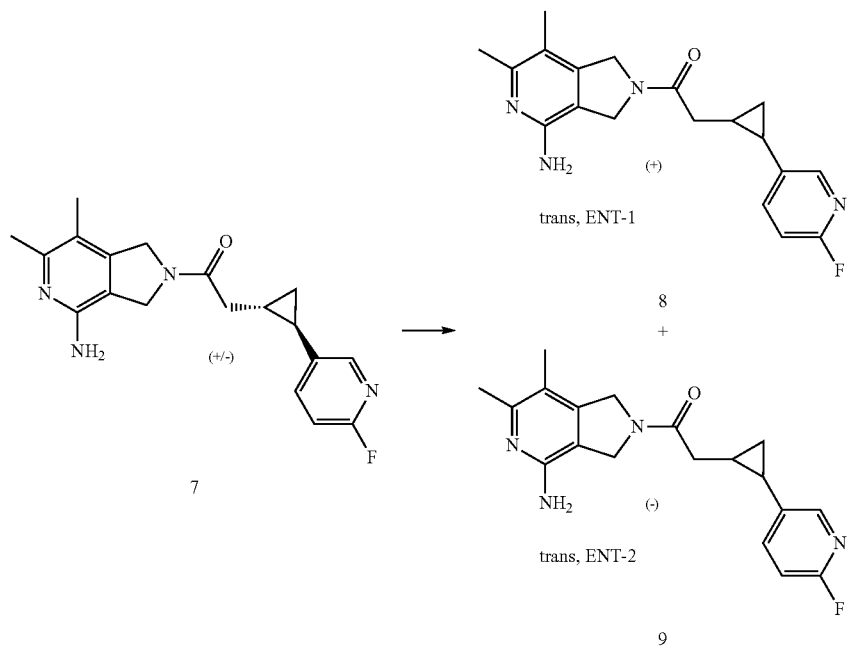 [SMILES: Cc1nc(N)c2c(c1C)CN(C(=O)C[C@@H]1C[C@H]1c1ccc(F)nc1)C2 ; Cc1nc(N)c2c(c1C)CN(C(=O)CC1CC1c1ccc(F)nc1)C2 ; Cc1nc(N)c2c(c1C)CN(C(=O)CC1CC1c1ccc(F)nc1)C2]

Step 1. Synthesis of tert-butyl(dimethyl){2-[trans-2-(4,4,5,5-tetramethyl-1,3,2-dioxaborolan-2-yl)cyclopropyl]ethoxy}silane (C33)

Diiodomethane (2.1 kg, 7.8 mol) was added in a drop-wise manner to a −40° C. solution of diethylzinc (1 M, 3.85 L, 3.85 mol) in dichloromethane (8 L). After this mixture had stirred for 2 hours, a solution of trichloroacetic acid (0.628 kg, 3.84 mol) in dichloromethane (1 L) was added drop-wise, and the reaction mixture was warmed to −10° C. and allowed to stir for an additional 2 hours. A solution of tert-butyl(dimethyl){[(3E)-4-(4,4,5,5-tetramethyl-1,3,2-dioxaborolan-2-yl)but-3-en-1-yl]oxy}silane (400 g, 1.28 mol) in dichloromethane (1 L) was slowly added, and the reaction mixture was stirred at room temperature overnight, whereupon it was quenched via addition of cold aqueous citric acid solution (10%, 10 L). The organic layer was washed with saturated aqueous sodium chloride solution, and concentrated in vacuo; purification of the residue using chromatography on silica gel (Gradient: 0% to 7% ethyl acetate in petroleum ether) provided the product as a light yellow oil. Yield: 260 g, 797 mmol, 62%. $^1$H NMR (400 MHz, CDCl$_3$) δ 3.71-3.64 (m, 2H), 1.51-1.44 (m, 2H), 1.22 (s, 12H), 1.04-0.95 (m, 1H), 0.90 (s, 9H), 0.71-0.65 (m, 1H), 0.46-0.39 (m, 1H), 0.06 (s, 6H), −0.35 to −0.42 (m, 1H).

Step 2. Synthesis of 5-[trans-2-(2-{[tert-butyl(dimethyl)silyl]oxy}ethyl)cyclopropyl]-2-fluoropyridine (C34)

Bis(1-adamantyl)-butylphosphane (cataCXium® A; 652 mg, 1.82 mmol) was added to palladium(II) acetate (408 mg, 1.82 mmol). After addition of degassed 2-methylbutan-2-ol (120 mL), the reaction vessel was evacuated and charged with nitrogen. This evacuation cycle was repeated twice, and the catalyst/ligand mixture was stirred at room temperature for one hour. The mixture was then treated with degassed water (3 mL), followed by cesium carbonate (17.8 g, 54.6 mmol) and 5-bromo-2-fluoropyridine (3.20 g, 18.2 mmol). A solution of C33 (6.53 g, 20.0 mmol) in 2-methylbutan-2-ol (30 mL) was added via syringe, and the reaction vessel was repeatedly evacuated and charged with nitrogen, as described above. The reaction mixture was heated at 75° C. for 16 hours, whereupon it was diluted with water (50 mL), and the resulting mixture was extracted with ethyl acetate (3×150 mL). The combined organic layers were washed with saturated aqueous sodium chloride solution (100 mL), dried over sodium sulfate, filtered, and concentrated in vacuo. Silica gel chromatography (Gradient: 2% to 9% ethyl acetate in petroleum ether) afforded the product as a pale brown oil. Yield: 5.20 g, 17.6 mmol, 97%. $^1$H NMR (400 MHz, CDCl$_3$) δ 7.98 (br s, 1H), 7.38 (ddd, J=8.0, 8.0, 2.5 Hz, 1H), 6.81 (dd, J=8.8, 2.8 Hz, 1H), 3.74 (t, J=6.3 Hz, 2H), 1.70-1.59 (m, 3H), 1.17-1.06 (m, 1H), 0.92-0.83 (m, 2H), 0.89 (s, 9H), 0.05 (s, 3H), 0.04 (s, 3H).

Step 3. Synthesis of [trans-2-(6-fluoropyridin-3-yl)cyclopropyl]acetic Acid (C35)

Ruthenium(III) chloride (365 mg, 1.76 mmol) was added to a solution of C34 (5.20 g, 17.6 mmol) in acetonitrile (150 mL) at room temperature. A solution of sodium periodate (11.3 g, 52.8 mmol) in water (20 mL) was then added with stirring, and the reaction mixture was allowed to stir overnight at room temperature (18° C.). After addition of hydrochloric acid (1 M; 20 mL) and removal of solvents in vacuo, the residue was taken up in acetonitrile (50 mL) and filtered through diatomaceous earth. The filter pad was washed with acetonitrile (30 mL), and the combined filtrates were concentrated under reduced pressure, providing the product as a pale brown solid. Yield: 3.20 g, 16.4 mmol, 93%. LCMS m/z 195.8 [M+H]$^+$.

Step 4. Synthesis of 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone (7)

This reaction was run in two identical batches. N,N-Diisopropylethylamine (3.28 g, 25.4 mmol) was added to a mixture of P3 (2.00 g, 8.47 mmol), C35 (1.98 g, 10.1 mmol), and O-(7-azabenzotriazol-1-yl)-N,N,N',N'-tetramethyluronium hexafluorophosphate (3.86 g, 10.2 mmol) in N,N-dimethylformamide (50 mL), and the reaction mixture was stirred at room temperature (10° C.) for 1.5 hours. The two reaction mixtures were then combined and poured into water; the resulting mixture was extracted with dichloromethane (3×100 mL), and the combined organic layers were washed with saturated aqueous sodium chloride solution (100 mL), dried over sodium sulfate, filtered, and concentrated in vacuo. Purification via chromatography on silica gel (Gradient: 1% to 9% methanol in dichloromethane) provided the product as a white solid. From analysis of the $^1$H NMR, this material was presumed to exist as a mixture of rotamers. Yield: 1.88 g, 5.52 mmol, 33%. LCMS m/z 341.1 [M+H]$^+$. $^1$H NMR (400 MHz, CD$_3$OD) δ 8.08-8.04 (m, 1H), 7.72-7.65 (m, 1H), 6.97 (dd, J=8.5, 2.5 Hz, 1H), [4.81 (s), 4.69 (s), 4.66 (s), and 4.56 (s), total 4H], 2.73-2.64 (m, 1H), 2.61-2.53 (m, 1H), 2.33 (s, 3H), 2.10 (s, 3H), 1.93-1.86 (m, 1H), 1.51-1.41 (m, 1H), 1.11-0.98 (m, 2H).

Step 5. Isolation of 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-1 (8) and 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-2 (9)

Separation of 7 (1.61 g, 4.73 mmol) into its component enantiomers was carried out via supercritical fluid chromatography [Column: Chiral Technologies Chiralcel OJ-H, 5 µm; Mobile phase: 82.5:17.5 carbon dioxide/(2-propanol containing 0.2% 1-aminopropan-2-ol)]. The first-eluting enantiomer was obtained as an off-white solid that exhibited a positive (+) rotation, and was designated as 8. From analysis of the $^1$H NMR, this material was presumed to exist as a mixture of rotamers. Yield: 734 mg, 2.16 mmol, 46%. LCMS m/z 341.4 [M+H]$^+$. $^1$H NMR (400 MHz, DMSO-d$_6$) δ 8.07 (br s, 1H), 7.72-7.65 (m, 1H), 7.06 (dd, J=8.4, 2.9 Hz, 1H), [5.68 (br s) and 5.64 (br s), total 2H], [4.68 (s), 4.56 (s), 4.50 (s), and 4.40 (s), total 4H], 2.61-2.42 (m, 2H, assumed; partially obscured by solvent peak), 2.22 (s, 3H), [1.99 (s) and 1.99 (s), total 3H], 1.88-1.81 (m, 1H), 1.44-1.33 (m, 1H), 1.05-0.97 (m, 1H), 0.97-0.89 (m, 1H).

The second-eluting enantiomer was obtained as an off-white solid that exhibited a negative (−) rotation, and was designated as 9. From analysis of the $^1$H NMR, this material was presumed to exist as a mixture of rotamers. Yield: 733 mg, 2.15 mmol, 46%. LCMS m/z 341.4 [M+H]$^+$. $^1$H NMR (400 MHz, DMSO-d$_6$) δ 8.07 (br s, 1H), 7.72-7.65 (m, 1H), 7.06 (dd, J=8.6, 2.7 Hz, 1H), [5.70 (br s) and 5.65 (br s), total 2H], [4.69 (s), 4.56 (s), 4.50 (s), and 4.40 (s), total 4H], 2.61-2.42 (m, 2H, assumed; partially obscured by solvent peak), 2.23 (s, 3H), [1.99 (s) and 1.99 (s), total 3H], 1.88-1.81 (m, 1H), 1.44-1.33 (m, 1H), 1.05-0.97 (m, 1H), 0.96-0.89 (m, 1H).

Examples 10 and 11

1-[6,7-Dimethyl-4-(methylamino)-1,3-dihydro-2H-pyrrolo[3,4-c]pyridin-2-yl]-2-[trans-2-(pyridin-3-yl)cyclopropyl]ethanone, ENT-1 (10) and 1-[6,7-Dimethyl-4-(methylamino)-1,3-dihydro-2H-pyrrolo[3,4-c]pyridin-2-yl]-2-[trans-2-(pyridin-3-yl)cyclopropyl]ethanone, ENT-2 (11)

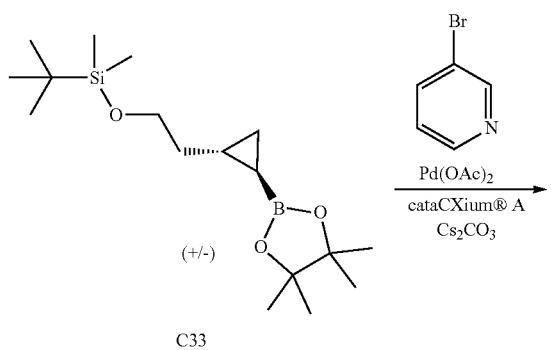

C33

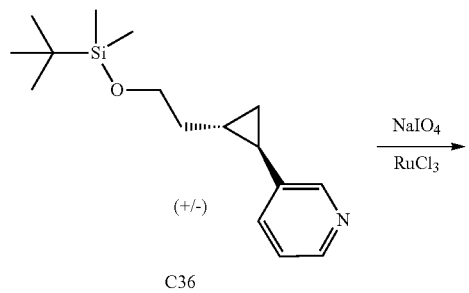

C36

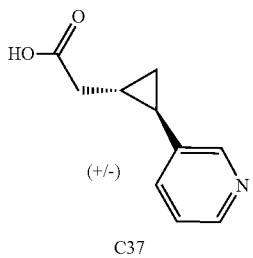

C37

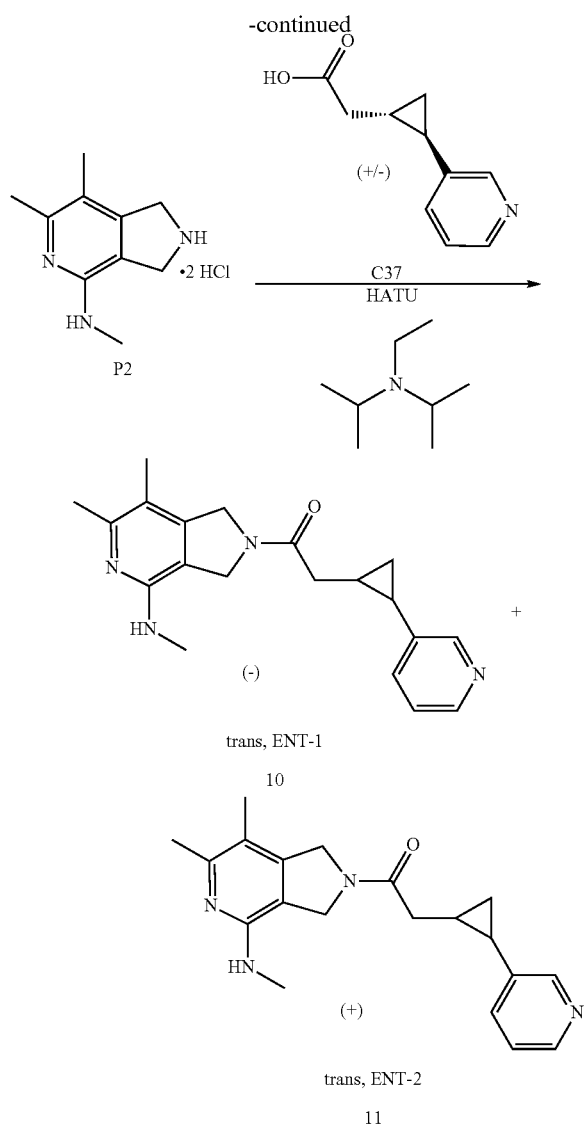

Step 1. Synthesis of 3-[trans-2-(2-{[tert-butyl(dimethyl)silyl]oxy}ethyl)cyclopropyl]pyridine (C36)

Bis(1-adamantyl)-butylphosphane (68.1 mg, 0.190 mmol) was added to palladium(II) acetate (42.6 mg, 0.190 mmol). After addition of degassed 2-methylbutan-2-ol (16 mL), the reaction vessel was evacuated and charged with nitrogen. This evacuation cycle was repeated twice, and the catalyst/ligand mixture was stirred at room temperature for one hour. The mixture was then treated with degassed water (1 mL), followed by cesium carbonate (1.86 g, 5.71 mmol) and 3-bromopyridine (300 mg, 1.90 mmol). A solution of C33 (744 mg, 2.28 mmol) in 2-methylbutan-2-ol (4 mL) was added via syringe, and the reaction vessel was repeatedly evacuated and charged with nitrogen, as described above. The reaction mixture was heated at 75° C. for 16 hours, whereupon it was diluted with water (30 mL), and the resulting mixture was extracted with ethyl acetate (3×30 mL). The combined organic layers were washed with saturated aqueous sodium chloride solution (30 mL), dried over sodium sulfate, filtered, and concentrated in vacuo. The residue was purified via silica gel chromatography (Eluent: 5:1 petroleum ether/ethyl acetate) to afford the product as a yellow oil. Yield: 380 mg, 1.37 mmol, 72%. $^1$H NMR (400 MHz, CDCl$_3$) δ 8.40 (d, J=2.0 Hz, 1H), 8.38 (dd, J=4.8, 1.5 Hz, 1H), 7.26 (ddd, J=7.8, 2.0, 2.0 Hz, 1H, assumed; partially obscured by solvent peak), 7.16 (dd, J=7.8, 4.8 Hz, 1H), 3.73 (t, J=6.4 Hz, 2H), 1.69-1.60 (m, 3H), 1.20-1.10 (m, 1H), 0.95-0.85 (m, 2H), 0.88 (s, 9H), 0.04 (s, 3H), 0.03 (s, 3H).

Step 2. Synthesis of [trans-2-(pyridin-3-yl)cyclopropyl]acetic Acid (C37)

Ruthenium(III) chloride (28.4 mg, 0.137 mmol) was added to a solution of C36 (380 mg, 1.37 mmol) in acetonitrile (20 mL) at room temperature. A solution of sodium periodate (879 mg, 4.11 mmol) in water (5 mL) was then added with stirring, and the reaction mixture was allowed to stir at room temperature (22° C.) for 2 hours. After addition of hydrochloric acid (1 M; 5 mL) and removal of solvents in vacuo, the residue was taken up in acetonitrile (50 mL) and filtered through diatomaceous earth. The filter pad was washed with acetonitrile (30 mL), and the combined filtrates were concentrated under reduced pressure, providing the product as a pale brown oil. Yield: 200 mg, 1.13 mmol, 82%.

Step 3. Synthesis of 1-[6,7-dimethyl-4-(methylamino)-1,3-dihydro-2H-pyrrolo[3,4-c]pyridin-2-yl]-2-[trans-2-(pyridin-3-yl)cyclopropyl]ethanone, ENT-1 (10) and 1-[6,7-dimethyl-4-(methylamino)-1,3-dihydro-2H-pyrrolo[3,4-c]pyridin-2-yl]-2-[trans-2-(pyridin-3-yl)cyclopropyl]ethanone, ENT-2 (11)

N,N-Diisopropylethylamine (372 mg, 2.88 mmol) was slowly added to a solution of P2 (240 mg, 0.959 mmol), C37 (195 mg, 1.10 mmol), and O-(7-azabenzotriazol-1-yl)-N,N,N',N'-tetramethyluronium hexafluorophosphate (474 mg, 1.25 mmol) in N,N-dimethylformamide (5.0 mL) at room temperature (10° C.). After the reaction mixture had been stirred at room temperature (10° C.) for 50 minutes, it was subjected to reversed-phase HPLC (Column: Waters XBridge C18 OBD, 5 μm; Mobile phase A: water containing 0.05% ammonium hydroxide; Mobile phase B: acetonitrile; Gradient: 18% to 48% B), and the purified mixture of enantiomers 10 and 11 was combined with the product of a similar reaction carried out using P2 (70 mg, 0.28 mmol) for separation of the component enantiomers via supercritical fluid chromatography [Column: Chiral Technologies Chiralpak AS, 5 μm; Mobile phase: 85:15 carbon dioxide/(methanol containing 0.1% ammonium hydroxide)]. The first-eluting enantiomer was obtained as a white solid that exhibited a negative (−) rotation, and was designated as 10. From analysis of the $^1$H NMR, this material was presumed to exist as a mixture of rotamers. Combined yield: 41.4 mg, 0.123 mmol, 10%. LCMS m/z 337.2 [M+H]$^+$. $^1$H NMR (400 MHz, CDCl$_3$) δ 8.47 (br s, 1H), 8.41 (dd, J=4.5, 1.5 Hz, 1H), 7.43-7.38 (m, 1H), 7.19 (dd, J=7.8, 4.8 Hz, 1H), [4.70 (s), 4.67-4.64 (m), and 4.63-4.58 (m), total 4H], [3.05 (s) and 3.04 (s), total 3H], [2.60 (dd, component of ABX pattern, J=16.3, 6.8 Hz) and 2.58 (dd, component of ABX pattern, J=16.1, 6.5 Hz), total 1H], [2.52 (dd, component of ABX pattern, J=15.8, 2.8 Hz) and 2.50 (dd, component of ABX pattern, J=15.8, 2.8 Hz), total 1H], 2.41 (s, 3H), [2.09 (s) and 2.07 (s), total 3H], 1.86-1.79 (m, 1H), 1.58-1.48 (m, 1H), 1.14-1.07 (m, 1H), 1.03-0.96 (m, 1H).

The second-eluting enantiomer was obtained as a white solid that exhibited a positive (+) rotation, and was designated as 11. From analysis of the ¹H NMR, this material was presumed to exist as a mixture of rotamers. Combined yield: 66.5 mg, 0.198 mmol, 16%. LCMS m/z 337.2 [M+H]⁺. ¹H NMR (400 MHz, CDCl₃) δ 8.47 (br s, 1H), 8.40 (dd, J=5.0, 1.5 Hz, 1H), 7.43-7.38 (m, 1H), 7.18 (dd, J=7.8, 4.8 Hz, 1H), [4.69 (s), 4.67-4.64 (m), and 4.63-4.58 (m), total 4H], [3.99-3.87 (br m) and 3.84-3.73 (br m), total 1H], [3.04 (s) and 3.03 (s), total 3H], [2.60 (dd, component of ABX pattern, J=15.8, 6.8 Hz) and 2.57 (dd, component of ABX pattern, J=16.1, 6.5 Hz), total 1H], [2.51 (dd, component of ABX pattern, J=16.1, 3.5 Hz) and 2.50 (dd, component of ABX pattern, J=16.1, 3.5 Hz), total 1H], 2.41 (s, 3H), [2.08 (s) and 2.07 (s), total 3H], 1.85-1.78 (m, 1H, assumed; partially obscured by water peak), 1.58-1.48 (m, 1H), 1.14-1.06 (m, 1H), 1.03-0.96 (m, 1H).

Example 12

2-[1-(Pyridin-3-yl)azetidin-3-yl]-1-(4,6,7-trimethyl-1,3-dihydro-2H-pyrrolo[3,4-c]pyridin-2-yl)ethanone (12)

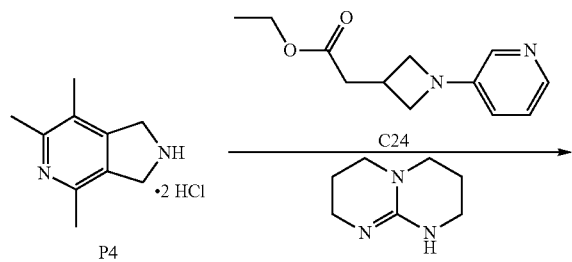

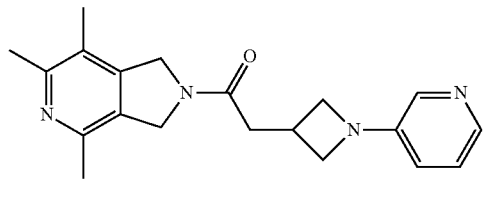

A mixture of C24 (51.0 mg, 0.232 mmol), P4 (23.0 mg, 97.8 μmol), and N,N-dimethylformamide (1.0 mL) was treated with 1,3,4,6,7,8-hexahydro-2H-pyrimido[1,2-a]pyrimidine (56.4 mg, 0.405 mmol), and the reaction mixture was heated at 70° C. for 6 hours. After it had cooled to room temperature, the reaction mixture was diluted with aqueous lithium chloride solution (10%; 1 mL). The aqueous layer was extracted five times with ethyl acetate, and the combined organic layers were concentrated in vacuo. Silica gel chromatography (Gradient: 0% to 20% methanol in dichloromethane) afforded the product as a solid. From analysis of the ¹H NMR, this material was presumed to exist as a mixture of rotamers. Yield: 22 mg, 65 μmol, 66%. LCMS m/z 337.2 [M+H]⁺. ¹H NMR (400 MHz, CDCl₃) δ 8.01 (br d, J=4.5 Hz, 1H), 7.87 (d, J=2.5 Hz, 1H), 7.13 (dd, J=8.3, 4.8 Hz, 1H), 6.77-6.72 (m, 1H), 4.79-4.73 (m, 4H), 4.20 (dd, J=7.6, 7.6 Hz, 2H), 3.70-3.64 (m, 2H), 3.35-3.23 (m, 1H), [2.85 (d, J=7.6 Hz) and 2.84 (d, J=7.6 Hz), total 2H], 2.52 (s, 3H), [2.45 (s) and 2.44 (s), total 3H], [2.20 (s) and 2.19 (s), total 3H].

TABLE 1

Method of preparation, structure, and physicochemical data for Examples 13-59.

| Example Number | Method of Preparation; Non-commercial starting materials | Structure | ¹H NMR (400 MHz, CDCl₃) δ; Mass spectrum, observed ion m/z [M + H]⁺ or HPLC retention time; Mass spectrum m/z [M + H]⁺ (unless otherwise indicated) |
|---|---|---|---|
| 13 | Example 4; P5, C25 | 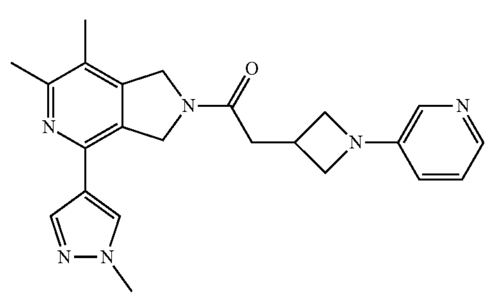 [SMILES: Cc1nc(-c2cnn(C)c2)c2c(c1C)CN(C(=O)CC1CN(c3cccnc3)C1)C2] | From analysis of the ¹H NMR, this material was presumed to exist as a mixture of rotamers; 8.00 (d, J = 4.5 Hz, 1H), [7.96 (s) and 7.91 (s), total 1H], 7.87 (d, J = 2.3 Hz, 1H), [7.86 (s) and 7.78 (s), total 1H], 7.11 (dd, J = 8.2, 4.6 Hz, 1H), 6.73 (br d, J = 8.3 Hz, 1H), [4.93 (s) and 4.91 (s), total 2H], 4.79-4.73 (m, 2H), 4.20 (dd, J = 7.5, 7.5 Hz, 2H), [3.98 (s) and 3.97 (s), total 3H], 3.71-3.63 (m, 2H), 3.36-3.23 (m, 1H), [2.89 (d, J = 7.8 Hz) and 2.86 (d, J = 7.8 Hz), total 2H], 2.54 (s, 3H), [2.22 (s) and 2.21 (s), total 3H]; 403.1 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 14 | Example 4; P6, C25 | 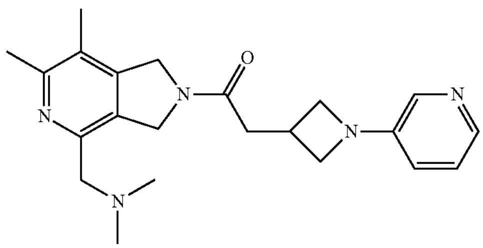 [SMILES: Cc1nc(CN(C)C)c2c(c1C)CN(C(=O)CC1CN(c3cccnc3)C1)C2] | mixture of rotamers; $^1$H NMR (400 MHz, CD$_3$OD), characteristic peaks: δ 7.86 (br d, J = 4.8 Hz, 1H), 7.75 (d, J = 2.8 Hz, 1H), 7.21 (dd, J = 8.3, 4.8 Hz, 1H), 6.93-6.88 (m, 1H), [4.99 (s) and 4.90 (s), total 2H], 4.73 (s, 1H), 4.16 (dd, J = 7.8, 7.5 Hz, 2H), 3.71-3.65 (m, 2H), 3.53 (s, 2H), 3.28-3.17 (m, 1H), 2.93 (d, J = 7.8 Hz, 2H), 2.51 (s, 3H), 2.26 (br s, 9H); 380.3 |
| 15 | Example 4$^1$; P2, C35 | trans, ENT-1 | mixture of rotamers; $^1$H NMR (400 MHz, DMSO-d$_6$) δ 8.09-8.05 (m, 1H), 7.72-7.64 (m, 1H), 7.06 (dd, J = 8.4, 2.9 Hz, 1H), [5.98 (br q, J = 4.8 Hz) and 5.92 (br q, J = 4.5 Hz), total 1H], [4.68 (s), 4.55 (s), 4.49 (s), and 4.39 (s), total 4H], 2.81-2.76 (m, 3H), 2.61-2.42 (m, 2H, assumed; partially obscured by solvent peak), 2.27 (s, 3H), [2.00 (s) and 1.99 (s), total 3H], 1.88-1.80 (m, 1H), 1.42-1.33 (m, 1H), 1.05-0.97 (m, 1H), 0.96-0.89 (m, 1H); 354.9 |
| 16 | Example 4$^1$; P2, C35 | trans, ENT-2 | mixture of rotamers; $^1$H NMR (400 MHz, DMSO-d$_6$) δ 8.10-8.05 (m, 1H), 7.72-7.64 (m, 1H), 7.06 (dd, J = 8.5, 2.5 Hz, 1H), [5.98 (br q, J = 4.5 Hz) and 5.92 (br q, J = 4 Hz), total 1H], [4.68 (s), 4.55 (s), 4.49 (s), and 4.39 (s), total 4H], 2.83-2.76 (m, 3H), 2.6-2.4 (m, 2H, assumed; obscured by solvent peak), 2.27 (s, 3H), 2.00 (br s, 3H), 1.88-1.81 (m, 1H), 1.42-1.34 (m, 1H), 1.05-0.97 (m, 1H), 0.96-0.89 (m, 1H); 354.9 |
| 17 | Example 4$^2$; C3, C25 | 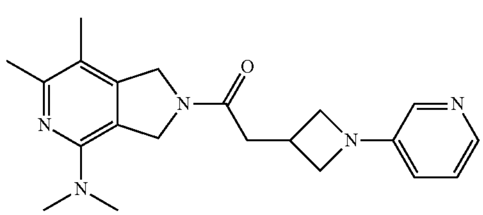 [SMILES: Cc1nc(N(C)C)c2c(c1C)CN(C(=O)CC1CN(c3cccnc3)C1)C2] | mixture of rotamers; 8.00 (d, J = 4.5 Hz, 1H), 7.87 (d, J = 2.5 Hz, 1H), 7.10 (dd, J = 8.0, 4.8 Hz, 1H), 6.72 (br d, J = 8 Hz, 1H), 4.92-4.87 (m, 2H), 4.63 (s, 2H), 4.18 (dd, J = 7.5, 7.5 Hz, 2H), 3.68-3.62 (m, 2H), 3.34-3.22 (m, 1H), 3.04 (s, 3H), 3.01 (s, 3H), [2.82 (d, J = 7.5 Hz) and 2.82 (d, J = 7.5 Hz), total 2H], [2.39 (s) and 2.38 (s), total 3H], [2.09 (s) and 2.08 (s), total 3H]; 366.0 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 18 | Example 4; P7, C25 | 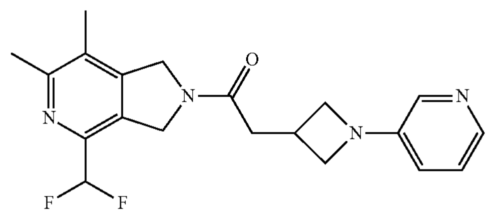 [SMILES: Cc1nc(C(F)F)c2c(c1C)CN(C(=O)CC1CN(c3cccnc3)C1)C2] | mixture of rotamers; $^1$H NMR (400 MHz, CD$_3$OD) δ 7.86 (br d, J = 4.8 Hz, 1H), 7.76-7.73 (m, 1H), 7.21 (dd, J = 8.5, 4.8 Hz, 1H), 6.94-6.88 (m, 1H), [6.69 (t, J$_{HF}$ = 55.0 Hz) and 6.69 (t, J$_{HF}$ = 55.0 Hz), total 1H], [5.08 (s), 4.95-4.9 (m, assumed; partially obscured by water peak), and 4.76 (s), total 4H], [4.16 (dd, J = 7.5, 7.5 Hz) and 4.15 (dd, J = 7.5, 7.5 Hz), total 2H], 3.72-3.65 (m, 2H), 3.27-3.17 (m, 1H), [2.95 (d, J = 7.5 Hz) and 2.93 (d, J = 7.5 Hz), total 2H], 2.54 (s, 3H), 2.31 (s, 3H); 373.1 |
| 19 | Example 1$^3$; P2, C23 | 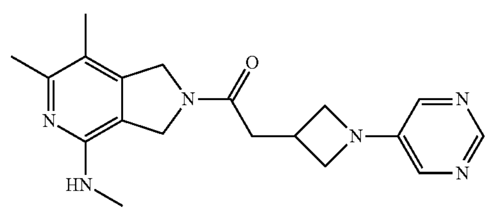 [SMILES: CNc1nc(C)c(C)c2c1CN(C(=O)CC1CN(c3cncnc3)C1)C2] | mixture of rotamers; 8.64 (s, 1H), 7.96 (s, 2H), 4.67 (br s, 2H), 4.67-4.56 (m, 2H), [4.25 (dd, J = 7.8, 7.8 Hz) and 4.25 (dd, J = 7.5, 7.5 Hz), total 2H], 3.75-3.68 (m, 2H), 3.39-3.29 (m, 1H), 3.08-3.02 (m, 3H), 2.86-2.80 (m, 2H), 2.42 (s, 3H), [2.09 (s) and 2.08 (s), total 3H]; 353.1 |
| 20 | Example 4$^{2,3}$; C3 | 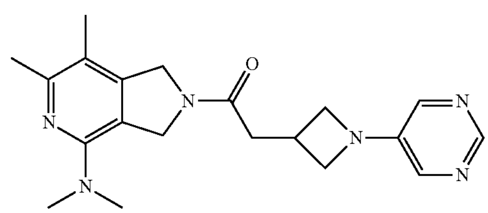 [SMILES: Cc1nc(N(C)C)c2c(c1C)CN(C(=O)CC1CN(c3cncnc3)C1)C2] | mixture of rotamers; 8.64 (s, 1H), 7.96 (s, 2H), 4.94-4.88 (m, 2H), 4.64 (br s, 2H), 4.25 (dd, J = 8, 8 Hz, 2H), 3.75-3.70 (m, 2H), 3.40-3.28 (m, 1H), 3.05 (s, 3H), 3.02 (s, 3H), 2.84 (d, J = 8 Hz, 2H), 2.40 (s, 3H), [2.10 (s) and 2.09 (s), total 3H]; 366.9 |
| 21 | Example 4$^4$; C1, C25 | 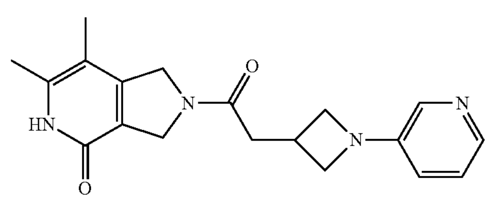 [SMILES: Cc1[nH]c(=O)c2c(c1C)CN(C(=O)CC1CN(c3cccnc3)C1)C2] | 11.4-11.2 (v br s, 1H), 8.01 (d, J = 4.5 Hz, 1H), 7.87 (d, J = 2.5 Hz, 1H), 7.11 (dd, J = 8.5, 4.5 Hz, 1H), 6.73 (br d, J = 8 Hz, 1H), 4.75-4.66 (m, 4H), 4.22-4.15 (m, 2H), 3.68-3.61 (m, 2H), 3.32-3.20 (m, 1H), 2.80 (d, J = 7.5 Hz, 2H), 2.32 (s, 3H), 2.01 (br s, 3H); 338.9 |
| 22 | Example 2$^{5,6}$; C3, C23 | 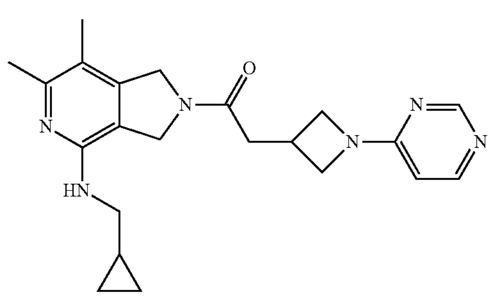 [SMILES: Cc1nc(NCC2CC2)c2c(c1C)CN(C(=O)CC1CN(c3ccncn3)C1)C2] | mixture of rotamers; $^1$H NMR (400 MHz, CD$_3$OD) δ 8.38 (s, 1H), 8.08 (d, J = 6.0 Hz, 1H), 6.38 (d, J = 6.3 Hz, 1H), [4.76 (s), 4.66 (s), 4.60 (s), and 4.51 (s), total 4H], 4.33 (dd, J = 8.8, 8.5 Hz, 2H), 3.91-3.83 (m, 2H), 3.28-3.19 (m, 1H), 3.26 (dd, J = 6.8, 2.0 Hz, 2H), 2.92 (d, J = 7.5 Hz, 2H), 2.33 (s, 3H), [2.08 (s) and 2.08 (s), total 3H], 1.16-1.05 (m, 1H), 0.52-0.44 (m, 2H), 0.27-0.20 (m, 2H); 393.0 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 23 | Example 4[7]; P2 | 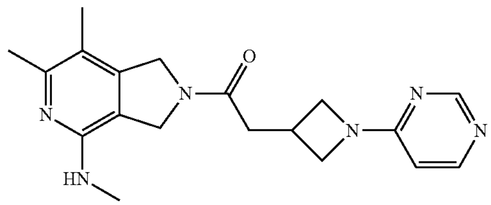 [SMILES: CNc1nc(C)c(C)c2c1CN(C(=O)CC1CN(c3ccncn3)C1)C2] | mixture of rotamers; $^1$H NMR (400 MHz, CD$_3$OD) δ 8.38 (s, 1H), 8.07 (d, J = 6.3 Hz, 1H), 6.38 (d, J = 6.3 Hz, 1H), [4.76 (s), 4.61 (s), 4.60 (s), and 4.48 (s), total 4H], 4.32 (dd, J = 8.8, 8.8 Hz, 2H), 3.91-3.83 (m, 2H), 3.29-3.17 (m, 1H), [2.95 (s) and 2.95 (s), total 3H], 2.93-2.87 (m, 2H), 2.37 (s, 3H), [2.08 (s) and 2.07 (s), total 3H]; 353.4 |
| 24 | Example 4; P2 | 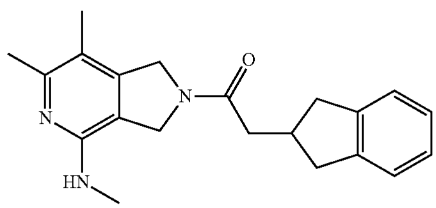 [SMILES: CNc1nc(C)c(C)c2c1CN(C(=O)CC1Cc3ccccc3C1)C2] | mixture of rotamers; $^1$H NMR (500 MHz, DMSO-d$_6$) δ 7.22-7.18 (m, 2H), 7.13-7.08 (m, 2H), [4.88 (s), 4.71 (s), 4.69 (s), and 4.55 (s), total 4H], 3.13-3.02 (m, 5H), 2.88-2.79 (m, 1H), 2.66-2.56 (m, 3H), 2.55-2.5 (m, 4H, assumed; partially obscured by solvent peak), [2.06 (s) and 2.03 (s), total 3H]; 336.0 |
| 25 | Example 2[8,9]; P1, C23 | 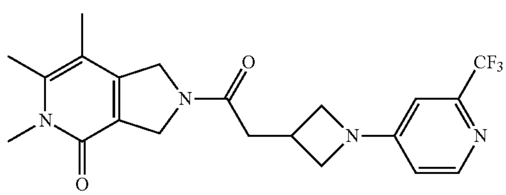 [SMILES: Cc1c2c(c(=O)n(C)c1C)CN(C(=O)CC1CN(c3ccnc(C(F)(F)F)c3)C1)C2] | 8.28 (d, J = 6.0 Hz, 1H), 6.60-6.56 (m, 1H), 6.32 (br d, J = 5.5 Hz, 1H), 4.73-4.66 (m, 4H), 4.32-4.19 (m, 2H), 3.78-3.71 (m, 2H), 3.60 (s, 3H), 3.36-3.23 (m, 1H), 2.79 (d, J = 8.0 Hz, 2H), 2.35 (s, 3H), 2.06 (s, 3H); 421.1 |
| 26 | C26, C37[10,11] | trans, ENT-1 | 4.06 minutes[12]; 338.0 |
| 27 | C26, C37[10,11] | trans, ENT-2 | 5.45 minutes[12]; 338.3 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 28 | Examples 7, 8, and 9; P2, C33 | (+/−) | mixture of rotamers; $^1$H NMR (500 MHz, CDCl$_3$) δ 9.04 (s, 1H), 8.57 (s, 2H), [4.69 (s), 4.64 (s), 4.62 (s), and 4.61 (s), total 4H], 3.04 (s, 3H), 2.67-2.58 (m, 1H), 2.55-2.44 (m, 1H), 2.40 (s, 3H), [2.09 (s) and 2.07 (s), total 3H], 1.83-1.76 (m, 1H), 1.64-1.54 (m, 1H), 1.19-1.12 (m, 1H), 1.10-1.02 (m, 1H); 338.1 |
| 29 | Example 28[13] | trans, ENT-1 | 3.59 minutes[14]; 338.3 |
| 30 | Example 28[13] | trans, ENT-2 | 4.18 minutes[14]; 338.3 |
| 31 | Example 4; P2 | 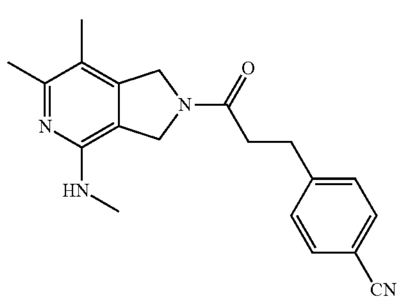 [SMILES: CNc1nc(C)c(C)c2c1CN(C(=O)CCc1ccc(C#N)cc1)C2] | mixture of rotamers; $^1$H NMR (400 MHz, DMSO-d$_6$) δ 7.76 (br d, J = 8 Hz, 2H), [7.50 (d, J = 8.0 Hz) and 7.49 (d, J = 8.0 Hz), total 2H], [4.68 (s), 4.53 (s), 4.49 (s), and 4.39 (s), total 4H], 2.96 (t, J = 7.5 Hz, 2H), [2.79 (s) and 2.78 (s), total 3H], 2.76-2.65 (m, 2H), 2.26 (s, 3H), [2.00 (s) and 1.98 (s), total 3H]; 335.1 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 32 | Example 4; P2 | 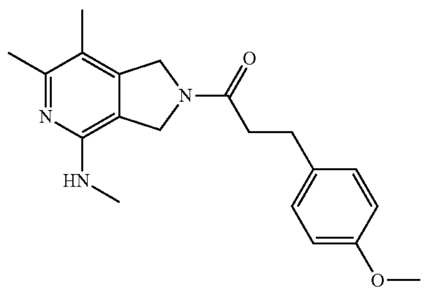 | mixture of rotamers; $^1$H NMR (400 MHz, CD$_3$OD), characteristic peaks: δ 7.17 (br d, J = 8 Hz, 2H), [6.82 (d, J = 8.5 Hz) and 6.81 (d, J = 8.5 Hz), total 2H], [4.54 (s), 4.49 (s), and 4.46 (s), total 3H], [3.73 (s) and 3.72 (s), total 3H], 2.96-2.90 (m, 2H), [2.92 (s) and 2.91 (s), total 3H], [2.71 (t, J = 7.3 Hz) and 2.70 (t, J = 7.5 Hz), total 2H], [2.34 (s) and 2.33 (s), total 3H], [2.07 (s) and 2.01 (s), total 3H]; 340.2 |
| 33 | Examples 7, 8, and 9; P2, C33 | (+/-) | mixture of rotamers; 8.23 (br s, 1H), 7.45-7.39 (m, 1H), 7.21 (d, J = 8.0 Hz, 1H), [4.69 (s), 4.64 (s), 4.60 (s), and 4.58 (s), total 4H], [3.88-3.79 (m) and 3.76-3.66 (m), total 1H], [3.04 (s) and 3.03 (s), total 3H], 2.61-2.45 (m, 2H), 2.40 (s, 3H), [2.09 (s) and 2.07 (s), total 3H], 1.83-1.76 (m, 1H), 1.55-1.44 (m, 1H), 1.11-1.04 (m, 1H), 1.04-0.96 (m, 1H); 371.2 (chlorine isotope pattern observed) |
| 34 | Example 2$^8$; P2, C23 | 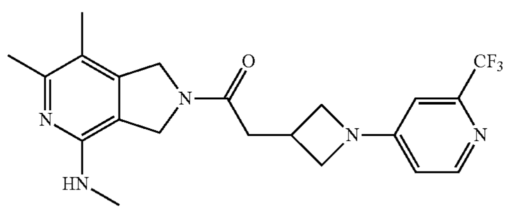 [SMILES: CNc1nc(C)c(C)c2c1CN(C(=O)CC1CN(c3ccnc(C(F)(F)F)c3)C1)C2] | mixture of rotamers; 8.28 (d, J = 5.5 Hz, 1H), 6.58 (d, J = 2.0 Hz, 1H), 6.33 (dd, J = 5.8, 2.3 Hz, 1H), [4.66 (s), 4.60 (s), and 4.58 (s), total 4H], 4.31-4.24 (m, 2H), 3.77-3.70 (m, 2H), 3.38-3.27 (m, 1H), [3.05 (s) and 3.04 (s), total 3H], 2.84-2.78 (m, 2H), 2.41 (s, 3H), [2.09 (s) and 2.08 (s), total 3H]; 420.1 |
| 35 | Example 4$^{15}$; P2, C23 | 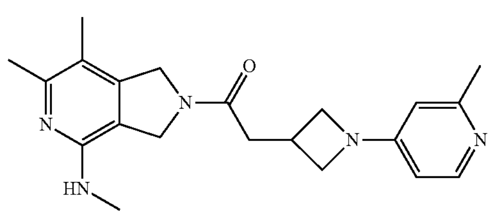 | mixture of rotamers; $^1$H NMR (400 MHz, DMSO-d$_6$) δ 7.96 (d, J = 5.5 Hz, 1H), 6.18 (d, half of AB quartet, J = 2.0 Hz, 1H), 6.15 (dd, component of ABX pattern, J = 5.5, 2.0 Hz, 1H), [5.97 (br q, J = 4.5 Hz) and 5.91 (br q, J = 4.5 Hz), total 1H], [4.69 (s), 4.55 (s), 4.47 (s), and 4.38 (s), total 4H], 4.04 (dd, J = 8.0, 7.5 Hz, 2H), 3.60-3.52 (m, 2H), 3.13-3.01 (m, 1H), 2.83-2.75 (m, 5H), [2.28 (s) and 2.27 (s), total 6H], [2.00 (s) and 1.99 (s), total 3H]; 366.0 |
| 36 | Example 2$^{16}$; P2, C23 | 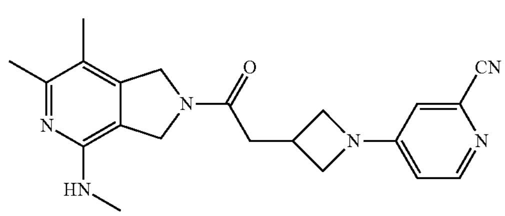 [SMILES: CNc1nc(C)c(C)c2c1CN(C(=O)CC1CN(c3ccnc(C#N)c3)C1)C2] | mixture of rotamers; $^1$H NMR (400 MHz, DMSO-d$_6$) δ 8.16 (d, J = 6.0 Hz, 1H), 6.96 (br d, J = 2.0 Hz, 1H), 6.54 (dd, J = 5.8, 2.3 Hz, 1H), [5.98 (br q, J = 5.0 Hz) and 5.92 (br q, J = 4.5 Hz), total 1H], [4.70 (s), 4.56 (s), 4.48 (s), and 4.38 (s), total 4H], 4.14 (dd, J = 8.5, 8.5 Hz, 2H), 3.71-3.64 (m, 2H), 3.16-3.05 (m, 1H), 2.86-2.76 (m, 5H), 2.27 (s, 3H), [2.00 (s), and 1.99 (s), total 3H]; 376.9 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 37 | Example 2[17]; P2, C23 | 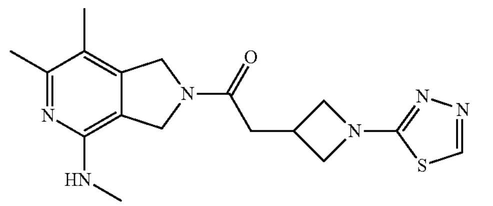 [SMILES: CNc1nc(C)c(C)c2c1CN(C(=O)CC1CN(c3nncs3)C1)C2] | mixture of rotamers; $^1$H NMR (400 MHz, CD$_3$OD) δ 8.64 (s, 1H), [4.77 (s), 4.63 (s), 4.61 (s), and 4.48 (s), total 4H], 4.35 (dd, J = 8.0, 8.0 Hz, 2H), 3.96-3.89 (m, 2H), 3.38-3.28 (m, 1H, assumed; partially obscured by solvent peak), 2.96-2.91 (m, 5H), 2.36 (s, 3H), [2.09 (s) and 2.08 (s), total 3H]; 359.0 |
| 38 | P2[18] | 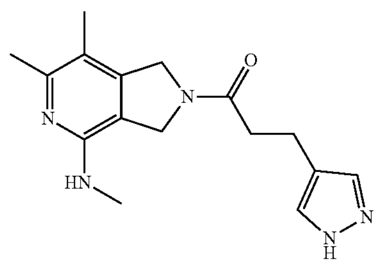 [SMILES: CNc1nc(C)c(C)c2c1CN(C(=O)CCc1cn[nH]c1)C2] | 2.11 minutes[19]; 300 |
| 39 | Example 4[20]; P7, C23 | 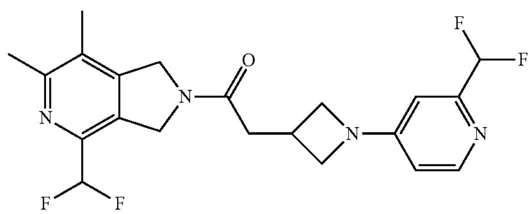 [SMILES: Cc1nc(C(F)F)c2c(c1C)CN(C(=O)CC1CN(c3ccnc(C(F)F)c3)C1)C2] | mixture of rotamers; 8.23 (d, J = 5.5 Hz, 1H), [6.62 (t, J$_{HF}$ = 55.0 Hz) and 6.61 (t, J$_{HF}$ = 55.0 Hz), total 1H], 6.56 (d, J = 2.0 Hz, 1H), 6.51 (t, J$_{HF}$ = 55.7 Hz, 1H), 6.30 (dd, J = 6.0, 2.0 Hz, 1H), 5.00 (s, 2H), 4.76 (s, 2H), [4.27 (dd, J = 8.5, 8.0 Hz) and 4.27 (dd, J = 8.0, 8.0 Hz), total 2H], 3.78-3.70 (m, 2H), 3.37-3.26 (m, 1H), 2.88-2.81 (m, 2H), 2.56 (s, 3H), 2.28 (br s, 3H); 423.1 |
| 40 | Examples 7, 8, and 9[21,22]; P2, C33 | trans, ENT-1 | 3.76 minutes[23]; 354.3 |
| 41 | Examples 7, 8, and 9[21,22]; P2, C33 | trans, ENT-2 | 4.89 minutes[23]; 354.3 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 42 | Example 4[24]; P8, C23 | (+/−) | mixture of rotamers; 8.27 (d, J = 5.5 Hz, 1H), 6.57 (s, 1H), 6.32 (d, J = 5.5 Hz, 1H), [5.30 (br q, J = 6.2 Hz) and 5.07 (br q, J = 6.2 Hz), total 1H], [4.72 (d, J = 15.2 Hz), 4.54 (AB quartet, J$_{AB}$ = 12.7 Hz, Δν$_{AB}$ = 17.1 Hz), and 4.37 (d, J = 14.8 Hz), total 2H], 4.30-4.21 (m, 2H), 3.81-3.68 (m, 2H), 3.37-3.25 (m, 1H), [3.04 (s) and 3.03 (s), total 3H], 2.93-2.71 (m, 2H), 2.40 (s, 3H), 2.11 (s, 3H), 1.48-1.42 (m, 3H); 434.3 |
| 43 | Example 42[25] | ENT-1 | 1.61 minutes[26]; 434.0 |
| 44 | Example 42[25] | ENT-2 | 1.83 minutes[26]; 434.1 |
| 45 | Examples 7, 8, and 9; P2, C33 | (+/−) | 1.07 minutes[27]; 351.4 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 46 | Example 45[28] | trans, ENT-1 | mixture of rotamers; $^1$H NMR (400 MHz, CD$_3$OD) δ 8.28-8.24 (m, 1H), 7.46-7.41 (m, 1H), 7.18 (d, J = 8.4 Hz, 1H), [4.76 (s), 4.62 (s), and 4.49 (s), total 4H], [2.94 (s) and 2.94 (s), total 3H], 2.69-2.54 (m, 2H), 2.47 (s, 3H), 2.36 (s, 3H), [2.08 (s) and 2.08 (s), total 3H], 1.89-1.82 (m, 1H), 1.50-1.40 (m, 1H), 1.09-0.96 (m, 2H); 351.2 |
| 47 | Example 45[28] | trans, ENT-2 | mixture of rotamers; $^1$H NMR (400 MHz, CD$_3$OD) δ 8.29-8.23 (m, 1H), 7.47-7.40 (m, 1H), 7.18 (d, J7.9 Hz, 1H), [4.76 (s), 4.63 (s), and 4.50 (s), total 4H], [2.94 (s) and 2.94 (s), total 3H], 2.70-2.54 (m, 2H), 2.47 (s, 3H), 2.36 (s, 3H), 2.08 (s, 3H), 1.89-1.82 (m, 1H), 1.50-1.40 (m, 1H), 1.09-0.96 (m, 2H); 351.2 |
| 48 | P2[21] | 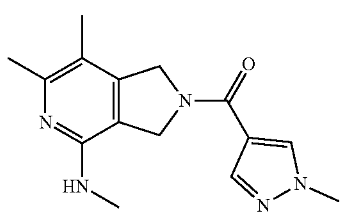 | mixture of rotamers; [7.93 (s) and 7.93 (s), total 1H], [7.90 (s) and 7.87 (s), total 1H], [4.90 (s), 4.84 (s), and 4.76 (s), total 4H], [3.98 (s) and 3.97 (s), total 3H], [3.96-3.89 (br m) and 3.86-3.78 (br m), total 1H], 3.07-3.03 (m, 3H), 2.42 (m, 3H), [2.12 (s) and 2.10 (s), total 3H]; 285.9 |
| 49 | Example 4[29,30]; P8, C29 | ENT-1 | 1.53 minutes[31]; 432.3 |
| 50 | Example 4[29,30]; P8, C29 | ENT-2 | 3.46 minutes[31]; 432.2 |

TABLE 1-continued

Method of preparation, structure, and physicochemical data for Examples 13-59.

| Example Number | Method of Preparation; Non-commercial starting materials | Structure | $^{1}$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 51 | Example 4[32]; P2, C23 | 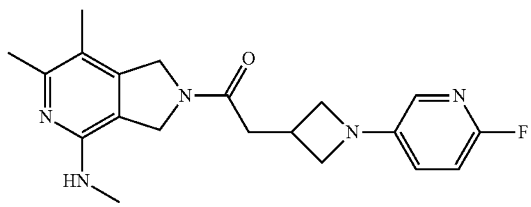 [SMILES: CNc1nc(C)c(C)c2c1CN(C(=O)CC1CN(c3ccc(F)nc3)C1)C2] | mixture of rotamers; 7.36 (br s, 1H), 6.86 (ddd, component of ABXY pattern, J = 8.5, 6.5, 3.0 Hz, 1H), 6.78 (dd, component of ABX pattern, J = 8.8, 2.8 Hz, 1H), [4.67 (s), 4.61 (s), and 4.58 (s), total 4H], [4.15 (dd, J = 7.5, 7.5 Hz) and 4.15 (dd, J = 7.5, 7.5 Hz), total 2H], 3.65-3.58 (m, 2H), 3.32-3.21 (m, 1H), 3.07-3.01 (m, 3H), 2.85-2.78 (m, 2H), 2.41 (s, 3H), [2.09 (s) and 2.08 (s), total 3H]; 370.2 |
| 52 | Example 4; P9, C25 | 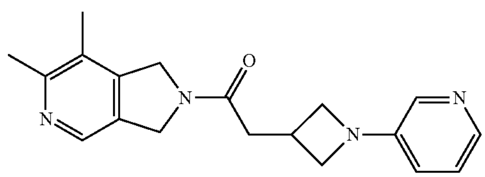 [SMILES: Cc1ncc2c(c1C)CN(C(=O)CC1CN(c3cccnc3)C1)C2] | mixture of rotamers; $^{1}$H NMR (400 MHz, CD$_3$OD) δ [8.23 (s) and 8.21 (s), total 1H], 7.86 (d, J = 5.0 Hz, 1H), 7.78-7.72 (m, 1H), 7.21 (dd, J = 8.0, 4.5 Hz, 1H), 6.90 (br d, J = 8 Hz, 1H), [4.94 (s), 4.92 (s), 4.79 (s), and 4.75 (s), total 4H], 4.15 (dd, J = 7.5, 7.5 Hz, 2H), 3.71-3.64 (m, 2H), 3.27-3.16 (m, 1H), [2.94 (d, J = 7.5 Hz) and 2.91 (d, J = 8.0 Hz), total 2H], 2.51 (s, 3H), 2.27 (s, 3H); 322.9 |
| 53 | Example 4; P10, C25 | 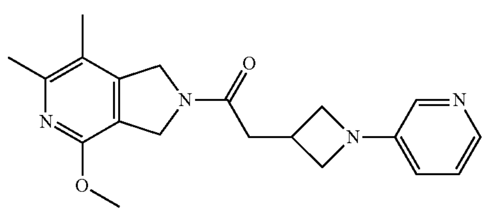 [SMILES: COc1nc(C)c(C)c2c1CN(C(=O)CC1CN(c3cccnc3)C1)C2] | mixture of rotamers; 8.01 (dd, J = 4.5, 1.0 Hz, 1H), 7.87 (d, J = 3.0 Hz, 1H), 7.11 (d, J = 8.3, 4.8 Hz, 1H), 6.73 (br d, J = 8.3 Hz, 1H), 4.70 (br s, 4H), [4.19 (dd, J = 8.0, 7.5 Hz) and 4.18 (dd, J = 7.5, 7.5 Hz), total 2H], [3.95 (s) and 3.95 (s), total 3H], 3.68-3.62 (m, 2H), 3.33-3.20 (m, 1H), [2.82 (d, J = 7.5 Hz) and 2.81 (d, J = 8.0 Hz), total 2H], 2.43 (s, 3H), [2.13 (s) and 2.12 (s), total 3H]; 352.8 |
| 54 | Example 4; P11, C25 | 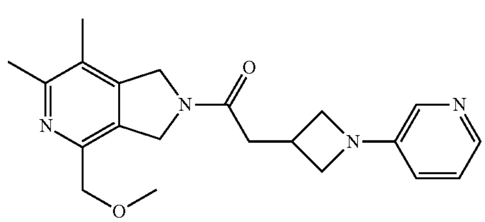 [SMILES: COCc1nc(C)c(C)c2c1CN(C(=O)CC1CN(c3cccnc3)C1)C2] | mixture of rotamers; $^{1}$H NMR (400 MHz, CD$_3$OD), characteristic peaks: δ 7.85 (d, J = 5 Hz, 1H), 7.75 (d, J = 2.5 Hz, 1H), 7.21 (dd, J = 8.5, 5.0 Hz, 1H), 6.90 (br d, J = 8.5 Hz, 1H), [4.97 (s), 4.89 (s), and 4.72 (s), total 3H], [4.54 (s) and 4.54 (s), total 2H], 4.15 (dd, J = 8.0, 7.5 Hz, 2H), 3.68 (dd, J = 7.0, 6.0 Hz, 2H), [3.40 (s) and 3.40 (s), total 3H], 3.27-3.17 (m, 1H), [2.93 (d, J = 7.5 Hz) and 2.92 (d, J = 8.0 Hz), total 2H], 2.50 (s, 3H), 2.26 (s, 3H); 366.9 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 55 | Example 4[3]; P10, C23 | 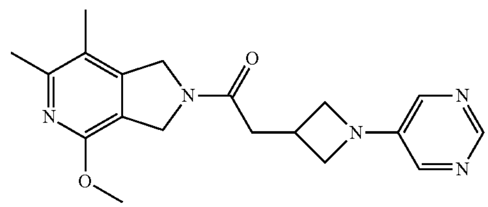 [SMILES: COc1nc(C)c(C)c2c1CN(C(=O)CC1CN(c3cncnc3)C1)C2] | mixture of rotamers; $^1$H NMR (400 MHz, CD$_3$OD), characteristic peaks: δ 8.46 (s, 1H), 8.00 (br s, 2H), [4.76 (s), 4.67 (s), and 4.60 (s), total 3H], [4.23 (dd, J = 8.0, 7.5 Hz) and 4.23 (dd, J = 8.0, 7.5 Hz), total 2H], 3.92 (s, 3H), 3.76 (dd, J = 7.0, 6.0 Hz, 2H), 3.3-3.22 (m, 1H, assumed; partially obscured by solvent peak), 2.96-2.88 (m, 2H), 2.41 (s, 3H), 2.16 (s, 3H); 354.3 |
| 56 | Example 4[3]; P12, C23 | 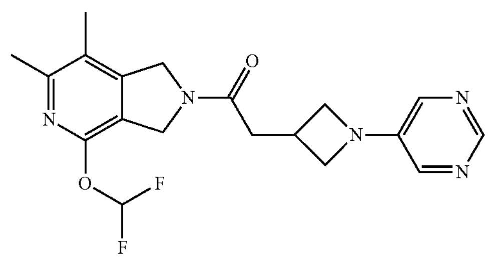 [SMILES: Cc1nc(OC(F)F)c2c(c1C)CN(C(=O)CC1CN(c3cncnc3)C1)C2] | mixture of rotamers; $^1$H NMR (400 MHz, DMSO-d$_6$) δ [8.51 (s) and 8.51 (s), total 1H], [8.02 (s) and 8.02 (s), total 2H], [7.72 (t, $J_{HF}$ = 72.8 Hz) and 7.70 (t, $J_{HF}$ = 73.0 Hz), total 1H], [4.88 (s), 4.82 (s), 4.65 (s), and 4.56 (s), total 4H], 4.16-4.08 (m, 2H), 3.67-3.61 (m, 2H), 3.18-3.06 (m, 1H), 2.89-2.83 (m, 2H), 2.39 (s, 3H), [2.15 (s) and 2.14 (s), total 3H]; 389.9 |
| 57 | Example 4[33,34]; P2 | ENT-1 | mixture of rotamers; $^1$H NMR (400 MHz, CD$_3$OD) δ 7.15 (dd, J = 8.5, 5.5 Hz, 1H), 6.92 (dd, J = 8.5, 1.5 Hz, 1H), 6.82 (ddd, J = 9, 9, 2 Hz, 1H), [4.75 (s), 4.64 (s), 4.61 (s), and 4.51 (s), total 4H], 3.21-3.09 (m, 2H), 3.04-2.93 (m, 1H), [2.94 (s) and 2.92 (s), total 3H], 2.74-2.61 (m, 4H), [2.36 (s) and 2.35 (s), total 3H], [2.09 (s) and 2.06 (s), total 3H]; 354.1 |
| 58 | P2[21] | 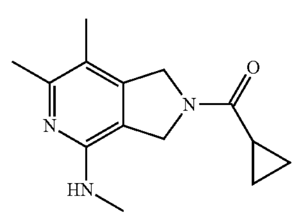 [SMILES: CNc1nc(C)c(C)c2c1CN(C(=O)C1CC1)C2] | mixture of rotamers; [4.88-4.84 (m), 4.80 (br s), 4.69-4.65 (m), and 4.59 (br s), total 4H], [4.0-3.9 (br s) and 3.85-3.75 (br s), total 1H], 3.07-3.01 (m, 3H), 2.41 (s, 3H), [2.09 (s) and 2.08 (s), total 3H], 1.78-1.67 (m, 1H, assumed; partially obscured by water peak), 1.11-1.05 (m, 2H), 0.89-0.81 (m, 2H); 246.3 |

TABLE 1-continued

Method of preparation, structure, and physicochemical data for Examples 13-59.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 59 | P2[35] | 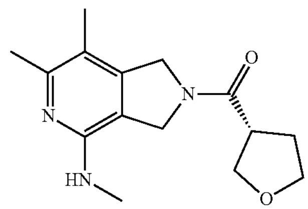 [SMILES: CNc1nc(C)c(C)c2c1CN(C(=O)[C@@H]1CCOC1)C2] | mixture of rotamers; $^1$H NMR (400 MHz, CD$_3$OD) δ [4.9-4.79 (m, assumed; largely obscured by water peak), and 4.75-4.64 (m), total 2H], [4.62 (s) and 4.50 (s), total 2H], 4.06 (dd, J = 8.5, 8.0 Hz, 1H), 3.96-3.88 (m, 2H), 3.88-3.80 (m, 1H), 3.50-3.37 (m, 1H), [2.95 (s) and 2.93 (s), total 3H], 2.36 (s, 3H), 2.31-2.10 (m, 2H), [2.10 (s) and 2.08 (s), total 3H]; 275.9 |

[1] The racemic mixture of Examples 15 and 16 was separated into its component enantiomers via supercritical fluid chromatography [Column: Regis Technologies, (S,S)-Whelk-0 ® 1, 10 μm; Mobile phase: 55:45 carbon dioxide/(methanol containing 0.1% ammonium hydroxide)]. Example 15 was the first-eluting enantiomer, and Example 16 was the second-eluting enantiomer.

[2] Reaction of C3 with dimethylamine hydrochloride and triethylamine afforded tert-butyl 4-(dimethylamino)-6,7-dimethyl-1,3-dihydro-2H-pyrrolo[3,4-c]pyridine-2-carboxylate. Protecting group removal via treatment with hydrogen chloride provided the requisite N,N,6,7-tetramethyl-2,3-dihydro-1H-pyrrolo[3,4-c]pyridin-4-amine, dihydrochloride salt.

[3] The requisite [1-(pyrimidin-5-yl)azetidin-3-yl]acetic acid was synthesized using the method described in Example 1 for synthesis of C25 from C23, but in this case, 5-bromopyrimidine was employed in place of 3-bromopyridine.

[4] 6,7-Dimethyl-1,2,3,5-tetrahydro-4H-pyrrolo[3,4-c]pyridin-4-one, hydrochloride salt was synthesized via deprotection of C1 with hydrogen chloride in ethyl acetate.

[5] Reaction of C3 with 1-cyclopropylmethanamine in 1,4-dioxane provided tert-butyl 4-[(cyclopropylmethyl)amino]-6,7-dimethyl-1,3-dihydro-2H-pyrrolo[3,4-c]pyridine-2-carboxylate, which was deprotected with hydrogen chloride in ethyl acetate to afford N-(cyclopropylmethyl)-6,7-dimethyl-2,3-dihydro-1H-pyrrolo[3,4-c]pyridin-4-amine, hydrochloride salt.

[6] Subjection of 4-chloropyrimidine and C23 to cesium fluoride and triethylamine in dimethyl sulfoxide at 100° C. afforded the requisite ethyl [1-(pyrimidin-4-yl)azetidin-3-yl]acetate.

[7] Hydrolysis of ethyl [1-(pyrimidin-4-yl)azetidin-3-yl]acetate (see footnote 6) with lithium hydroxide provided [1-(pyrimidin-4-yl)azetidin-3-yl]acetic acid.

[8] Subjection of 4-chloro-2-(trifluoromethyl)pyridine and C23 to cesium fluoride and triethylamine in dimethyl sulfoxide at 100° C. afforded the requisite ethyl {1-[2-(trifluoromethyl)pyridin-4-yl]azetidin-3-yl}acetate.

[9] 5,6,7-Trimethyl-1,2,3,5-tetrahydro-4H-pyrrolo[3,4-c]pyridin-4-one, hydrochloride salt was synthesized via deprotection of P1 with hydrogen chloride.

[10] Treatment of C37 with sulfuric acid in methanol provided the requisite methyl [trans-2-(pyridin-3-yl)cyclopropyl]acetate.

[11] Reaction of C26 with methyl [trans-2-(pyridin-3-yl)cyclopropyl]acetate, mediated by trimethylaluminum in 1,2-dichloroethane at 80° C., afforded a racemic mixture of Examples 26 and 27. This was separated into its component enantiomers via supercritical fluid chromatography [Column: Chiral Technologies Chiralcel OJ-H, 5 μm; Mobile phase: 9:1 carbon dioxide/(methanol containing 0.2% ammonium hydroxide)]. Example 26 was the first-eluting enantiomer, and Example 27 was the second-eluting enantiomer.

[12] Conditions for analytical HPLC. Column: Chiral Technologies Chiralcel OJ-H, 4.6 × 100 mm, 5 μm; Mobile phase: 9:1 carbon dioxide/(methanol containing 0.2% ammonium hydroxide); Back pressure: 200 bar; Flow rate: 1.5 mL/minute.

[13] The racemate Example 28 was separated into its component enantiomers via supercritical fluid chromatography [Column: Chiral Technologies Chiralpak IA, 5 μm; Mobile phase: 3:1 carbon dioxide/(methanol containing 0.2% ammonium hydroxide)]. Example 29 was the first-eluting enantiomer, and Example 30 was the second-eluting enantiomer.

[14] Conditions for analytical HPLC. Column: Chiral Technologies Chiralpak IA, 4.6 × 100 mm, 5 μm; Mobile phase: 65:35 carbon dioxide/(methanol containing 0.2% ammonium hydroxide); Back pressure: 200 bar; Flow rate: 1.5 mL/minute.

[15] Reaction of C23 with 4-chloro-2-methylpyridine and N,N-diisopropylethylamine afforded ethyl [1-(2-methylpyridin-4-yl)azetidin-3-yl]acetate, which was hydrolyzed with lithium hydroxide to provide the requisite [1-(2-methylpyridin-4-yl)azetidin-3-yl]acetic acid.

[16] Reaction of C23 with 4-chloropyridine-2-carbonitrile and N,N-diisopropylethylamine afforded the requisite ethyl [1-(2-cyanopyridin-4-yl)azetidin-3-yl]acetate.

[17] Reaction of C23 with 2-bromo-1,3,4-thiadiazole in the presence of tris(dibenzylideneacetone)dipalladium(0) and 1,1'-binaphthalen-2-yl(di-tert-butyl)phosphane provided the requisite ethyl [1-(1,3,4-thiadiazol-2-yl)azetidin-3-yl]acetate.

[18] The synthesis of Example 38 was carried out in library format. Reaction of P2 with 3-(1H-pyrazol-4-yl)propanoic acid was mediated via 1-[3-(dimethylamino)propyl]-3-ethylcarbodiimide hydrochloride, 1H-benzotriazol-1-ol, and triethylamine.

[19] Conditions for analytical HPLC. Column: Waters XBridge C18, 2.1 × 50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute.

[20] Subjection of 4-chloro-2-(difluoromethyl)pyridine and C23 to cesium fluoride and triethylamine in dimethyl sulfoxide at 100° C. afforded ethyl {1-[2-(difluoromethyl)pyridin-4-yl]azetidin-3-yl}acetate. This material was hydrolyzed with lithium hydroxide to provide the requisite {1-[2-(difluoromethyl)pyridin-4-yl]azetidin-3-yl}acetic acid.

[21] In this case, the final amide coupling was carried out using 1,1'-carbonyldiimidazole rather than O-(7-azabenzotriazol-1-yl)-N,N,N',N'-tetramethyluronium hexafluorophosphate and N,N-diisopropylethylamine.

[22] The racemic mixture of Examples 40 and 41 was separated into its component enantiomers via supercritical fluid chromatography [Column: Chiral Technologies Chiralcel OJ-H, 5 μm; Mobile phase: 4:1 carbon dioxide/(methanol containing 0.2% ammonium hydroxide)]. Example 40 was the first-eluting enantiomer, and Example 41 was the second-eluting enantiomer.

[23] Conditions for analytical HPLC. Column: Chiral Technologies Chiralcel OJ-H, 4.6 × 100 mm, 5 μm; Mobile phase: 4:1 carbon dioxide/(methanol containing 0.2% ammonium hydroxide); Back pressure: 150 bar; Flow rate: 1.5 mL/minute.

[24] Ethyl {1-[2-(trifluoromethyl)pyridin-4-yl]azetidin-3-yl}acetate (see footnote 8) was hydrolyzed with lithium hydroxide to provide the requisite {1-[2-(trifluoromethyl)pyridin-4-yl]azetidin-3-yl}acetic acid.

[25] Racemate Example 42 was separated into its component enantiomers via supercritical fluid chromatography [Column: Chiral Technologies Chiralcel OJ-H, 5 μm; Mobile phase: 3:1 carbon dioxide/(acetonitrile containing 0.2% ammonium hydroxide)]. Example 43 was the first-eluting enantiomer, and Example 44 was the second-eluting enantiomer.

[26] Conditions for analytical HPLC. Column: Chiral Technologies Chiralcel OJ-H, 4.6 × 100 mm, 5 μm; Mobile phase: 65:35 carbon dioxide/(acetonitrile containing 0.2% ammonium hydroxide); Back pressure: 120 bar; Flow rate: 1.5 mL/minute.

[27] Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

[28] Racemic Example 45 was separated into its component enantiomers via supercritical fluid chromatography [Column: Chiral Technologies Chiralpak AD, 10 μm; Mobile phase: 1:1 carbon dioxide/(ethanol containing 0.1% ammonium hydroxide)]. Example 46 was the first-eluting enantiomer, and Example 47 was the second-eluting enantiomer.

[29] Hydrolysis of C29 with lithium hydroxide provided the requisite {1-[2-(difluoromethoxy)pyridin-4-yl]azetidin-3-yl}acetic acid.

[30] The racemic mixture of Examples 49 and 50 was separated into its component enantiomers via supercritical fluid chromatography [Column: Phenomenex Lux Cellulose-3, 5 μm; Mobile phase: 7:3 carbon dioxide/(methanol containing 0.2% ammonium hydroxide)]. Example 49 was the first-eluting enantiomer, and Example 50 was the second-eluting enantiomer.

[31] Conditions for analytical HPLC. Column: Phenomenex Lux Cellulose-3, 4.6 × 100 mm, 5 μm; Mobile phase: 3:2 carbon dioxide/(methanol containing 0.2% ammonium hydroxide); Back pressure: 120 bar; Flow rate: 1.5 mL/minute.

[32] Using the method described for synthesis of C29 from C28 in Example 3, C23 was reacted with 5-bromo-2-fluoropyridine. Hydrolysis of the product using lithium hydroxide afforded the requisite [1-(6-fluoropyridin-3-yl)azetidin-3-yl]acetic acid.

[33] Sulfuric acid-mediated reaction of 5-fluoro-2,3-dihydro-1H-inden-1-one with oxoacetic acid provided (5-fluoro-1-oxo-1,3-dihydro-2H-inden-2-ylidene)acetic acid, which was reduced using hydrogen and rhodium(I) tris(triphenylphosphine) chloride. The resulting (5-fluoro-1-oxo-2,3-dihydro-1H-inden-2-yl)acetic acid was subjected to triethylsilane and titanium(IV) chloride to afford the requisite (5-fluoro-2,3-dihydro-1H-inden-2-yl)acetic acid.

[34] The racemic mixture of Example 57 and its enantiomer was separated via supercritical fluid chromatography [Column: Chiral Technologies Chiralcel OJ, 5 μm; Mobile phase: 4:1 carbon dioxide/(methanol containing 0.1% ammonium hydroxide)]. Example 57 was the first-eluting enantiomer. A pure sample of the second-eluting enantiomer was not obtained from the separation.

[35] Reaction of P2 with (3R)-tetrahydrofuran-3-carboxylic acid was mediated via 1-[3-(dimethylamino)propyl]-3-ethylcarbodiimide hydrochloride, 1H-benzotriazol-1-ol, and N,N-diisopropylethylamine.

Biological Assay

M4 Pam cAMP Assay

The M4 cAMP assay was designed to determine the potency and efficacy of muscarinic positive allosteric modulators (PAMs). Human M4 receptors were stably expressed in Human embryonic kidney (HEK293) cells expressed with the Promega GloSensor™ cAMP technology.

Cells:

HEK293 GloSensor cells expressing hM4 cells were cultured in growth media containing DMEM with 10% FBS, 1% Penicillin/Streptomycin, 500 µg/mL G418, 200 µg/mL Hygomycin B, and 1% Glutamax. When cells had grown to 80%-90% confluency, cells were harvested and seeded at a density of 25,000 cells/40 µL well, in a 384 white walled plates (Becton Dickinson 356661). Plates were incubated at 37 degrees C. and 5% $CO_2$ for use after 24 hours.

Compound Preparation for Activator Screen:

Test compounds were initially prepared as 100% DMSO stock solutions, then transferred and serially diluted in 384-well compound plates (Matrix #4325). Each compound was tested at 10 concentrations in duplicate per experiment. Compound plates are spotted with 0.2 µL/well activator at 400 times the final assay concentration. Positive and negative controls for the compound alone activator response was 10 µM acetylcholine (Sigma # A2661) and DMSO, respectively. $EC_{20}$ of acetylcholine was also used to define PAM activities.

cAMP Assay:

Promega GloSensor™reagent (Promega # E1291) had previously been aliquotted. For each experiment, a stock solution of GloSensor™ was thawed out and equilibration medium was prepared with 88% $CO_2$-independent media (Invitrogen #18045088), 10% fetal bovine serum and 2% GloSensor™ cAMP Reagent stock solution. Stock solution was mixed. Culture media in cell plates was discarded, then replaced with 40 µL/well pre-warmed equilibration media, then incubated in the dark at room temperature for 2 hours. During the incubation, stimulation media containing agonist and $EC_{20}$ acetylcholine was prepared. $CO_2$-independent media containing 50 n(nano instead of milli)M Isoproterenol representing an EC80 of b-adrenergic receptor activity (Sigma #16504, 400 times final concentration) and $EC_{20}$ acetylcholine in 1.25% DMSO was added to all columns of the compound plate, with the exception of column 12 to allow for $EC_0$ control. $EC_0$ control wells received stimulation media that does not contain $EC_{20}$ acetylcholine. Compounds are now 5 times the final assay concentration. The plate was mixed using a plate agitator. At the end of the 2 hour GloSensor™ incubation, add 10 µL of the $CO_2$-independent media containing agonist, $EC_{20}$ acetylcholine and isoproterenol to the cell plate. Cell plate was then incubated for 10 minutes at room temperature, and then read using an EnVision plate reader (Perkin Elmer).

Data Analysis:

Data was exported from the EnVision plate reader. The percent effect for each well was determined using the mean values for the positive and negative controls on each plate for each read, specifically 100*(compound−negative control)/(positive control−negative control). Dose response curves were fitted to the compound percent effect data using a 4-parameter logistic fit model. Data was reported as $EC_{50}$ and Emax, with the Emax as the maximum asymptote of the fitted dose response curve.

TABLE 2

Biological activity for Examples 1-59.

| Example Number | $EC_{50}$ Mean Asymptote Maximum (%)$^a$ | $EC_{50}$ (nM)$^a$ | IUPAC Name |
|---|---|---|---|
| 1 | 90.9 | 8.62 | 5,6,7-trimethyl-2-{[1-(pyridin-3-yl)azetidin-3-yl]acetyl}-1,2,3,5-tetrahydro-4H-pyrrolo[3,4-c]pyridin-4-one |
| 2 | 96.1$^b$ | 4.33$^b$ | 1-[6,7-dimethyl-4-(methylamino)-1,3-dihydro-2H-pyrrolo[3,4-c]pyridin-2-yl]-2-[1-(1,2,4-thiadiazol-5-yl)azetidin-3-yl]ethanone |
| 3 | 106 | 2.91 | 2-{1-[2-(difluoromethoxy)pyridin-4-yl]azetidin-3-yl}-1-[6,7-dimethyl-4-(methylamino)-1,3-dihydro-2H-pyrrolo[3,4-c]pyridin-2-yl]ethanone |
| 4 | 95.8$^b$ | 1.76$^b$ | 1-[6,7-dimethyl-4-(methylamino)-1,3-dihydro-2H-pyrrolo[3,4-c]pyridin-2-yl]-2-[1-(pyridin-3-yl)azetidin-3-yl]ethanone |
| 5 | 96.8 | 1.22 | 1-(pyridin-3-yl)azetidin-3-yl 6,7-dimethyl-4-(methylamino)-1,3-dihydro-2H-pyrrolo[3,4-c]pyridine-2-carboxylate |
| 6 | 92.0$^c$ | 50.6$^c$ | 6,7-dihydro-5H-cyclopenta[b]pyridin-6-yl 6,7-dimethyl-4-(methylamino)-1,3-dihydro-2H-pyrrolo[3,4-c]pyridine-2-carboxylate |
| 7 | 109 | 6.45 | 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone |
| 8 | 99.0 | 1.24 | 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-1 |
| 9 | 111 | 99.4 | 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-2 |
| 10 | 114 | 197 | 1-[6,7-dimethyl-4-(methylamino)-1,3-dihydro-2H-pyrrolo[3,4-c]pyridin-2-yl]-2-[trans-2-(pyridin-3-yl)cyclopropyl]ethanone, ENT-1 |

TABLE 2-continued

Biological activity for Examples 1-59.

| Example Number | EC$_{50}$ Mean Asymptote Maximum (%)$^a$ | EC$_{50}$ (nM)$^a$ | IUPAC Name |
|---|---|---|---|
| 11 | 94.8$^b$ | 1.60$^b$ | 1-[6,7-dimethyl-4-(methylamino)-1,3-dihydro-2H-pyrrolo[3,4-c]pyridin-2-yl]-2-[trans-2-(pyridin-3-yl)cyclopropyl]ethanone, ENT-2 |
| 12 | 89.3 | 19.9 | 2-[1-(pyridin-3-yl)azetidin-3-yl]-1-(4,6,7-trimethyl-1,3-dihydro-2H-pyrrolo[3,4-c]pyridin-2-yl)ethanone |
| 13 | 87.5 | 20.6 | 1-[6,7-dimethyl-4-(1-methyl-1H-pyrazol-4-yl)-1,3-dihydro-2H-pyrrolo[3,4-c]pyridin-2-yl]-2-[1-(pyridin-3-yl)azetidin-3-yl]ethanone |
| 14 | 99.4 | 18.5 | 1-{4-[(dimethylamino)methyl]-6,7-dimethyl-1,3-dihydro-2H-pyrrolo[3,4-c]pyridin-2-yl}-2-[1-(pyridin-3-yl)azetidin-3-yl]ethanone |
| 15 | 148 | 795 | 1-[6,7-dimethyl-4-(methylamino)-1,3-dihydro-2H-pyrrolo[3,4-c]pyridin-2-yl]-2-[trans-2-(6-fluoropyridin-3-yl)cyclopropyl]ethanone, ENT-1 |
| 16 | 102$^b$ | 0.838$^b$ | 1-[6,7-dimethyl-4-(methylamino)-1,3-dihydro-2H-pyrrolo[3,4-c]pyridin-2-yl]-2-[trans-2-(6-fluoropyridin-3-yl)cyclopropyl]ethanone, ENT-2 |
| 17 | 102 | 17.9 | 1-[4-(dimethylamino)-6,7-dimethyl-1,3-dihydro-2H-pyrrolo[3,4-c]pyridin-2-yl]-2-[1-(pyridin-3-yl)azetidin-3-yl]ethanone |
| 18 | 91.7 | 23.6 | 1-[4-(difluoromethyl)-6,7-dimethyl-1,3-dihydro-2H-pyrrolo[3,4-c]pyridin-2-yl]-2-[1-(pyridin-3-yl)azetidin-3-yl]ethanone |
| 19 | 92.3 | 1.23 | 1-[6,7-dimethyl-4-(methylamino)-1,3-dihydro-2H-pyrrolo[3,4-c]pyridin-2-yl]-2-[1-(pyrimidin-5-yl)azetidin-3-yl]ethanone |
| 20 | 95.1 | 30.4 | 1-[4-(dimethylamino)-6,7-dimethyl-1,3-dihydro-2H-pyrrolo[3,4-c]pyridin-2-yl]-2-[1-(pyrimidin-5-yl)azetidin-3-yl]ethanone |
| 21 | 99.7$^c$ | 8.72$^c$ | 6,7-dimethyl-2-{[1-(pyridin-3-yl)azetidin-3-yl]acetyl}-1,2,3,5-tetrahydro-4H-pyrrolo[3,4-c]pyridin-4-one |
| 22 | 99.7$^c$ | 0.626$^c$ | 1-{4-[(cyclopropylmethyl)amino]-6,7-dimethyl-1,3-dihydro-2H-pyrrolo[3,4-c]pyridin-2-yl}-2-[1-(pyrimidin-4-yl)azetidin-3-yl]ethanone |
| 23 | 95.9 | 1.44 | 1-[6,7-dimethyl-4-(methylamino)-1,3-dihydro-2H-pyrrolo[3,4-c]pyridin-2-yl]-2-[1-(pyrimidin-4-yl)azetidin-3-yl]ethanone |
| 24 | 98.2 | 7.27 | 2-(2,3-dihydro-1H-inden-2-yl)-1-[6,7-dimethyl-4-(methylamino)-1,3-dihydro-2H-pyrrolo[3,4-c]pyridin-2-yl]ethanone |
| 25 | 98.9 | 8.35 | 5,6,7-trimethyl-2-({1-[2-(trifluoromethyl)pyridin-4-yl]azetidin-3-yl}acetyl)-1,2,3,5-tetrahydro-4H-pyrrolo[3,4-c]pyridin-4-one |
| 26 | 90.8 | 2140 | 5,6,7-trimethyl-2-{[trans-2-(pyridin-3-yl)cyclopropyl]acetyl}-1,2,3,5-tetrahydro-4H-pyrrolo[3,4-c]pyridin-4-one, ENT-1 |
| 27 | 95.3 | 9.99 | 5,6,7-trimethyl-2-{[trans-2-(pyridin-3-yl)cyclopropyl]acetyl}-1,2,3,5-tetrahydro-4H-pyrrolo[3,4-c]pyridin-4-one, ENT-2 |
| 28 | 94.8 | <1.70 | 1-[6,7-dimethyl-4-(methylamino)-1,3-dihydro-2H-pyrrolo[3,4-c]pyridin-2-yl]-2-[trans-2-(pyrimidin-5-yl)cyclopropyl]ethanone |
| 29 | 96.3 | 690 | 1-[6,7-dimethyl-4-(methylamino)-1,3-dihydro-2H-pyrrolo[3,4-c]pyridin-2-yl]-2-[trans-2-(pyrimidin-5-yl)cyclopropyl]ethanone, ENT-1 |
| 30 | 95.1 | 1.58 | 1-[6,7-dimethyl-4-(methylamino)-1,3-dihydro-2H-pyrrolo[3,4-c]pyridin-2-yl]-2-[trans-2-(pyrimidin-5-yl)cyclopropyl]ethanone, ENT-2 |
| 31 | 102 | 12.1 | 4-{3-[6,7-dimethyl-4-(methylamino)-1,3-dihydro-2H-pyrrolo[3,4-c]pyridin-2-yl]-3-oxopropyl}benzonitrile |

TABLE 2-continued

Biological activity for Examples 1-59.

| Example Number | EC$_{50}$ Mean Asymptote Maximum (%)$^a$ | EC$_{50}$ (nM)$^a$ | IUPAC Name |
|---|---|---|---|
| 32 | 119 | 24.7 | 1-[6,7-dimethyl-4-(methylamino)-1,3-dihydro-2H-pyrrolo[3,4-c]pyridin-2-yl]-3-(4-methoxyphenyl)propan-1-one |
| 33 | 128 | 5.32 | 2-[trans-2-(6-chloropyridin-3-yl)cyclopropyl]-1-[6,7-dimethyl-4-(methylamino)-1,3-dihydro-2H-pyrrolo[3,4-c]pyridin-2-yl]ethanone |
| 34 | 95.9 | 1.30 | 1-[6,7-dimethyl-4-(methylamino)-1,3-dihydro-2H-pyrrolo[3,4-c]pyridin-2-yl]-2-{1-[2-(trifluoromethyl)pyridin-4-yl]azetidin-3-yl}ethanone |
| 35 | 97.7$^c$ | 13.6$^c$ | 1-[6,7-dimethyl-4-(methylamino)-1,3-dihydro-2H-pyrrolo[3,4-c]pyridin-2-yl]-2-[1-(2-methylpyridin-4-yl)azetidin-3-yl]ethanone |
| 36 | 95.6$^c$ | 5.46$^c$ | 4-(3-{2-[6,7-dimethyl-4-(methylamino)-1,3-dihydro-2H-pyrrolo[3,4-c]pyridin-2-yl]-2-oxoethyl}azetidin-1-yl)pyridine-2-carbonitrile |
| 37 | 93.5 | 3.47 | 1-[6,7-dimethyl-4-(methylamino)-1,3-dihydro-2H-pyrrolo[3,4-c]pyridin-2-yl]-2-[1-(1,3,4-thiadiazol-2-yl)azetidin-3-yl]ethanone |
| 38 | 102 | 13.8 | 1-[6,7-dimethyl-4-(methylamino)-1,3-dihydro-2H-pyrrolo[3,4-c]pyridin-2-yl]-3-(1H-pyrazol-4-yl)propan-1-one |
| 39 | 101$^c$ | 32.0$^c$ | 1-[4-(difluoromethyl)-6,7-dimethyl-1,3-dihydro-2H-pyrrolo[3,4-c]pyridin-2-yl]-2-{1-[2-(difluoromethyl)pyridin-4-yl]azetidin-3-yl}ethanone |
| 40 | 121$^c$ | 6.77$^c$ | 1-[6,7-dimethyl-4-(methylamino)-1,3-dihydro-2H-pyrrolo[3,4-c]pyridin-2-yl]-2-[trans-2-(4-fluorophenyl)cyclopropyl]ethanone, ENT-1 |
| 41 | 145$^c$ | 783$^c$ | 1-[6,7-dimethyl-4-(methylamino)-1,3-dihydro-2H-pyrrolo[3,4-c]pyridin-2-yl]-2-[trans-2-(4-fluorophenyl)cyclopropyl]ethanone, ENT-2 |
| 42 | 116$^c$ | 6.96$^c$ | 2-{1-[2-(trifluoromethyl)pyridin-4-yl]azetidin-3-yl}-1-[1,6,7-trimethyl-4-(methylamino)-1,3-dihydro-2H-pyrrolo[3,4-c]pyridin-2-yl]ethanone |
| 43 | 152$^c$ | 3670$^c$ | 2-{1-[2-(trifluoromethyl)pyridin-4-yl]azetidin-3-yl}-1-[1,6,7-trimethyl-4-(methylamino)-1,3-dihydro-2H-pyrrolo[3,4-c]pyridin-2-yl]ethanone, ENT-1 |
| 44 | 107$^c$ | 1.80$^c$ | 2-{1-[2-(trifluoromethyl)pyridin-4-yl]azetidin-3-yl}-1-[1,6,7-trimethyl-4-(methylamino)-1,3-dihydro-2H-pyrrolo[3,4-c]pyridin-2-yl]ethanone, ENT-2 |
| 45 | 105$^c$ | 3.56$^c$ | 1-[6,7-dimethyl-4-(methylamino)-1,3-dihydro-2H-pyrrolo[3,4-c]pyridin-2-yl]-2-[trans-2-(6-methylpyridin-3-yl)cyclopropyl]ethanone |
| 46 | N.D.$^d$ | >10000$^c$ | 1-[6,7-dimethyl-4-(methylamino)-1,3-dihydro-2H-pyrrolo[3,4-c]pyridin-2-yl]-2-[trans-2-(6-methylpyridin-3-yl)cyclopropyl]ethanone, ENT-1 |
| 47 | 115$^b$ | 2.05$^b$ | 1-[6,7-dimethyl-4-(methylamino)-1,3-dihydro-2H-pyrrolo[3,4-c]pyridin-2-yl]-2-[trans-2-(6-methylpyridin-3-yl)cyclopropyl]ethanone, ENT-2 |
| 48 | 96.8$^c$ | 8.46$^c$ | [6,7-dimethyl-4-(methylamino)-1,3-dihydro-2H-pyrrolo[3,4-c]pyridin-2-yl](1-methyl-1H-pyrazol-4-yl)methanone |
| 49 | 140$^c$ | 754$^c$ | 2-{1-[2-(difluoromethoxy)pyridin-4-yl]azetidin-3-yl}-1-[1,6,7-trimethyl-4-(methylamino)-1,3-dihydro-2H-pyrrolo[3,4-c]pyridin-2-yl]ethanone, ENT-1 |
| 50 | 104$^c$ | 9.88$^c$ | 2-{1-[2-(difluoromethoxy)pyridin-4-yl]azetidin-3-yl}-1-[1,6,7-trimethyl-4-(methylamino)-1,3-dihydro-2H-pyrrolo[3,4-c]pyridin-2-yl]ethanone, ENT-2 |

TABLE 2-continued

Biological activity for Examples 1-59.

| Example Number | EC$_{50}$ Mean Asymptote Maximum (%)$^a$ | EC$_{50}$ (nM)$^a$ | IUPAC Name |
|---|---|---|---|
| 51 | 97.7$^c$ | 3.26$^c$ | 1-[6,7-dimethyl-4-(methylamino)-1,3-dihydro-2H-pyrrolo[3,4-c]pyridin-2-yl]-2-[1-(6-fluoropyridin-3-yl)azetidin-3-yl]ethanone |
| 52 | 84.5$^b$ | 36.1$^b$ | 1-(6,7-dimethyl-1,3-dihydro-2H-pyrrolo[3,4-c]pyridin-2-yl)-2-[1-(pyridin-3-yl)azetidin-3-yl]ethanone |
| 53 | 92.1$^b$ | 43.8$^b$ | 1-(4-methoxy-6,7-dimethyl-1,3-dihydro-2H-pyrrolo[3,4-c]pyridin-2-yl)-2-[1-(pyridin-3-yl)azetidin-3-yl]ethanone |
| 54 | 95.8 | 153 | 1-[4-(methoxymethyl)-6,7-dimethyl-1,3-dihydro-2H-pyrrolo[3,4-c]pyridin-2-yl]-2-[1-(pyridin-3-yl)azetidin-3-yl]ethanone |
| 55 | 96.1 | 78.7 | 1-(4-methoxy-6,7-dimethyl-1,3-dihydro-2H-pyrrolo[3,4-c]pyridin-2-yl)-2-[1-(pyrimidin-5-yl)azetidin-3-yl]ethanone |
| 56 | 109$^c$ | 150$^c$ | 1-[4-(difluoromethoxy)-6,7-dimethyl-1,3-dihydro-2H-pyrrolo[3,4-c]pyridin-2-yl]-2-[1-(pyrimidin-5-yl)azetidin-3-yl]ethanone |
| 57 | 97.0$^c$ | 30.9$^c$ | 1-[6,7-dimethyl-4-(methylamino)-1,3-dihydro-2H-pyrrolo[3,4-c]pyridin-2-yl]-2-(5-fluoro-2,3-dihydro-1H-inden-2-yl)ethanone, ENT-1 |
| 58 | 96.2$^c$ | 95.2$^c$ | cyclopropyl[6,7-dimethyl-4-(methylamino)-1,3-dihydro-2H-pyrrolo[3,4-c]pyridin-2-yl]methanone |
| 59 | 95.5$^c$ | 149$^c$ | [6,7-dimethyl-4-(methylamino)-1,3-dihydro-2H-pyrrolo[3,4-c]pyridin-2-yl][(3R)-tetrahydrofuran-3-yl]methanone |

$^a$Values represent the geometric mean of 2-4 determinations, unless otherwise indicated.
$^b$Value represents the geometric mean of ≥5 determinations.
$^c$Value represents a single determination.
$^d$Not determined.

What is claimed is:

1. A compound of Formula (I):

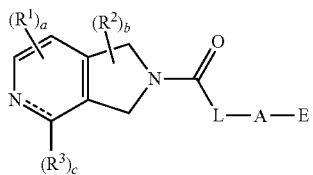

(I)

or an N-oxide thereof, or a pharmaceutically acceptable salt of the compound or the N-oxide, wherein:

each $R^1$, when present, is independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, optionally substituted (C$_3$-C$_6$)cycloalkyl, optionally substituted —O—(C$_3$-C$_6$)cycloalkyl, —N(R$^4$)(R$^5$), —N(R$^4$)(C═O)(R$^5$), —C(═O)N(R$^4$)(R$^5$), —O—C(═O)—N(R$^4$)(R$^5$), —C(═O)—R$^4$, and —C(═O)—OR$^4$;

a is an integer selected from 0, 1, 2, and 3;

each $R^2$, when present, is independently selected from the group consisting of hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C═O)(R$^5$), —C(═O)N(R$^4$)(R$^5$), —O—C(═O)—N(R$^4$)(R$^5$), —C(═O)—R$^4$, and —C(═O)—OR$^4$;

b is an integer selected from 0, 1, 2, 3, and 4;

$R^3$, when present, is independently selected from the group consisting of halogen, cyano, hydroxy, oxo, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, optionally substituted (C$_3$-C$_6$)cycloalkyl, optionally substituted —O—(C$_3$-C$_6$)cycloalkyl, optionally substituted (5- to 6-membered)heteroaryl, —N(R$^4$)(R$^5$), —N(R$^4$)(C═O)(R$^5$), —C(═O)N(R$^4$)(R$^5$), —O—C(═O)—N(R$^4$)(R$^5$), —C(═O)—R$^4$, and —C(═O)—OR, provided that when R$^3$ is oxo, then ═ is a single bond, or when c is 0 then R$^3$ is absent and ═ is a double bond;

c is an integer selected from 0 and 1;

L is —(CH$_2$)$_m$—, wherein m is an integer selected from 0, 1 and 2;

A is (C$_3$-C$_6$)cycloalkyl, wherein said cycloalkyl is optionally substituted with one to five substituents independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C═O)(R$^5$), —C(═O)N(R$^4$)(R$^5$), —O—C(═O)—N(R$^4$)(R$^5$), —C(═O)—R$^4$, and —C(═O)—OR$^4$;

129

E is selected from $(C_3-C_{12})$cycloalkyl, $(C_6-C_{10})$aryl, (5- to 6-membered)heterocycloalkyl, and (5- to 10-membered)heteroaryl, wherein said cycloalkyl, aryl, and heteroaryl are optionally substituted with one to five substituents independently selected from the group consisting of halogen, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, optionally substituted $(C_3-C_6)$cycloalkyl, methyloxetanyl, —$N(R^4)(R^5)$, —$N(R^4)(C(=O)R^5)$, —$C(=O)N(R^4)(R^5)$, —O—$C(=O)$—$N(R^4)(R^5)$, —$C(=O)$—$R^4$, and —$C(=O)$—$OR^4$; and $R^4$ and $R^5$ at each occurrence are each independently selected from hydrogen and optionally substituted $(C_1-C_6)$alkyl; or $R^4$ and $R^5$ taken together with the nitrogen to which they are attached form an optionally substituted (4- to 6-membered)heterocycloalkyl.

2. The compound according to claim 1, or an N-oxide thereof, or a pharmaceutically acceptable salt of the compound or the N-oxide, wherein $R^1$ is an optionally substituted $(C_1-C_6)$alkyl; a is an integer selected from 1, 2, and 3; each $R^2$, when present, is an optionally substituted $(C_1-C_6)$alkyl; b is an integer selected from 0 or 1; $R^3$, when present, is independently selected from the group consisting of oxo, optionally substituted $(C_1-C_6)$alkyl, optionally substituted $(C_1-C_6)$alkoxy, and —$N(R^4)(R^5)$, provided that when $R^3$ is oxo, then ═ is a single bond, or when c is 0 then $R^3$ is absent and ═ is a double bond; and c is an integer selected from 0 and 1.

3. The compound according to claim 1, or an N-oxide thereof, or a pharmaceutically acceptable salt of the compound or the N-oxide, wherein L is —$(CH_2)_m$— and m is an integer selected from 1 and 2.

4. The compound according to claim 1, or an N-oxide thereof, or a pharmaceutically acceptable salt of the compound or the N-oxide, wherein L is —$(CH_2)_m$— and m is 1.

5. The compound according to claim 1, or an N-oxide thereof, or a pharmaceutically acceptable salt of the compound or the N-oxide, wherein A is a $(C_3-C_8)$cycloalkyl selected from the group consisting of cyclopropyl, cyclobutyl, cyclopentyl, and cyclohexyl, wherein said cycloalkyl is optionally substituted with one to three substituents independently selected from the group consisting of halogen, cyano, —$N(R^3)(R^4)$, optionally substituted $(C_1-C_6)$alkyl, and optionally substituted $(C_1-C_6)$alkoxy.

6. The compound according to claim 5, or an N-oxide thereof, or a pharmaceutically acceptable salt of the compound or the N-oxide, wherein A is cyclopropyl.

7. The compound according to claim 1, or an N-oxide thereof, or a pharmaceutically acceptable salt of the compound or the N-oxide, wherein E is a (5- to 10-membered) heteroaryl selected from the group consisting of triazolyl, imidazolyl, furanyl, isoxazolyl, isothiazolyl, 1,2,3-, 1,2,4-, 1,2,5-, or 1,3,4-oxadiazolyl, oxazolyl, thiophenyl, thiazolyl, thiadiazolyl, isothiazolyl, pyrazolyl, pyridinyl, pyrazinyl, pyrimidinyl, pyridazinyl, indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl, anthranilyl, quinolinyl, isoquinolinyl, cinnolinyl, quinazolinyl, oxochromanyl, and 1,4-benzoxazinyl, wherein said heteroaryl is optionally substituted with one to three substituents independently selected

130 from the group consisting of halogen, cyano, —$N(R^3)(R^4)$, optionally substituted $(C_1-C_6)$alkyl, and optionally substituted $(C_1-C_6)$alkoxy.

8. The compound according to claim 7, or an N-oxide thereof, or a pharmaceutically acceptable salt of the compound or the N-oxide, wherein the heteroaryl is a (5- to 6-membered)nitrogen-containing heteroaryl selected from the group consisting of thiadiazolyl, pyrazolyl, pyridinyl, pyrazinyl, and pyrimidinyl, wherein said nitrogen-containing heteroaryl is optionally substituted with one to three substituents independently selected from the group consisting of halogen, cyano, —$N(R^3)(R^4)$, optionally substituted $(C_1-C_6)$alkyl, and optionally substituted $(C_1-C_6)$alkoxy.

9. A compound of Formula Ib:

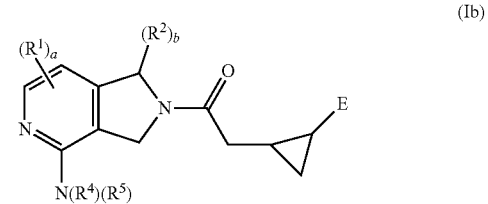

(Ib)

or an N-oxide thereof, or a pharmaceutically acceptable salt of the compound or the N-oxide, wherein:

each $R^1$, when present, is independently selected from the group consisting of halogen, optionally substituted $(C_1-C_6)$alkyl, and optionally substituted $(C_1-C_6)$alkoxy;

a is an integer selected from 1, 2 and 3;

$R^2$, when present, is an optionally substituted $(C_1-C_6)$alkyl;

b is an integer selected from 0 and 1;

$R^4$ and $R^5$ at each occurrence are each independently selected from hydrogen and optionally substituted $(C_1-C_6)$alkyl; and E is a (5- to 6-membered)heteroaryl, wherein said heteroaryl is optionally substituted with one to three substituents independently selected from the group consisting of halogen, cyano, hydroxy, optionally substituted $(C_1-C_6)$alkyl, optionally substituted $(C_1-C_6)$alkoxy, and —$N(R^4)(R^5)$, wherein $R^4$ and $R^5$ at each occurrence are each independently selected from hydrogen and optionally substituted $(C_1-C_6)$alkyl.

10. The compound according to claim 9, or an N-oxide thereof, or a pharmaceutically acceptable salt of the compound or the N-oxide, wherein E is a (5- to 6-membered) nitrogen-containing heteroaryl selected from the group consisting of pyrazolyl, thiadiazolyl, pyridinyl, and pyrimidinyl.

11. The compound according to claim 10, or an N-oxide thereof, or a pharmaceutically acceptable salt of the compound or the N-oxide, wherein the (5- to 6-membered) nitrogen-containing heteroaryl is pyrimidinyl.

12. The compound according to claim 10, or an N-oxide thereof, or a pharmaceutically acceptable salt of the compound or the N-oxide, wherein the (5- to 6-membered) nitrogen-containing heteroaryl is pyridinyl.

13. The compound according to claim 1, wherein the compound is selected from the group consisting of:

1-(4-amino-6,7-dimethyl-1,3-dihydro-2H-pyrrolo[3,4-c] pyridin-2-yl)-2-[trans-2-(6-fluoropyridin-3-yl)cyclopropyl]ethanone;

1-(4-amino-6,7-dimethyl-1,3-dihydro-2H-pyrrolo[3,4-c]pyridin-2-yl)-2-[trans-2-(6-fluoropyridin-3-yl)cyclopropyl]ethenone, ENT-1;

1-(4-amino-6,7-dimethyl-1,3-dihydro-2H-pyrrolo[3,4-c]pyridin-2-yl)-2-[trans-2-(6-fluoropyridin-3-yl)cyclopropyl]ethenone, ENT-2;

1-[6,7-dimethyl-4-(methylamino)-1,3-dihydro-2H-pyrrolo[3,4-c]pyridin-2-yl]-2-[trans-2-(pyridin-3-yl)cyclopropyl]ethanone, ENT-1;

1-[6,7-dimethyl-4-(methylamimo)-1,3-dihydro-2H-pyrrolo[3,4-c]pyridin- 2-yl]-2-[trans-2-(pyridin-3-yl)cyclopropyl]ethanone, ENT-2;

1-[6,7-dimethyl-4-(methylamino)-1,3-dihydro-2H-pyrrolo[3,4-c]pyridin-2-yl]-2-[trans-2-(6-fluoropyridin-3-yl)cyclopropyl]ethanone, ENT-1;

1-[6,7-dimethyl-4-(methylamino)-1,3-dihydro-2H-pyrrolo[3,4-c]pyridin-2-yl]-2-[trans-2-(6-fluoropyridin-3-yl)cyclopropyl]ethanone, ENT-2;

5,6,7-trimethyl-2-{[trans-2-(pyridin-3-yl)cyclopropyl]acetyl}-1,2,3,5-tetrahydro-4H-pyrrolo[3,4-c]pyridin-4-one, ENT-1;

5,6,7-trimethyl-2-{[trans-2-(pyridin-3-yl)cyclopropyl]acetyl}-1,2,3,5-tetrahydro-4H-pyrrolo[3,4-c]pyridin-4-one, ENT-2;

1-[6,7-dimethyl-4-(methylamino)-1,3-dihydro-2H-pyrrolo[3,4-c]pyridin-2-yl]-2-[trans-2-(pyrimidin-5-yl)cyclopropyl]ethanone;

1-[6,7-dimethyl-4-(methylamino)-1,3-dihydro-2H-pyrrolo[3,4-c]pyridin-2-yl]-2-[trans-2-(pyrimidin-5-yl)cyclopropyl]ethenone, ENT-1;

1-[6,7-dimethyl-4-(methylamino)-1,3-dihydro-2H-pyrrolo[3,4-c]pyridin-2-yl]-2-[trans-2-(pyrimidin-5-yl)cyclopropyl]ethenone, ENT-2;

2-[trans-2-(6-chloropyridin-3-yl)cyclopropyl]-1-[6,7-dimethyl-4-(methylamino)-1,3-dihydro-2H-pyrrolo[3,4-c]pyridin-2-yl]ethanone;

1-[6,7-dimethyl-4-(methylamino)-1,3-dihydro-2H-pyrrolo[3,4-c]pyridin-2-yl]-2-[trans-2-(4-fluorophenyl)cyclopropyl]ethanone, ENT-1;

1-[6,7-dimethyl-4-(methylamino)-1,3-dihydro-2H-pyrrolo[3,4-c]pyridin-2-yl]-2-[trans-2-(4-fluorophenyl)cyclopropyl]ethanone, ENT-2;

1-[6,7-dimethyl-4-(methyl amino)-1,3-dihydro-2H-pyrrolo[3,4-c]pyridin-2-yl]-2-[trans-2-(6-methylpyridin-3-yl)cyclopropyl]ethenone;

1-[6,7-dimethyl-4-(methyl amino)-1,3-dihydro-2H-pyrrolo[3,4-c]pyridin-2-yl]-2-[trans-2-(6-methylpyridin-3-yl)cyclopropyl]ethenone, ENT-1; and 1-[6,7-dimethyl-4-(methylamino)-1,3-dihydro-2H-pyrrolo[3,4-c]pyridin-2-yl]-2-[trans-2-(6-methylpyridin-3-yl)cyclopropyl]ethenone, ENT-2; or an N-oxide thereof, or a pharmaceutically acceptable salt thereof or pharmaceutically acceptable salt of the N-oxide.

14. The compound according to claim 1 that is 1-[6,7-dimethyl-4-(methylamino)-1,3-dihydro-2H-pyrrolo[3,4-c]pyridin-2-yl]-2-[trans-2-(6-fluoropyridin-3-yl)cyclopropyl]ethanone, or an N-oxide thereof, or a pharmaceutically acceptable salt thereof, or a pharmaceutically acceptable salt of the N-oxide.

15. A pharmaceutical composition comprising a therapeutically effective amount of a compound, or N-oxide, or pharmaceutically acceptable salt, or pharmaceutically acceptable salt of the N-oxide according to claim 1, and a pharmaceutically acceptable carrier.

16. A method for treating an M4-associated disease or disorder in a subject, said method comprising administering to the patient a therapeutically effective amount of a compound, or N-oxide, or pharmaceutically acceptable salt, or pharmaceutically acceptable salt of the N-oxide according to claim 1, or the pharmaceutical composition according to claim 15.

17. The method of claim 16, wherein the M4-associated disease or disorder is selected from the group consisting of Alzheimer's Disease, schizophrenia or psychosis, pain, addiction, a sleep disorder, a cognitive disorder (e.g. mild cognitive impairment), Parkinson's Disease, Parkinson's Disease-levodopa-induced dyskinesia, Huntington's Disease, dyskinesia, dry mouth, pulmonary hypertension, chronic obstructive pulmonary disease (COPD), asthma, urinary incontinence, glaucoma, Trisomy 21 (Down Syndrome), cerebral amyloid angiopathy, dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis.

18. The method of claim 17, wherein the M4-associated disease or disorder is from the group consisting of Alzheimer's Disease, schizophrenia, pain, addiction, and a sleep disorder.

19. The compound according to claim 1 that is 1-(4-amino-6,7-dimethyl-1,3-dihydro-2H-pyrrolo[3,4-c]pyridin-2-yl)-2-[trans-2-(6-fluoropyridin-3-yl)cyclopropyl]ethenone, or a stereoisomer thereof, or an N-oxide thereof, or a pharmaceutically acceptable salt thereof, or a pharmaceutically acceptable salt of the stereoisomer or the N-oxide.

20. The compound according to claim 1, wherein the compound is 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-1, or an N-oxide thereof, or a pharmaceutically acceptable salt of the compound or the N-oxide.

21. The compound according to claim 1, wherein the compound is 1-(4-amino-6,7-dimethyl-1,3-dihydro-2H-pyrrolo[3,4-c]pyridin-2-yl)-2-[trans-2-(6-fluoropyridin-3-yl)cyclopropyl]ethanone, ENT-2, or an N-oxide thereof, or a pharmaceutically acceptable salt of the compound or the N-oxide.

* * * * *